United States Patent
Goldfine et al.

(10) Patent No.: US 6,952,095 B1
(45) Date of Patent: Oct. 4, 2005

(54) SURFACE MOUNTED AND SCANNING SPATIALLY PERIODIC EDDY-CURRENT SENSOR ARRAYS

(75) Inventors: Neil J. Goldfine, Newton, MA (US); Darrell E. Schlicker, Watertown, MA (US); Andrew P. Washabaugh, Chula Vista, CA (US); Vladimir A. Zilberstein, Chestnut Hill, MA (US); Vladimir Tsukernik, West Roxbury, MA (US)

(73) Assignee: JENTEK Sensors, Inc., Waltham, MA (US)

( * ) Notice: Subject to any disclaimer, the term of this patent is extended or adjusted under 35 U.S.C. 154(b) by 435 days.

(21) Appl. No.: 09/666,524

(22) Filed: Sep. 20, 2000

Related U.S. Application Data

(63) Continuation-in-part of application No. 09/656,723, filed on Sep. 7, 2000, now abandoned.
(60) Provisional application No. 60/203,744, filed on May 12, 2000, and provisional application No. 60/155,038, filed on Sep. 20, 1999.

(51) Int. Cl.$^7$ .................... G01N 27/82; G01N 27/72; G01R 33/12
(52) U.S. Cl. .............. 324/240; 324/242; 324/243; 324/202
(58) Field of Search ................ 324/227, 232, 324/239, 202, 240, 241, 242, 243

(56) References Cited

U.S. PATENT DOCUMENTS

| | | | | |
|---|---|---|---|---|
| 4,271,393 A | * | 6/1981 | Hansen et al. | 324/240 |
| 4,644,271 A |   | 2/1987 | Toth et al. | 324/238 |

(Continued)

FOREIGN PATENT DOCUMENTS

| | | | | |
|---|---|---|---|---|
| EP | 0 577 244 A2 |   | 1/1994 |   |
| EP | 0 884 588 A1 |   | 12/1998 |   |
| GB | 886247 | * | 1/1962 | 324/238 |
| GB | 1 567 600 A |   | 5/1980 |   |
| WO | WO 98/30921 |   | 7/1998 |   |
| WO | WO 98/40732 |   | 9/1998 |   |
| WO | WO 99/22231 |   | 5/1999 |   |
| WO | WO 99/26062 |   | 5/1999 |   |

* cited by examiner

*Primary Examiner*—Jay Patidar
(74) *Attorney, Agent, or Firm*—Hamilton, Brook, Smith & Reynolds, P.C.

(57) ABSTRACT

Inductive sensors measure the near surface properties of conducting and magnetic material. A sensor may have primary windings with parallel extended winding segments to impose a spatially periodic magnetic field in a test material. Those extended portions may be formed by adjacent portions of individual drive coils. Sensing elements provided every other half wavelength may be connected together in series while the sensing elements in adjacent half wavelengths are spatially offset. Certain sensors include circular segments which create a circularly symmetric magnetic field that is periodic in the radial direction. Such sensors are particularly adapted to surround fasteners to detect cracks and can be mounted beneath a fastener head. In another sensor, sensing windings are offset along the length of parallel winding segments to provide material measurements over different locations when the circuit is scanned over the test material. The distance from the sensing elements to the ends of the primary winding may be kept constant as the offset space in between sensing elements is varied. An image of the material properties can be provided as the sensor is scanned across the material.

58 Claims, 65 Drawing Sheets

U.S. PATENT DOCUMENTS

| | | | |
|---|---|---|---|
| 4,810,966 A | 3/1989 | Schmall | 324/207 |
| 4,963,826 A | 10/1990 | Capobianco et al. | 324/202 |
| 5,006,800 A | 4/1991 | Hedengren et al. | 324/233 |
| 5,015,951 A | 5/1991 | Melcher | 324/232 |
| 5,227,731 A | 7/1993 | Prabhakaran et al. | 324/718 |
| 5,262,722 A | 11/1993 | Hedengren et al. | 324/718 |
| 5,311,128 A | 5/1994 | Lareau et al. | 324/233 |
| 5,453,689 A | 9/1995 | Goldfine et al. | 324/239 |
| 5,549,803 A | 8/1996 | Schoess et al. | 204/404 |
| 5,610,517 A | 3/1997 | Ma et al. | 324/233 |
| 5,629,621 A | 5/1997 | Goldfine et al. | 324/239 |
| 5,698,977 A | 12/1997 | Simpson et al. | 324/209 |
| 5,793,206 A | 8/1998 | Goldfine et al. | 324/242 |
| 5,966,011 A | 10/1999 | Goldfine et al. | 324/242 |
| 5,969,260 A | 10/1999 | Belk et al. | 73/773 |
| 6,657,429 B1 | 12/2003 | Goldfine et al. | |

Crack

LOAD

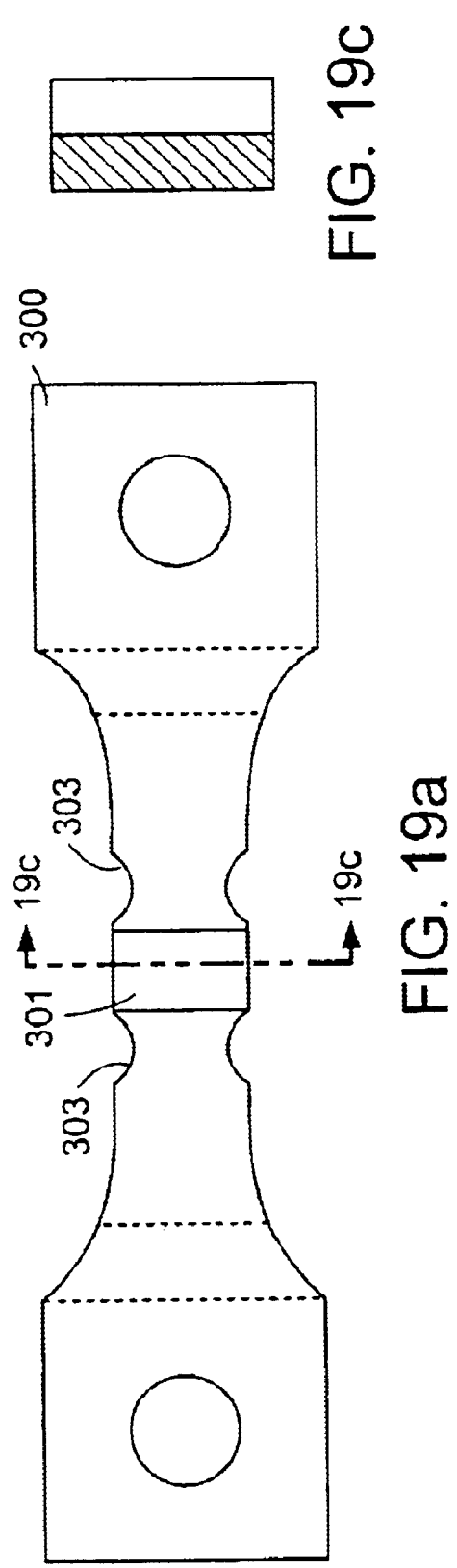
FIG. 19a
FIG. 19c
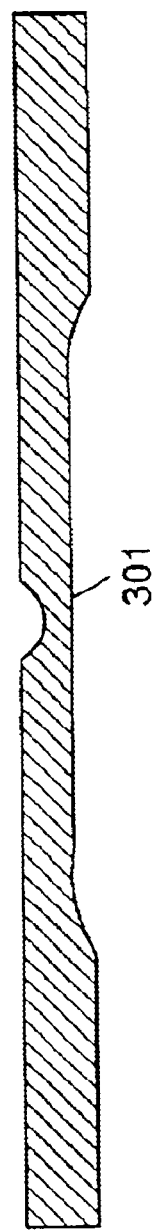
FIG. 19b

SURFACE MOUNTED AND SCANNING SPATIALLY PERIODIC EDDY-CURRENT SENSOR ARRAYS

RELATED APPLICATION(S)

This application is a Continuation-in-Part of U.S. application Ser. No. 09/656,723 filed Sep. 7, 2000, now abandoned, which claims the benefit of U.S. Provisional Application Nos. 60/203,744 filed May 12, 2000 and 60/155,038 filed Sep. 20, 1999, the entire teachings of which are incorporated herein by reference.

GOVERNMENT SUPPORT

The invention was supported, in whole or in part, by a Contract Number DTRS57-96-C-00108 from the Department of Transportation, Federal Aviation Administration, by Contract Number N00421-97-C-1120 from the Department of the Navy. The Government has certain rights in the invention.

BACKGROUND OF THE INVENTION

The technical field of this invention is that of nondestructive materials characterization, particularly quantitative, model-based characterization of surface, near-surface, and bulk material condition for flat and curved parts or components using eddy-current sensors. Characterization of bulk material condition includes (1) measurement of changes in material state caused by fatigue damage, creep damage, thermal exposure, or plastic deformation; (2) assessment of residual stresses and applied loads; and (3) assessment of processing-related conditions, for example from shot peening, roll burnishing, thermal-spray coating, or heat treatment. It also includes measurements characterizing material, such as alloy type, and material states, such as porosity and temperature. Characterization of surface and near-surface conditions includes measurements of surface roughness, displacement or changes in relative position, coating thickness, and coating condition. Each of these also includes detection of electromagnetic property changes associated with single or multiple cracks. Spatially periodic field eddy-current sensors have been used to measure foil thickness, characterize coatings, and measure porosity, as well as to measure property profiles as a function of depth into a part, as disclosed in U.S. Pat. Nos. 5,232,951 and 5,239,689.

Conventional eddy-current sensing involves the excitation of a conducting winding, the primary, with an electric current source of prescribed frequency. This produces a time-varying magnetic field at the same frequency, which in turn is detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the impedance between the primary and secondary windings. Traditionally, scanning of eddy-current sensors across the material surface is then used to detect flaws, such as cracks.

For the inspection of structural members in an aircraft, power plant, etc., it is desirable to detect and monitor material damage, crack initiation and crack growth due to fatigue, creep, stress corrosion cracking, etc. in the earliest stages possible in order to verify the integrity of the structure. This is particularly critical for aging aircraft, where military and commercial aircraft are being flown well beyond their original design lives. This requires increased inspection, maintenance, and repair of aircraft components, which also leads to escalating costs. For example, the useful life of the current inventory of aircraft in the U.S. Air Force (e.g., T-38, F-16, C-130E/H, A-10, AC/RC/KC-135, U-2, E-3, B-1B, B-52H) is being extended an additional 25 years at least [Air Force Association, 1997, Committee, 1997]. Similar inspection capability requirements also apply to the lifetime extension of engine components [Goldfine, 1998].

Safely supporting life extension for structures requires both rapid and cost effective inspection capabilities. The necessary inspection capabilities include rapid mapping of fatigue damage and hidden corrosion over wide areas, reduced requirements for calibration and field standards, monitoring of difficult-to-access locations without disassembly, continuous on-line monitoring for crack initiation and growth, detection of cracks beneath multiple layers of material (e.g., second layer crack detection), and earlier detection of cracks beneath fastener heads with fewer false alarms. In general, each inspection capability requires a different sensor configuration.

The use of eddy-current sensors for inspection of critical locations is an integral component of the damage tolerance and retirement for cause methods used for commercial and military aircraft. The acceptance and successful implementation of these methods over the last three decades has enabled life extension and safer operation for numerous aircraft. The corresponding accumulation of fatigue damage in critical structural members of these aging aircraft, however, is an increasingly complex and continuing high priority problem. Many components that were originally designed to last the design life of the aircraft without experiencing cracking (i.e., safe life components) are now failing in service, both because aircraft remain in service beyond original design life and, for military aircraft, because expanded mission requirements expose structures to unanticipated loading scenarios. New life extension programs and recommended repair and replacement activities are often excessively burdensome because of limitations in technology available today for fatigue detection and assessment. Managers of the Aircraft Structural Integrity Program (ASIP) are often faced with difficult decisions to either replace components on a fleet-wide basis or introduce costly inspection programs.

Furthermore, there is growing evidence that (1) multiple site damage or multiple element damage may compromise fail safety in older aircraft, and (2) significant fatigue damage, with subsequent formation of cracks, may occur at locations not considered critical in original fatigue evaluations. In application of damage tolerance, inspection schedules are often overly conservative because of limitations in fatigue detection capability for early stage damage. Even so, limited inspection reliability has led to numerous commercial and military component failures.

A better understanding of crack initiation and short crack growth behavior also affects both the formulation of damage tolerance methodologies and design modifications on new aircraft and aging aircraft. For safe-life components, designed to last the life of the aircraft, no inspection requirements are typically planned for the first design life. Life extension programs have introduced requirements to inspect these "safe-life" components in service since they are now operating beyond the original design life. However, there are also numerous examples of components originally designed on a safe-life basis that have failed prior to or near their originally specified design life on both military and commercial aircraft.

For safe-life components that must now be managed by damage tolerance methods, periodic inspections are generally far more costly than for components originally designed with planned inspections. Often the highest cost is associated with disassembly and surface preparation. Additionally, readiness of the fleet is directly limited by time out of service and reduced mission envelopes as aircraft age and inspection requirements become more burdensome. Furthermore, the later an inspection uncovers fatigue damage the more costly and extensive the repair, or the more likely replacement is required. Thus, inspection of these locations without disassembly and surface preparation is of significant advantage; also, the capability to detect fatigue damage at early stages can provide alternatives for component repair (such as minimal material removal and shotpeening) that will permit life extension at a lower cost than current practice.

In general, fatigue damage in metals progresses through distinct stages These stages can be characterized as follows [S. Suresh, 1998]: (1) substructural and microstructural changes which cause nucleation of permanent damage, (2) creation of microscopic cracks, (3) growth and coalescence of these microscopic flaws to form 'dominant' cracks, (4) stable propagation of the dominant macrocrack, and (5) structural instability or complete fracture.

Although there are differences of opinion within the fatigue analysis community, Suresh defines the third stage as the demarcation between crack initiation and propagation. Thus, the first two of the above stages and at least the initial phase of Stage 3 are generally thought of, from a practical engineering perspective, as the crack initiation phase.

In Stage 1, microplastic strains develop at the surface even at nominal stresses in the elastic range. Plastic deformation is associated with movement of linear defects known as dislocations. In a given load cycle, a microscopic step can form at the surface as a result of localized slip forming a "slip line". These slip lines appear as parallel lines or bands commonly called "persistent slip bands" (PSBs). Slip band intrusions become stress concentration sites where microcracks can develop.

Historically, X-ray diffraction and electrical resistivity are among the few nondestructive methods that have been explored for detection of fatigue damage in the initiation stages. X-ray diffraction methods for detection of fatigue damage prior to microcracking have been investigated since the 1930's [Regler, 1937; Regler, 1939]. In these tests, fatigue damage was found to be related to diffraction line broadening. More recently Taira [1966], Kramer [1974] and Weiss and Oshida [1984] have further developed the X-ray diffraction method. They proposed a self-referencing system for characterization of damage, namely the ratio of dislocation densities as measured 150 micrometers below the surface to that measured 10–50 micrometers below the surface. The data obtained to date suggest that in high strength aluminum alloys the probability of fatigue failure is zero for dislocation density ratios of 0.6 or below. However, it is generally impractical to make such measurements in the field.

Electrical resistivity also provides a potential indication of cumulative fatigue damage. This is supported by theory, since an increase in dislocation density results in an increase in electrical resistivity. Estimates suggest that, in the case of aluminum, depending on the increase in the density of dislocations in the fatigue-damage zone, the resistivity in the fatigue-affected region may increase by up to 1% prior to formation of microcracks. These estimates are based on dislocation densities in the fatigue-damage zone up to between $2(10^{11}$ cm$^{-2}$ to $10^{12}$ cm$^{-2}$ and a resistivity factor of $3.3(10^{-19}$ ((cm$^3$ [Friedel, 1964].

SUMMARY OF THE INVENTION

Aspects of the inventions described herein involve novel inductive sensors for the measurement of the near surface properties of conducting and magnetic materials. These sensors use novel winding geometries that promote accurate modeling of the response, eliminate many of the undesired behavior in the response of the sensing elements in existing sensors, provide increased depth of sensitivity by eliminating the coupling of spatial magnetic field modes that do not penetrate deep into the material under test (MUT), and provide enhanced sensitivity for crack detection, localization, crack orientation, and length characterization. The focus is specifically on material characterization and also the detection and monitoring of precrack fatigue damage, as well as detection and monitoring of cracks, and other material degradation from testing or service exposure.

Methods are described for forming eddy current sensors having primary windings for imposing a spatially periodic magnetic field into a test material. In one embodiment, the primary winding incorporates parallel extended winding segments formed by adjacent extended portions of individual drive coils. The drive coils are configured so that the current passing through adjacent extended winding segments is in a common direction and a spatially periodic magnetic field is imposed in the MUT. In another embodiment a single meandering conductor having extended portions in one plane is connected in series to another meandering conductor in a second plane. The conducting meanders are spatially offset from one another so that the current passing through adjacent extended winding segments is again in a common direction.

For sensing the response of the MUT to the periodic magnetic field, sensing elements are located within the primary winding. In one embodiment, the sensing elements have extended portions parallel to the extended portions of the primary winding and link incremental areas of magnetic flux within each half meander. The sensing elements in every other half-wavelength are connected together in series while the sensing elements in adjacent half wavelengths are spatially offset, parallel to the extended portions of the primary. The sensor can be scanned across the surface of the MUT to detect flaws or the sensor can be mounted on a part for detecting and determining the location of a flaw. Preferably, the longest dimension of the flaw will be substantially perpendicular to the extended portions of the primary winding.

Methods are also described for forming circular eddy current sensors having primary windings for imposing a spatially periodic magnetic field into a test material. The spatial pattern can be created from a plurality of concentric circular segments, where current flow through these segments creates a substantially circularly symmetric magnetic field that is periodic in the radial direction. The response of the MUT to the magnetic field is detected with one or more sensing elements placed between each concentric loop.

The extended portions of each sensing element are concentric with the concentric circular segments of the primary winding. The sensing elements may also be in a different plane than the primary winding. These windings may also form a substantially closed loop other than as a circle to follow a contour in the material under test.

The sensing elements can be distributed throughout the primary winding meanders. In one embodiment, a single sensing element is placed within each half wavelength of the primary winding. Separate output connections can be made to each sensing element, to create a sensor array. The sensing elements can be connected together to provide common output signals. In another embodiment, the sensing elements can link areas of incremental flux along the circumference of the primary winding segments. The sensing elements can have the same angular dimensions and, in every other half wavelength can be connected together in series to provide a common output. These are examples of circular spatially periodic field eddy-current sensors. These circular sensors can be used in either a surface mounted or scanning mode.

Another embodiment of an imaging sensor includes a primary winding of parallel extended winding segments that impose a spatially periodic magnetic field, with at least two periods, in a test substrate when driven by electric current. The array of sensing windings for sensing the response of the MUT includes at least two of the sensing windings in different half-wavelengths of the primary winding. These sensing windings link incremental areas of the magnetic flux and are offset along the length of the parallel winding segment to provide material response measurements over different locations when the circuit is scanned over the test material in a direction perpendicular to the extended winding segments. To minimize unmodeled effects on the response, extra conductors can be placed at the ends of the sensing elements and within the endmost primary winding meanders, and the sensing elements can be spaced at least a half-wavelength from the ends of the primary winding. In addition the distance from the sensing elements to the ends of the primary winding can be kept constant as the offset spacing between sensing elements within a single meander is varied.

An image of the material properties can be obtained when scanning the sensor in a direction perpendicular to the extended portions of the primary winding. The sensing elements can provide absolute or differential responses, which can provide a difference in MUT properties parallel to, perpendicular to, or at an intermediate angle to the extended portions of the primary winding.

The spatially periodic sensors can be fabricated onto flexible, conformable substrates for the inspection of curved parts. Alternatively, the sensors can be mounted on hard flat or curved substrates for non-contact scanning. Protective or sacrificial coatings can also be used to cover the sensor.

The sensors can be mounted against article surfaces for the detection of flaws. The nominal operating point can be varied to calibrate the sensor or provide additional information for the property measurement. For example, the sensor lift-off, the MUT temperature, and the MUT permeability can be varied. Measurement grids or databases can be used to determine the electrical and geometric properties of interest at the location measured by each sensing element. The electrical or geometric properties can also be correlated to other properties of interest for the MUT, such as crack size or depth. Multiple frequency measurements can also be performed to determine property variations with depth from the surface of the MUT.

In one embodiment, damage near fasteners can be monitored with spatially periodic field eddy-current sensors. The sensor should be mounted near the fastener so that damage in the MUT can be detected through changes in the electrical properties measured with the sensor. The sensor can be mounted beneath the fastener head, between structural layers attached by the fastener, or at both ends of the fastener. The damage may be in the form of a crack. Circular spatially periodic sensors having hollow center regions can surround fasteners to detect and locate damage that may emanate radially. Mounted on, or within a cylindrical support material in the form of a washer facilitates mounting under a fastener head. The support material may also support compressive loads. The damage from nearby fasteners can be monitored simultaneously with multiple sensors. Each sensor can have a single, absolute output, or pairs of sensor responses can be used to provide differential responses. Similarly, for multiple sensors, the drive conductors may be connected with a common drive signal or the sense conductors may be connected together for a common output connection.

Methods are also described for creating databases of measurement responses for multiple layer sensors and using these databases for converting sensor responses into properties of the MUT. The responses can be determined from analytical, finite difference, or finite element models.

Capabilities for monitoring fatigue damage as it occurs on test articles also provide novel methods for fabricating fatigue standards. Attaching an electromagnetic sensor that provides an absolute measurement of the electrical properties during mechanical loading or fatigue testing allows the material condition to be monitored as the damage occurs. Monitoring of the changes in the electrical properties then allow for the load to be removed at prescribed levels of damage. The damage can take the form of a fatigue crack or pre-crack damage. Once the crack has formed, the sensor can be used to monitor the change in crack length with the number of fatigue cycles. Multiple frequency measurements can provide a measure of crack depth. These changes in material properties can be monitored with multiple sensors to cover several inspection areas and create spatial images of the damage. In one embodiment the sensor is a spatially periodic field eddy current sensor and the MUT is a metal. Alternatively, the sensor could be a dielectrometer and the MUT a dielectric material or composite. In another embodiment either eddy current sensors or dielectrometers can be mounted under patches or bonded repairs.

For the fabrication of fatigue standards, the geometry of the fatigue articles can be altered to shape the stress distribution so that the fatigue damage initiates underneath the sensor. This can be accomplished by thinning the center section of typical dogbone specimens, by providing reinforcement ribs on the edges of the specimen to prevent edge cracks from forming, and by providing radius cutouts on the sides of the thinned center section.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 19 shows an engineering drawing for a fatigue specimen having a reduced thickness center section and symmetrical radius cutouts on both sides of the reduced thickness area.

DETAILED DESCRIPTION OF THE INVENTION

Figure 1:
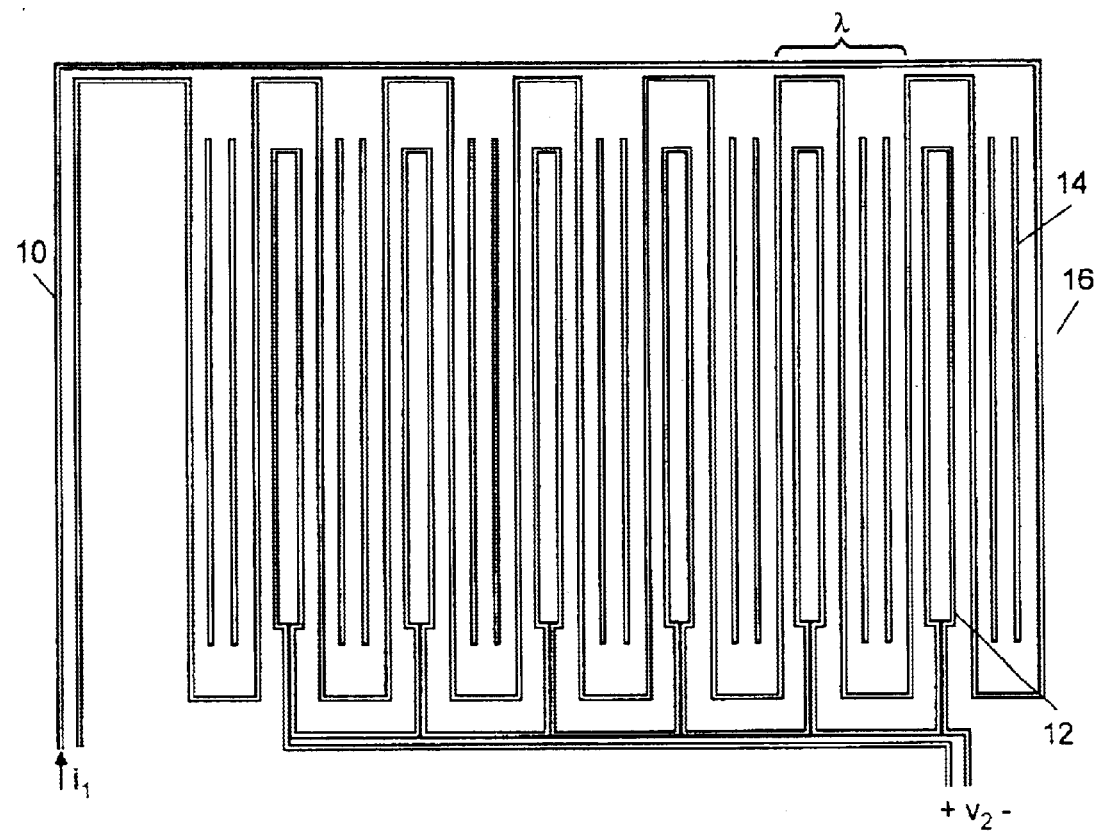
FIG. 1 is a plan view of a Meandering Winding Magnetometer sensor.

A description of preferred embodiments of the invention follows. To safely support life extension for aging structures and to reduce weight and maintenance/inspection costs for new structures requires both rapid and cost effective inspection capabilities. In particular, continuous monitoring of crack initiation and growth requires the permanent mounting of sensors to the component being monitored and severely limits the usefulness of calibration or reference standards, especially when placed in difficult-to-access locations on aging or new structures.

Permanent and surface mounting of conventional eddy-current sensors is not performed. One reason for this is the calibration requirements for the measurements and another is the variability between probes. Conventional eddy-current techniques require varying the proximity of the sensor (or lift-off) to the test material or reference part by rocking the sensor back and forth or scanning across a surface to configure the equipment settings and display. For example, for crack detection the lift-off variations is generally displayed as a horizontal line, running from right to left, so that cracks or other material property variations appear on the vertical axis. Affixing or mounting the sensors against a test surface precludes this calibration routine. The probe-to-probe variability of conventional eddy-current sensors prevents calibrating with one sensor and then reconnecting the instrumentation to a second (e.g., mounted) sensor for the test material measurements. Measured signal responses from nominally identical probes having inductance variations less than 2% have signal variations greater than 35% [Auld, 1999]. These shortcomings are overcome with spatially periodic field eddy-current sensors, as described herein, that provide absolute property measurements and are reproduced reliably using micro-fabrication techniques. Calibrations can also be performed with duplicate spatially periodic field sensors using the response in air or on reference parts prior to making the connection with the surface mounted sensor.

The capability to characterize fatigue damage in structural materials, along with the continuous monitoring of crack initiation and growth, has been demonstrated. A novel eddy-current sensor suitable for these measurements, the Meandering Winding Magnetometer Array (MWM™-Array), is described in U.S. Pat. Nos. 5,015,951, 5,453,689, and 5,793,206. The MWM is a "planar," conformable eddy-current sensor that was designed to support quantitative and autonomous data interpretation methods. These methods, called grid measurement methods, permit crack detection on curved surfaces without the use of crack standards, and provide quantitative images of absolute electrical properties (conductivity and permeability) and coating thickness without requiring field reference standards (i.e., calibration is performed in "air," away from conducting surfaces). The use of the MWM-Array for fatigue mapping and on-line fatigue monitoring has also been described [Goldfine, 1998 NASA]. This inspection capability is suitable for on-line fatigue tests for coupons and complex components, as well as for monitoring of difficult-to-access locations on both military and commercial aircraft.

FIG. 1 to FIG. 12 illustrate the standard geometry for an MWM sensor and its initial application to fatigue damage measurements. FIG. 1 illustrates the basic geometry of the MWM sensor 16, detailed descriptions of which are given in U.S. Pat. Nos. 5,015,951, 5,453,689, and 5,793,206. The sensor includes a meandering primary winding 10 having extended portions for creating the magnetic field and meandering secondary windings 12 within the primary winding for sensing the response. The primary winding is fabricated in a square wave pattern with the dimension of the spatial periodicity termed the spatial wavelength. A current $i_1$, is applied to the primary winding and a voltage $v_2$ is measured at the terminals of the secondary windings. The secondary elements are pulled back from the connecting portions of the primary winding to minimize end effect coupling of the magnetic field and a second set of secondary windings can meander on the opposite side of the primary or dummy elements 14 can be placed between the meanders of the primary to maintain the symmetry of the magnetic field, as described in pending application Ser. No. 09/182,693. The magnetic vector potential produced by the current in the primary can be accurately modeled as a Fourier series summation of spatial sinusoids, with the dominant mode having the spatial wavelength. For an MWM-Array, the responses from individual or combinations of the secondary windings can be used to provide a plurality of sense signals for a single primary winding construct as described in U.S. Pat. No. 5,793,206.

The MWM structure can be produced using micro-fabrication techniques typically employed in integrated circuit and flexible circuit manufacture. This results in highly reliable and highly repeatable (i.e., essentially identical) sensors, which has inherent advantages over the coils used in conventional eddy-current sensors. As indicated by Auld and Moulder, for conventional eddy-current sensors "nominally identical probes have been found to give signals that differ by as much as 35%, even though the probe inductances were identical to better than 2%" [Auld, 1999]. This lack of reproducibility with conventional coils introduces severe requirements for calibration of the sensors (e.g., matched sensor/calibration block sets). In contrast, duplicate MWM sensor tips have nearly identical magnetic field distributions around the windings as standard micro-fabrication (etching) techniques have both high spatial reproducibility and resolution. As the sensor was also designed to produce a spatially periodic magnetic field in the material under test (MUT), the sensor response can be accurately modeled which dramatically reduces calibration requirements. For example, in some situations an "air calibration" can be used to measure an absolute electrical conductivity without calibration standards, which makes the MWM sensor geometry well-suited to surface mounted or embedded applications where calibration requirements will be necessarily relaxed.

An efficient method for converting the response of the MWM sensor into material or geometric properties is to use grid measurement methods. These methods map the magnitude and phase of the sensor impedance into the properties to be determined and provide for a real-time measurement capability. The measurement grids are two-dimensional databases that can be visualized as "grids" that relate two measured parameters to two unknowns, such as the conductivity and lift-off (where lift-off is defined as the proximity of the MUT to the plane of the MWM windings). For the characterization of coatings or surface layer properties, three-dimensional versions of the measurement grids can be used. Alternatively, the surface layer parameters can be determined from numerical algorithms that minimize the least-squares error between the measurements and the predicted responses from the sensor.

An advantage of the measurement grid method is that it allows for real-time measurements of the absolute electrical properties of the material. The database of the sensor responses can be generated prior to the data acquisition on the part itself, so that only table lookup operation, which is relatively fast, needs to be performed. Furthermore, grids can be generated for the individual elements in an array so that each individual element can be lift-off compensated to provide absolute property measurements, such as the electrical conductivity. This again reduces the need for extensive calibration standards. In contrast, conventional eddy-current methods that use empirical correlation tables that relate the amplitude and phase of a lift-off compensated signal to parameters or properties of interest, such as crack size or hardness, require extensive calibrations and instrument preparation.

Figure 2:
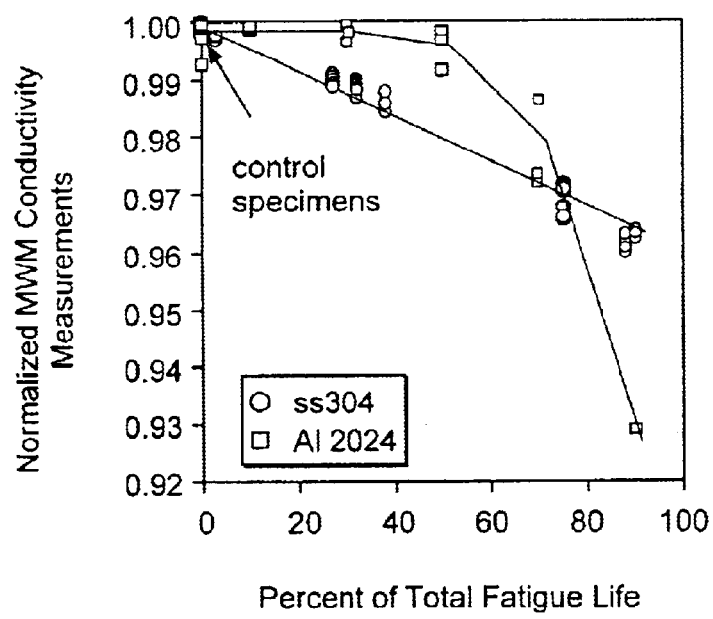
FIG. 2 is an illustration of the MWM measured conductivity dependence on the percent of total fatigue life for Type 304 stainless steel and aluminum alloy 2024.
Figure 3A:
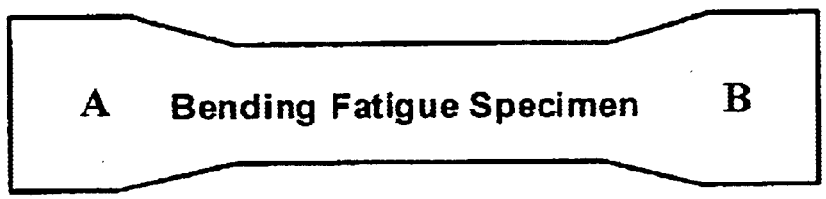
FIG. 3 shows MWM measurement scans along aluminum alloy 2024 hour-glass specimens before and after fatigue testing to various percentages of total fatigue life.
Figure 3B:
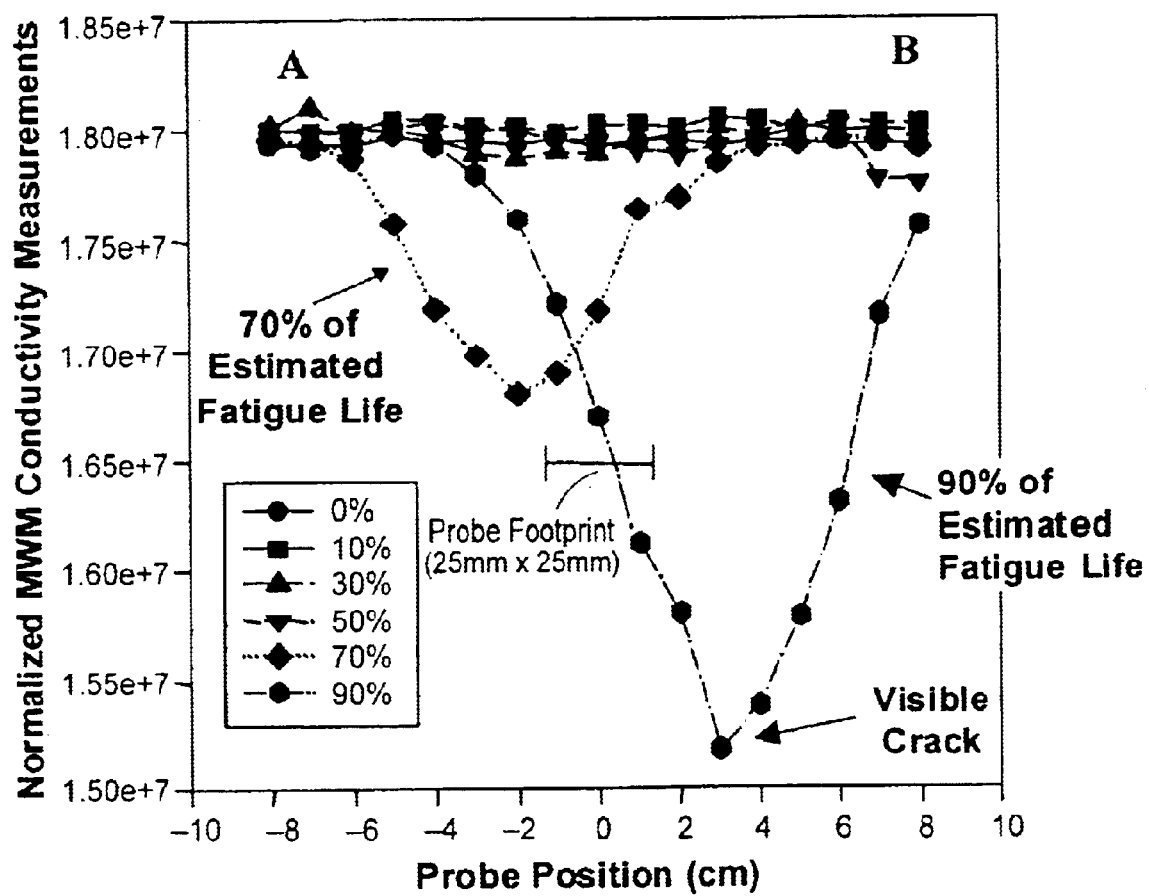

FIG. 2 and FIG. 3 illustrate the capability of the MWM sensor to provide a measure of fatigue damage prior to the formation of cracks detectable by traditional nondestructive inspection methods. Hourglass and "dog-bone" shaped specimens were exposed to varying fractions of their fatigue life at a known alternating stress level. The MWM conductivity measured with conductivity/lift-off grids for stainless steel and aluminum alloys correlates with fatigue life fraction, as shown in FIG. 2, and reflects cumulative fatigue damage. For Al 2024, the MWM measurements detect fatigue damage at less than 50 percent of the specimen's fatigue life. For Type 304 stainless steel specimens, the decrease in effective conductivity starts much earlier (which can be attributed to a change in magnetic permeability due to a gradual formation of martensite of deformation) and continues to decrease, almost linearly, with increasing fatigue life fraction, as defined by the cycle ratio $N/N_F$, i.e., (cumulative cycles)/(cycles to failure). The nonlinearity of the damage with cumulative fatigue life for Al 2024 in a typical bending fatigue coupon is well depicted by MWM measurements illustrated in both FIG. 2 and FIG. 3.

FIG. 3 shows the ability of an MWM sensor to detect the spatial distribution of fatigue damage as the sensor was scanned along the length of coupons exposed to fully reversed bending. These measurements reveal a pattern of fatigue damage focused near the dogbone specimen transition region for both the 70 and the 90 percent cumulative life specimens. The minimum conductivity at the 3 cm point on the specimen that reached 90 percent of its fatigue life corresponds precisely with the location of a visible crack. These measurements were taken with a sensor having a footprint of 1 inch by 1 inch. The presence of a damaged region in the vicinity of the crack is indicated by the depressed conductivity near the crack, even when the crack is not under the footprint of the sensor. Thus, bending fatigue produces an area damaged by microcracks prior to the formation of a dominant macrocrack, and that damaged area is detectable as a significant reduction in the MWM measured conductivity. Photomicrographs have shown that clusters of microcracks, 0.001 to 0.003 inches deep, begin to form at this stage. Although detectable with the MWM, these microcrack clusters, termed wide-spread fatigue damage (WFD), were not detectable with liquid penetrant testing, except at the very edge of the 90 percent life specimen. This same behavior has been observed for MWM measurements on military and commercial aircraft structural members.

Figure 4A:
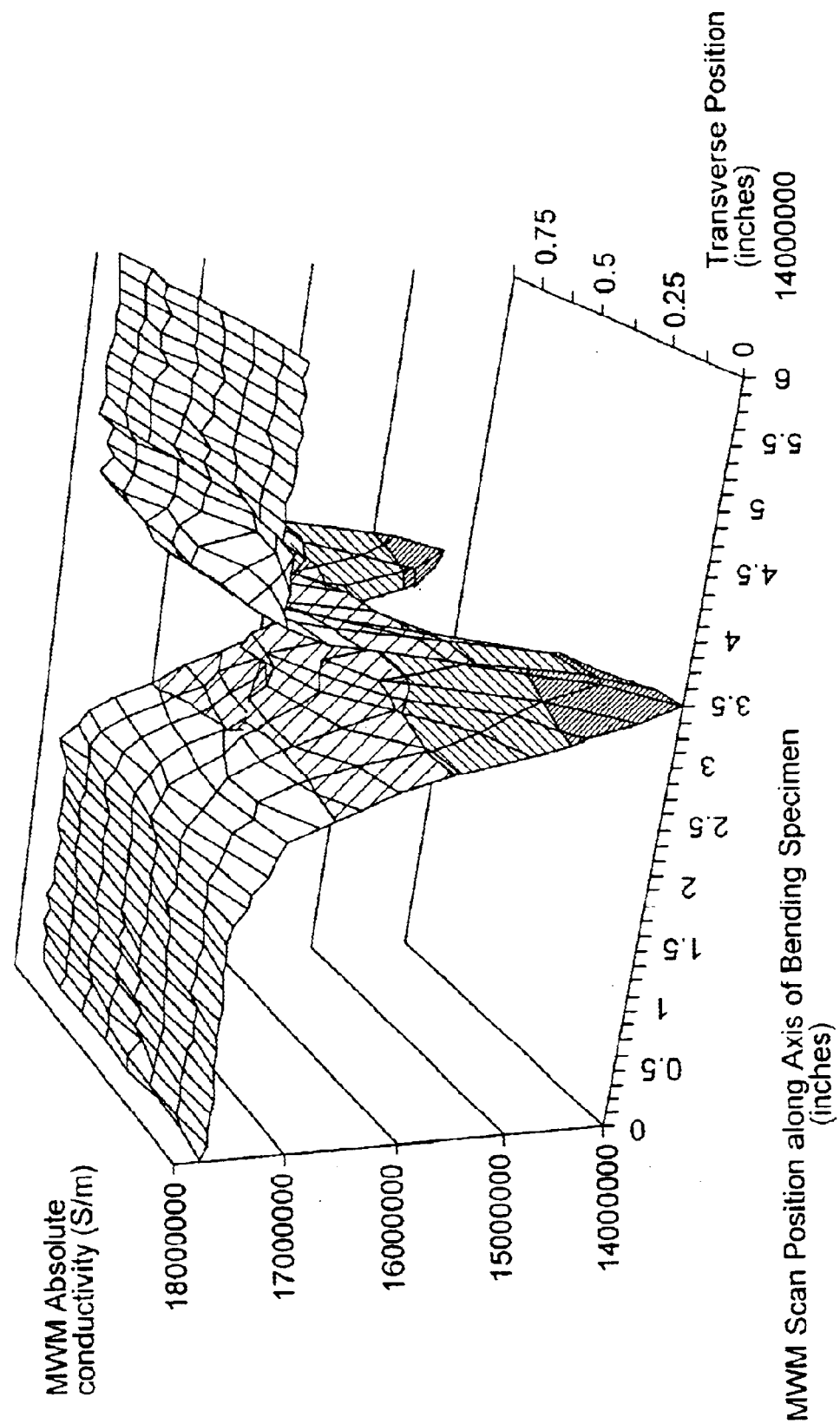
FIG. 4 is an illustration of two-dimensional MWM measured absolute conductivity scans along the surface of a aluminum alloy 2024 bending fatigue coupon with extended portions of the windings (a) perpendicular to macrocrack orientation (i.e., perpendicular to the bending moment axis) and (b) parallel to macrocrack orientation.
Figure 4B:
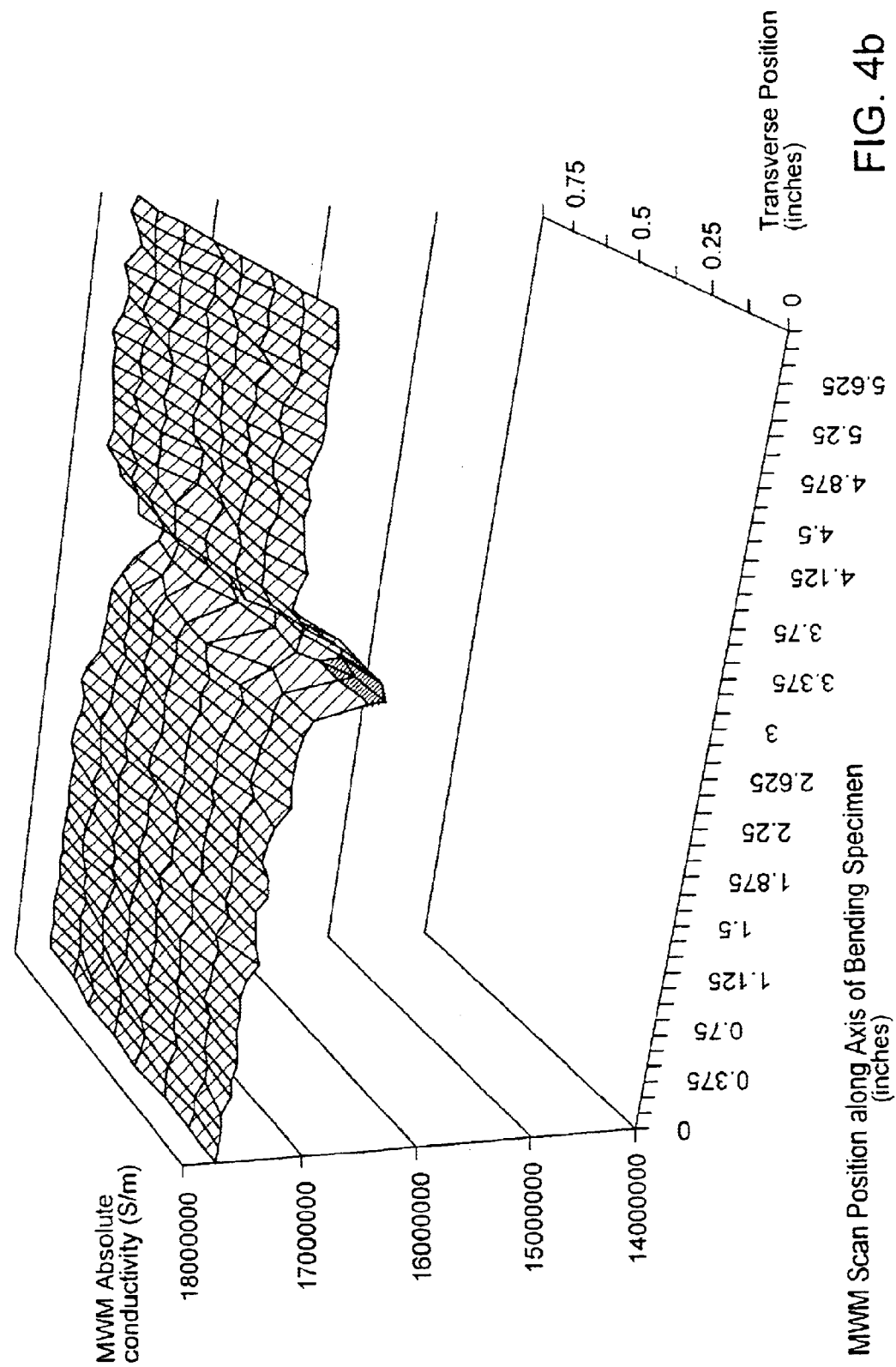

FIGS. 4a and 4b provide two-dimensional images of the measured conductivity over the 90 percent life fatigue specimen with the MWM in two different orientations. In this case, the MWM footprint was 0.5 inches by 0.5 inches. When the extended portions of the MWM winding segments are oriented perpendicular to the cracks, the MWM has maximum sensitivity to the macrocrack and microcrack clusters (FIG. 4a). When the extended portions of the MWM are oriented parallel to the crack, the MWM has minimum sensitivity to the macrocrack and microcrack clusters (FIG. 4b). The directional dependence of the sensor response in the fatigue damaged area adjacent to the macrocrack indicates that the microcracks that form at early stages of fatigue damage are highly directional and, in this case, are aligned with the bending moment axis. Similar measurements on complex aircraft structural members have shown similar behavior at early stages of fatigue damage, before detectable macrocracks have formed. Note that the microcrack density and size increases are indicated by a larger reduction in the MWM absolute conductivity measurements. Thus, as expected, the microcrack size and density increase near the coupon edges and are lower at the center.

Figure 5A:
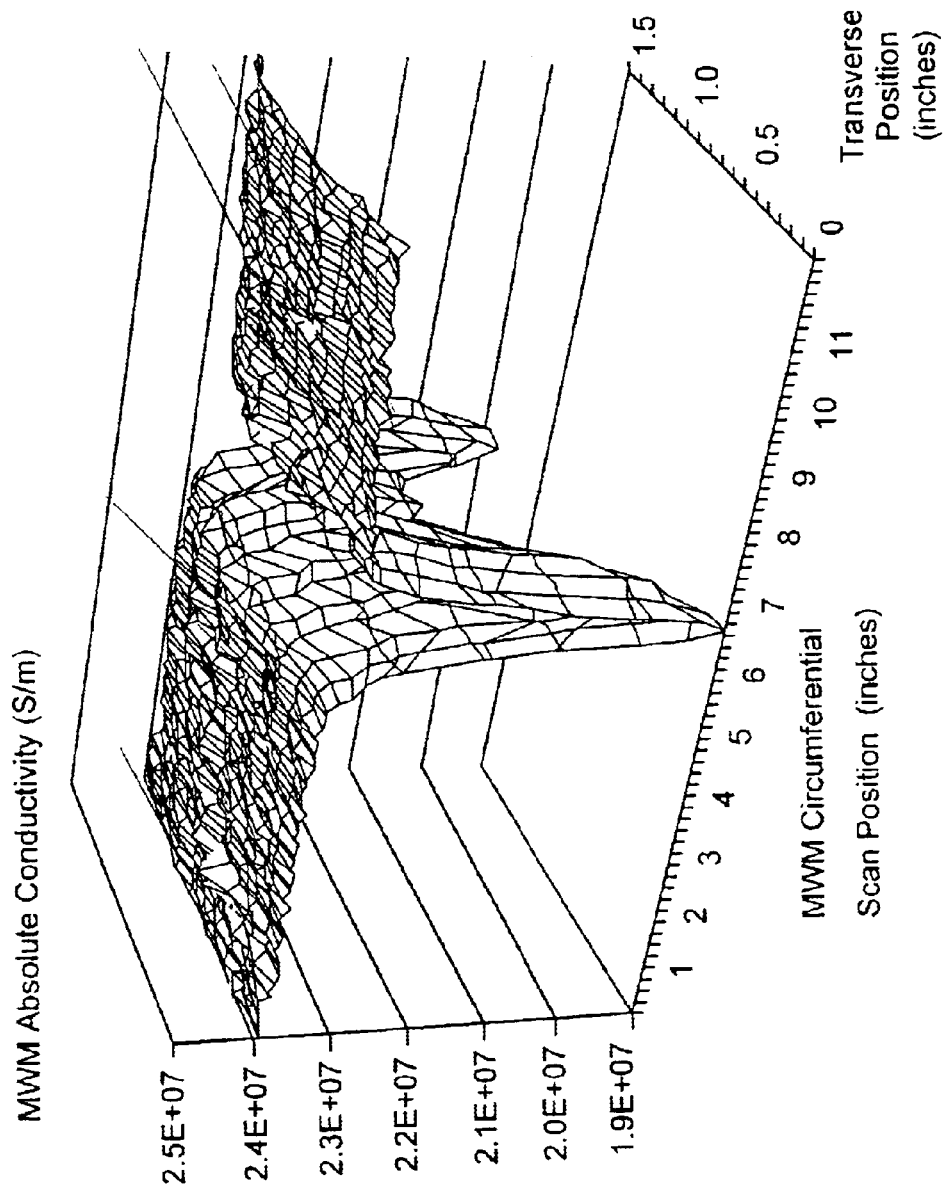
FIG. 5 is an illustration of two-dimensional MWM measured absolute conductivity scans along the surface of a military aircraft component with windings oriented (a) perpendicular and (b) parallel to the bending moment axis.
Figure 5B:
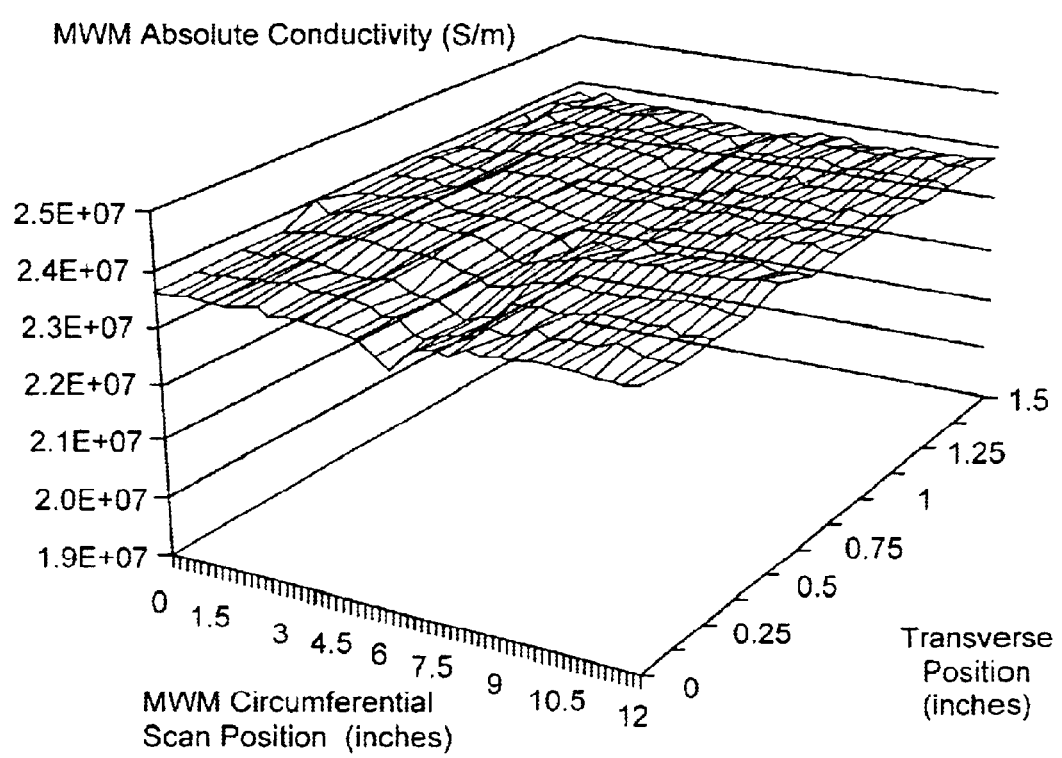

Similar two-dimensional images of the measured conductivity have been obtained on actual military components. FIGS 5a and 5b show the surface scan mapping of fatigue damage on a military aircraft bulkhead for MWM windings segments oriented both perpendicular and parallel to the bending moment axis. One portion of the bulkhead was found to contain a localized conductivity excursion characteristic of early stage fatigue microcracking. A conventional eddy-current inspection of this area found only discrete macrocracks. However, the width of the area of the MWM measured reduced conductivity beyond the macrocrack area indicates that there is a region of microcracking in addition to the discrete macrocracks.

Figure 6:
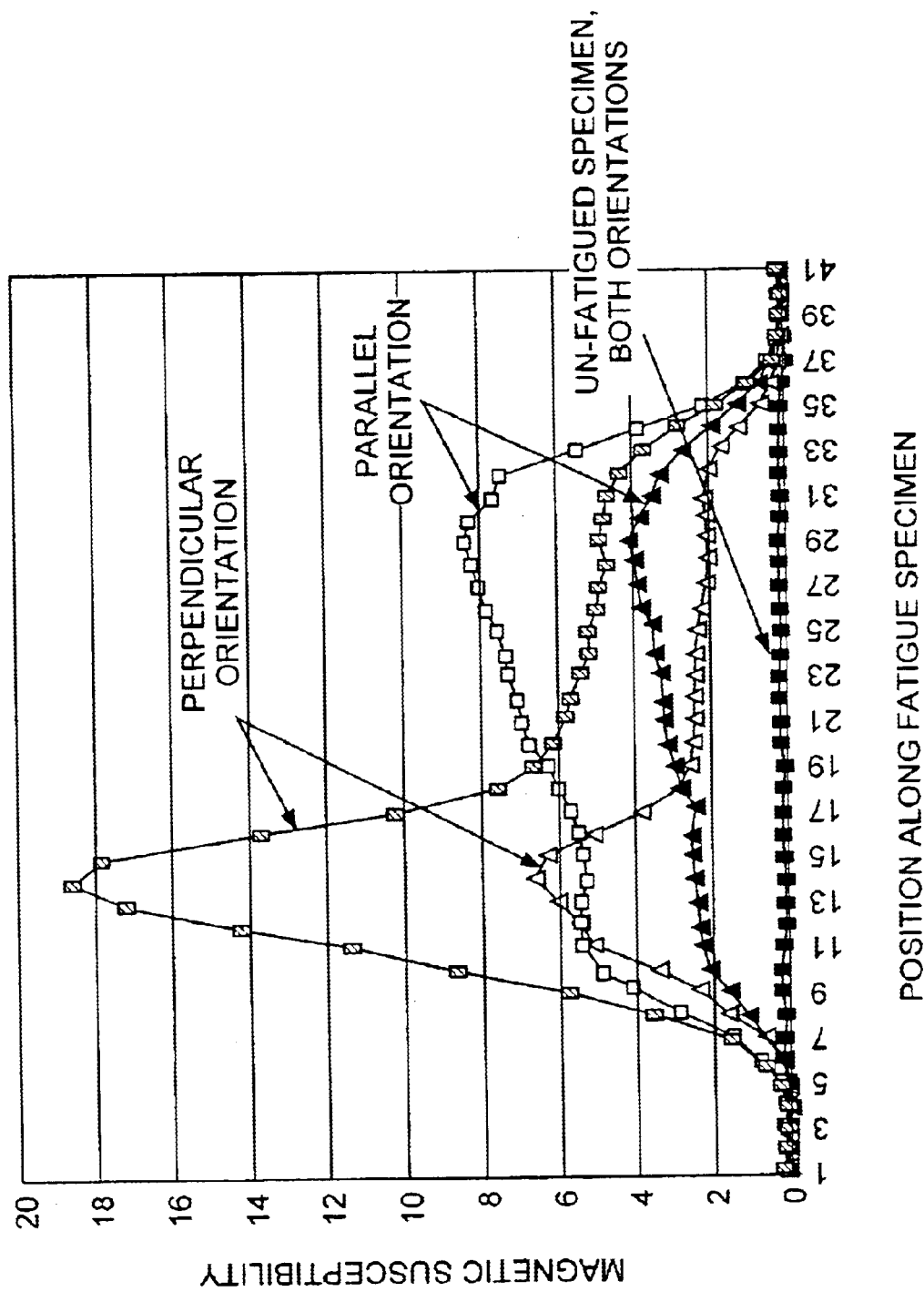
FIG. 6 shows scans of bi-directional magnetic permeability along two austenitic stainless steel specimens. One specimen was not fatigue tested and the other specimen was fatigue tested.

Fatigue damage can also create variations in the magnetic permeability, as indicated in FIG. 6 for two austenitic stainless steel specimens. One specimen was fatigue tested while the other was not. Surface scans with the MWM windings oriented perpendicular and parallel to the length of the specimens show a bi-directional magnetic permeability in the fatigued specimen. The magnetic susceptibility is largest in the loading direction as the fatigue alters the microstructure of the stainless steel, creating a magnetic phase such as martensite from the initially nonmagnetic material.

Figure 7A:
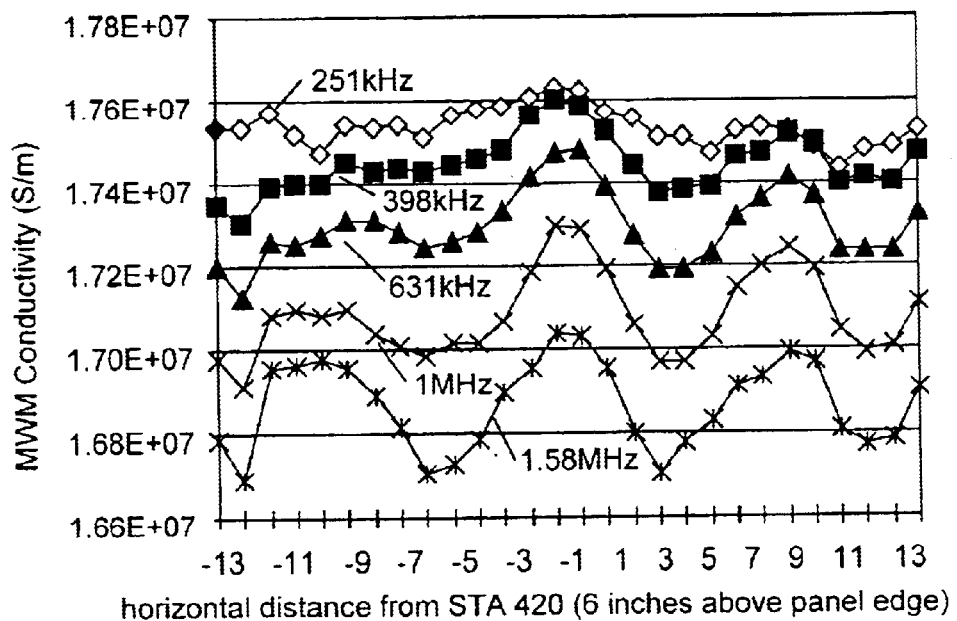
FIG. 7 is an illustration of multiple frequency measurements on a Boeing 737 fuselage as the MWM is scanned (a) horizontally above the lap joint but beneath the passenger windows and (b) vertically from a window to the lap joint.
Figure 7B:
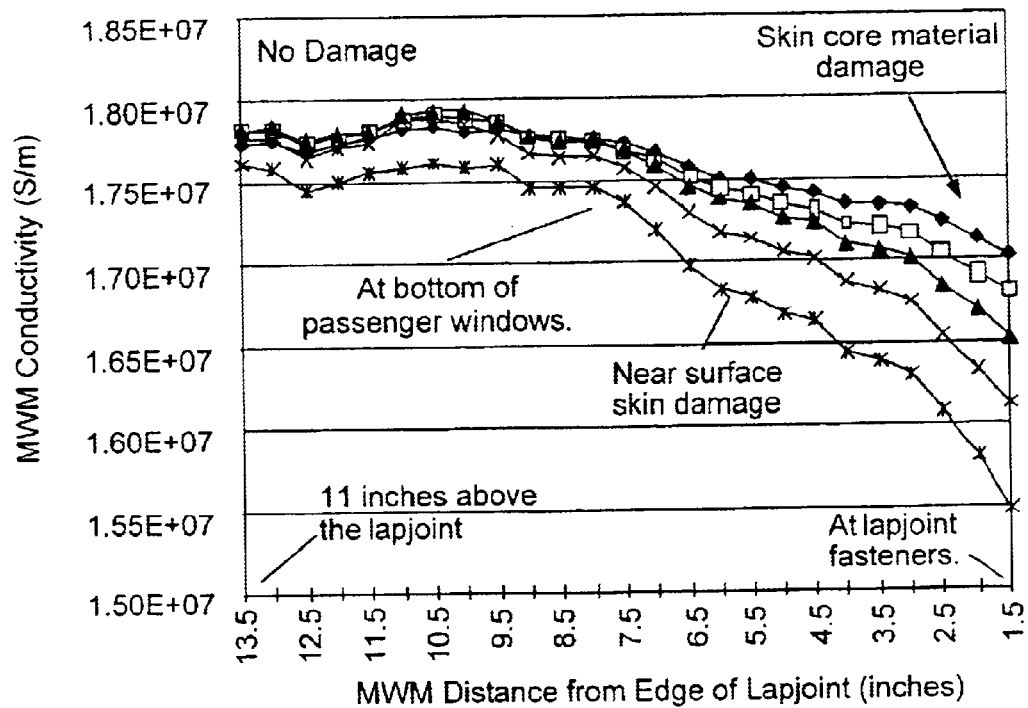

FIGS. 7a and 7b show the results of examinations of service exposed sections of a Boeing 737 fuselage. MWM measurements were made on the lap joint near the passenger windows and on the skin panels under the pilot window post. The MWM detected several areas with substantial conductivity variations that could be identified as areas of widespread fatigue damage, i.e., extensive fatigue microcracking. FIG. 7a shows a horizontal scan several inches above the top fastener row of the lap joint. The MWM measured conductivity has minima that correspond consistently with the vertical edge locations of the windows. Thus, substantial bending fatigue damage was detected by the MWM several inches above the lap joint fastener rows. The bending fatigue coupon data suggest that this region is beyond 60 percent of its fatigue life, although it probably does not contain macrocracks which would be detectable with conventional differential eddy-current methods or with liquid penetrant testing. FIG. 7a shows a vertical scan down the panel. The damage begins near the bottom of the windows and increases steadily, with the maximum damage occurring at the fasteners. A key observation from these measurements is that this damage is detectable more than six inches away from the fasteners. It was later verified that cracks near fasteners were correlated with regions of reduced conductivity found by the MWM several inches away from any fasteners. Five out of five locations in which macrocracks had been documented at fasteners had been in areas similar to those identified by the MWM detection of distributed damage away from the fasteners.

This ability to map the spatial extent of the wide area fatigue provides information that can be used to improve the selection of patch location and size, thereby potentially improving the reliability of the repairs and reducing follow-on maintenance costs. The MWM measured conductivity information may also be used to identify specific regions that require fastener inspections, as well as to support inspection, maintenance scheduling and redesign efforts. This is important because the locations of these areas are not always intuitive, since the structural response is affected by design features such as window edge stiffeners, lap joints, and doublers, and by maintenance features such as patches and repairs in sometimes unforeseen ways.

Figure 8A:
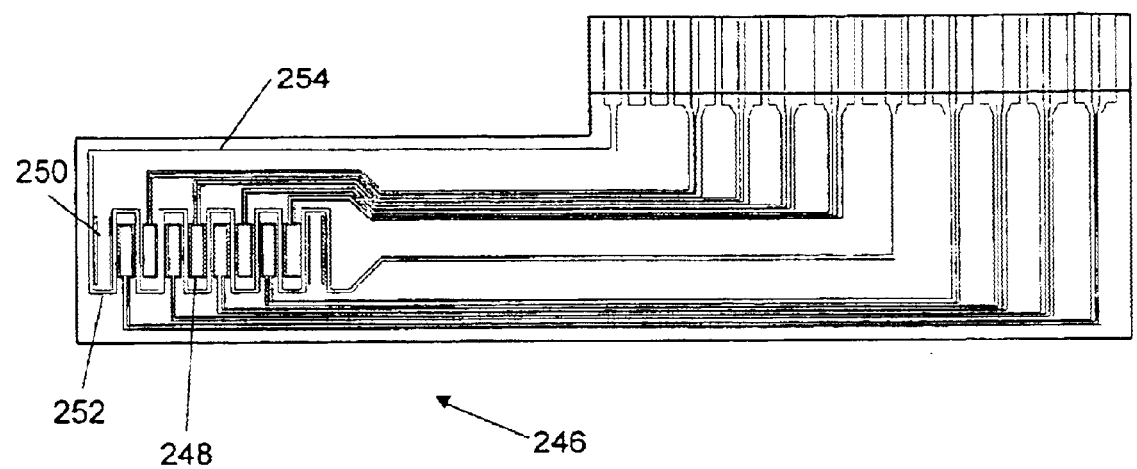
FIG. 8 is (a) a plan view of a sensing element and MWM-Array with one meandering primary winding and an array of secondary sensing elements with connections to each individual element and (b) an expanded view of the sensor windings.
Figure 8B:
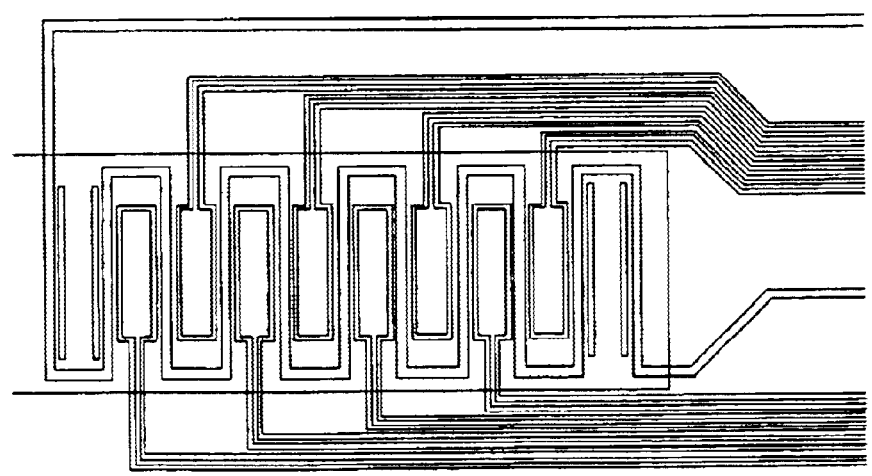

FIGS. 8a and 8b show expanded versions of an eight-element array. Connections are made to each of the individual secondary elements 248. For use with air calibration, dummy elements 250 are placed on the outside meanders of the primary 254. As described in patent application Ser. No. 09/182,693, the secondaries are set back from the primary winding connectors 252 and the gap between the leads to the secondary elements are minimized. This flexible array can be inserted into a hole within the gage section of a fatigue specimen to monitor crack initiation and initial crack propagation or placed flush against a surface to monitor crack propagation.

Figure 9:
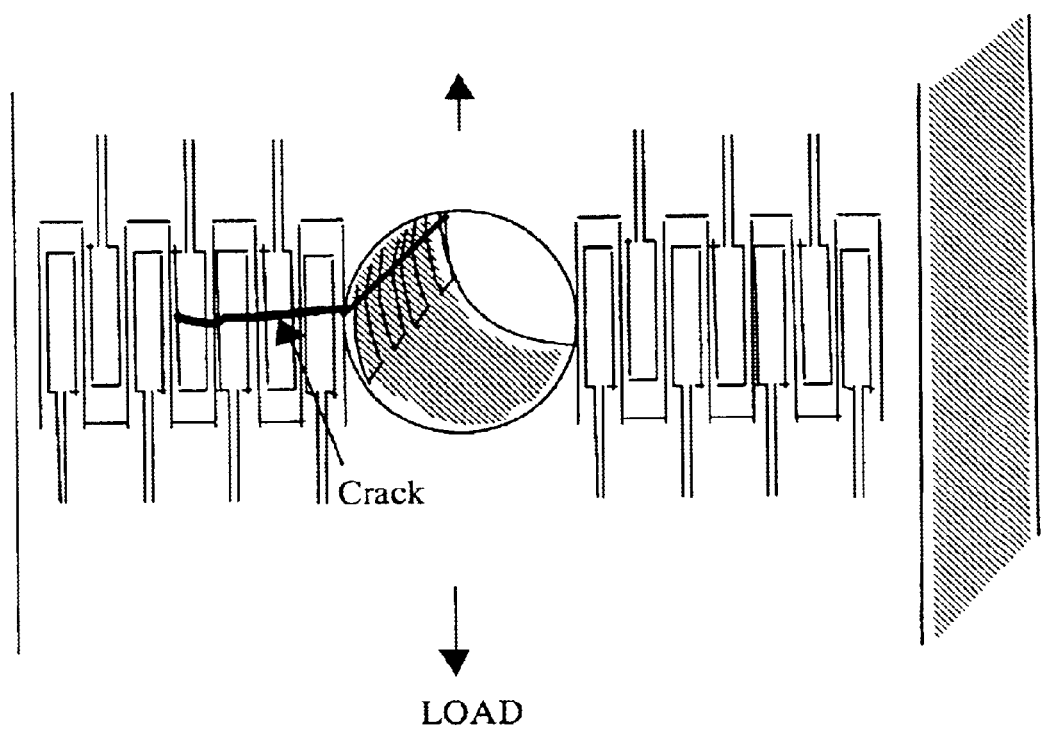
FIG. 9 shows an illustration of six MWM-Arrays mounted inside and on the surface of a fatigue test coupon.

FIG. 9 shows an example application of six MWM-Arrays from FIGS. 8a and 8b with two mounted inside a hole and four mounted on the adjacent flat side surfaces of a fatigue test coupon. The MWM-Arrays mounted within the hole can be used to detect shallow part-through wall cracks (e.g., tunneling cracks that have initiated inside the hole but have not propagated to the outside surface). The MWM-Arrays can also be placed around the circumference of a cylindrical or hyperbolical gage section. Multi-frequency MWM measurements can provide diagnostic information to monitor crack propagation in both length and depth directions. The MWM-Arrays on the sides are used once a "corner" or through-wall crack (i.e., one that has reached either or both outer surfaces), forms. The crack length can be inferred from the MWM measured effective conductivity since the MWM measured conductivity change correlates with crack length, as shown for example in FIG. 17, even for relatively short surface cracks and for cracks deeper than the MWM penetration depth. The correlation with length is expected to be even more robust for through-wall cracks so that a single sensing element MWM may be used for regions outside the hole as well. This type of application is suitable for monitoring crack propagation with fatigue cycles (da/dN) during complex component testing. For example, monitoring of wide areas (e.g. between skins) in an aircraft component may not be possible optically or with potential drop methods. This MWM capability can provide a new tool to demonstrate damage tolerance of structures and establish less burdensome inspection and retirement for time policies.

Figure 10:
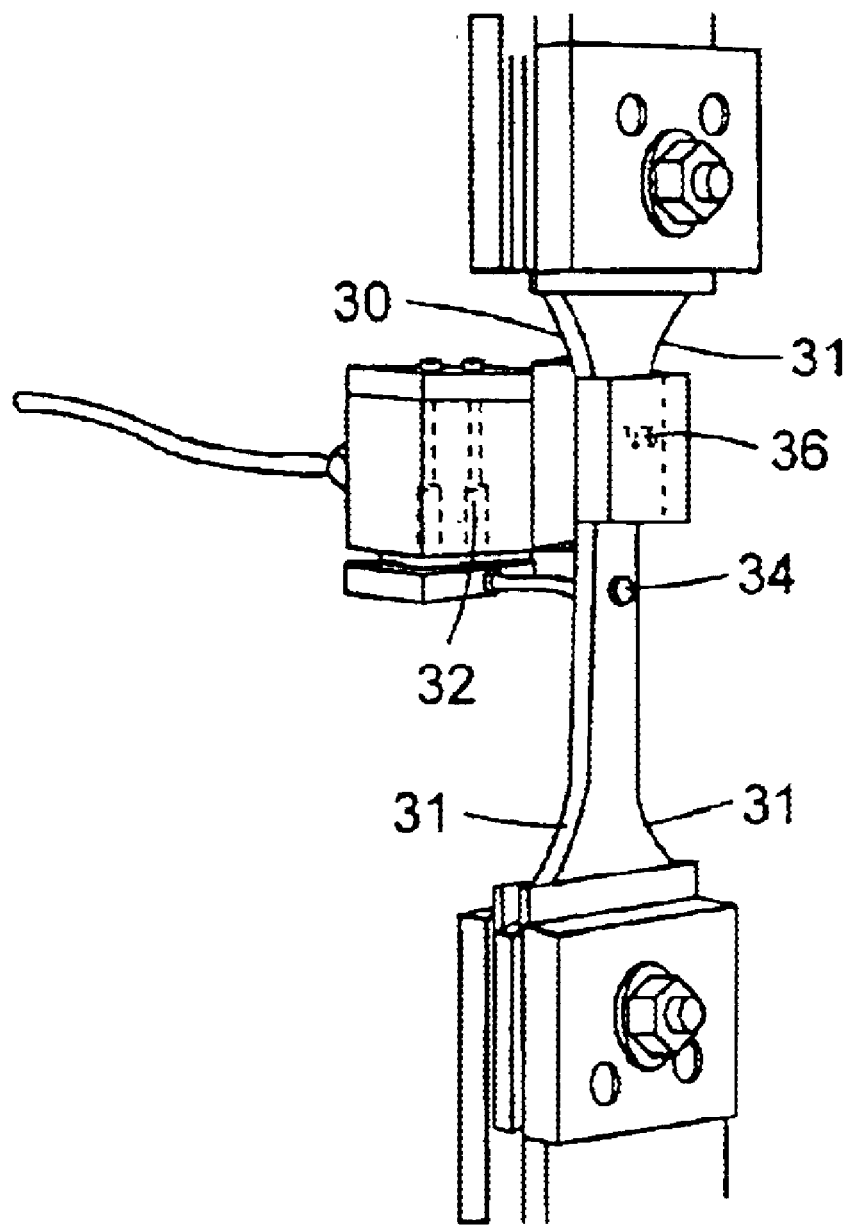
FIG. 10 shows an MWM-Array mounted inside a fatigue test coupon.

Surface mounted MWM-Arrays have also demonstrated an on-line capability to monitor cumulative fatigue damage during load cycling. FIG. 10 shows the placement of an MWM-Array, from FIGS. 8a and 8b, into a 0.25-inch diameter hole 34 located at the center of a 1-inch wide by 0.25-inch thick (25.4 mm wide by 6.35-mm thick) specimen 30 made of an aluminum (Al 2024-T351) alloy. The flat specimens with tangentially blended fillets 31 between the test section and the grip ends were tested under constant cyclic stress amplitude in tension loading. The central hole represents an elastic stress concentration factor of 2.4. The MWM-Array had eight sensing elements (1 mm by 2.5 mm in area) located at 1-mm increments along the array length in the periodic direction. Six of the eight elements were mounted in contact with the internal cylindrical surface of the hole while the two outermost elements were intentionally outside the hole. The fixture 36 holds the MWM-Array inside the hole and the probe electronics 32 for amplifying and multiplexing the measured signals to allow continuous monitoring throughout the test. Several specimens were run to failure to determine the response throughout the fatigue life, i.e., from crack initiation to failure, while fatigue tests of other specimens were stopped at various stages of crack initiation and propagation, as illustrated for example in FIGS. 11 through 15.

Figure 11A:
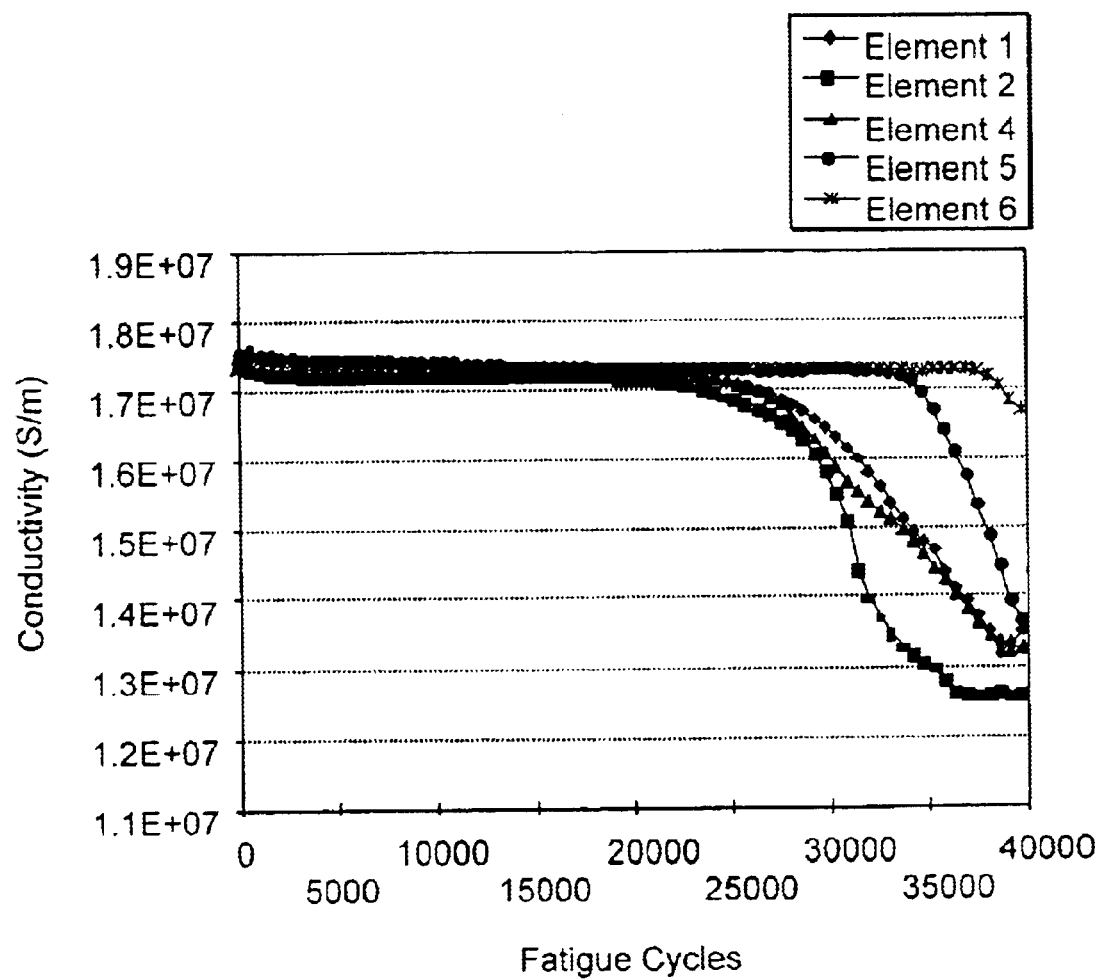
FIG. 11 shows an example of the MWM measured conductivity variation with fatigue level.
Figure 11B:
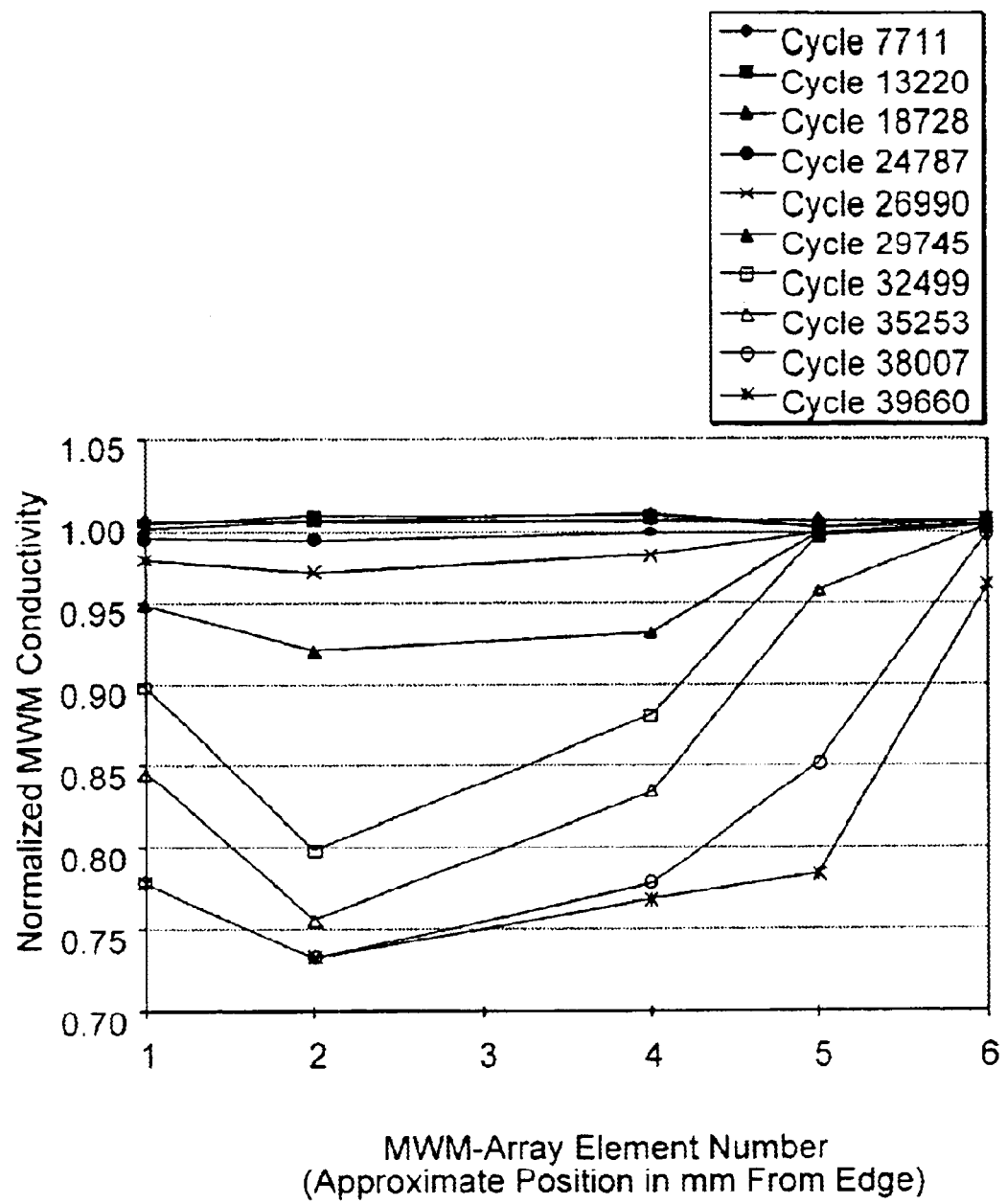

FIGS. 11a, 11b, 12a, and 12b show the MWM measurements during a fatigue test. The third element channel failed in this first test so the data for the third element is not provided. FIGS. 11a and 11b show the absolute electrical conductivity measurements for each element of the MWM-Array. FIG. 11a shows the conductivity as a function of the number of fatigue cycles for each element while FIG. 11b shows the conductivity as a function of the element position across the thickness of the drilled hole for several fatigue levels. The pronounced decrease in conductivity at around 25,000 cycles indicates crack initiation. The crack appears to initiate near Element 2, as this was the first element to exhibit a decrease in the conductivity. The crack then quickly propagates to the edge at Element 1 and then gradually propagates to the other edge and is detected by Element 6. This particular test was stopped when Element 6 began to detect the crack. Upon an examination with an optical microscope at magnification of 100 times, no crack was apparent on the outer surface near Element 6.

Figure 12A:
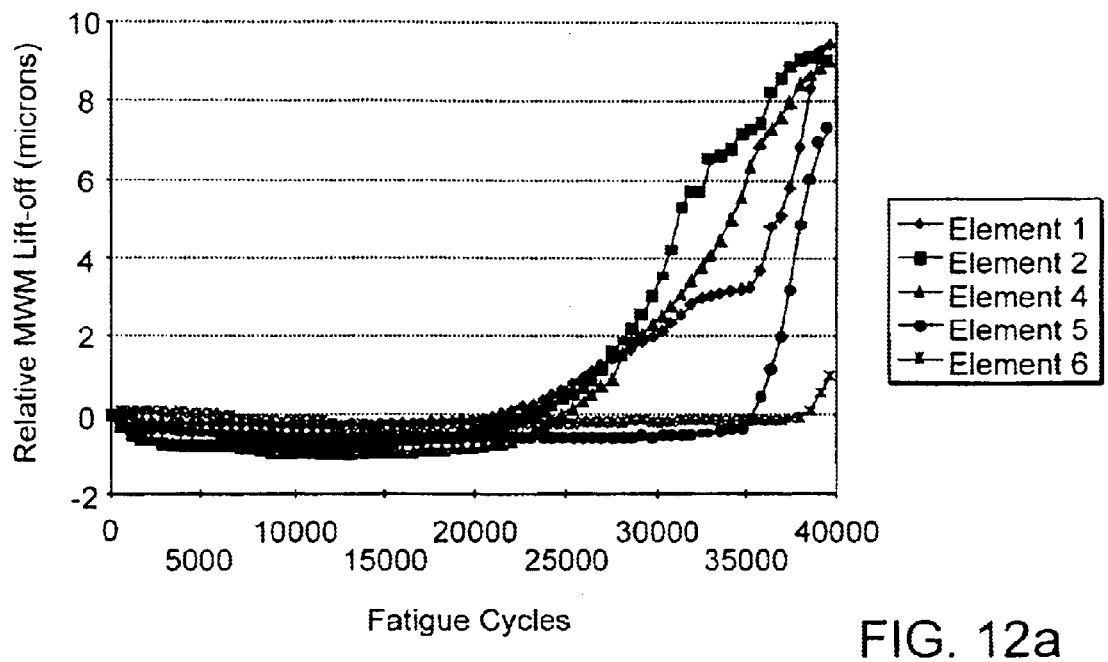
FIG. 12 shows an example of the MWM measured lift-off variation with fatigue level.
Figure 12B:
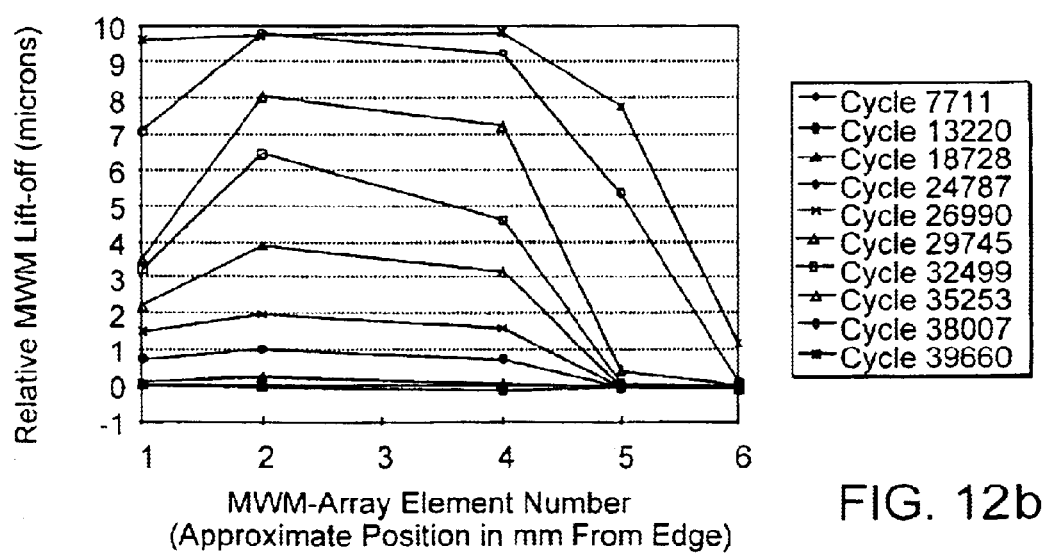

FIGS. 12a and 12b show the lift-off measurements for each element of the MWM-Array using a uniform property model. FIG. 12a shows the lift-off as a function of the number of fatigue cycles for each element while FIG. 12b shows the lift-off as a function of the element position across the length of the cylindrical hole for several fatigue levels. The initial decrease and leveling of the lift-off data during the initial testing (less than 15,000 cycles) illustrates the "settling" of the MWM as the sensor adjusts to the surface. The increase of the effective lift-off during later stage testing shows the effect of the opening of the crack. Although this lift-off data shows that the uniform property model can represent the crack, improved models of crack interactions with spatially periodic field sensors should enhance crack detection sensitivity and also provide depth measurements. Also, monitoring of "effective liftoff" signals using the MWM-Array for deep cracks (over 0.1 inches) provides information about the "compliance" of large cracks and may be useful for crack depth estimates.

Figure 13A:
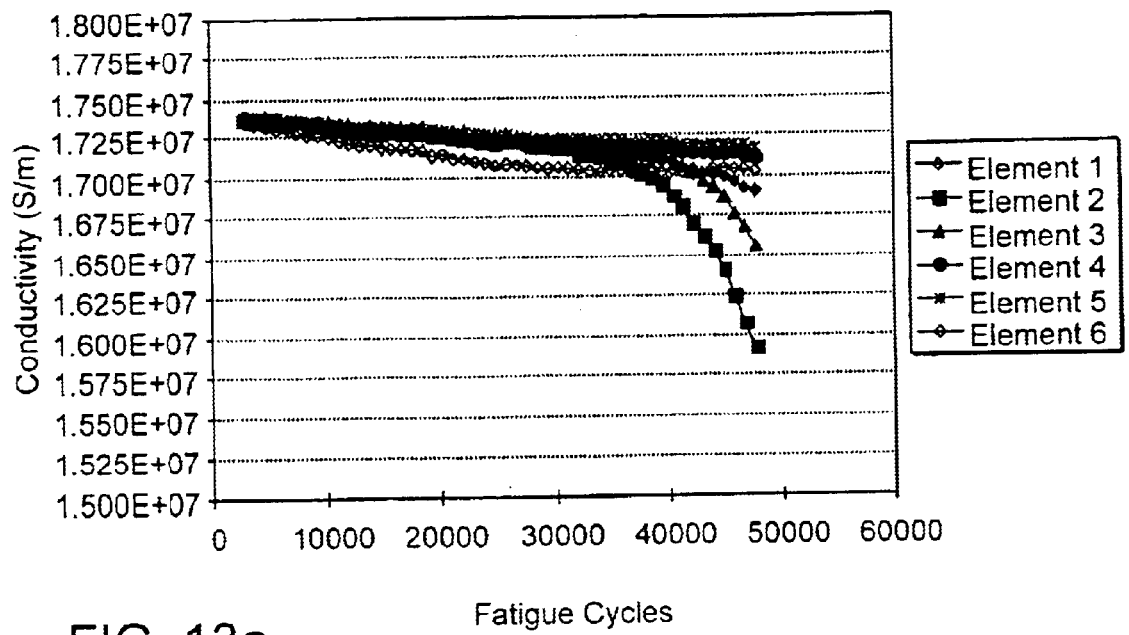
FIG. 13 shows an example of the MWM measured conductivity variation with early stage fatigue damage.
Figure 13B:
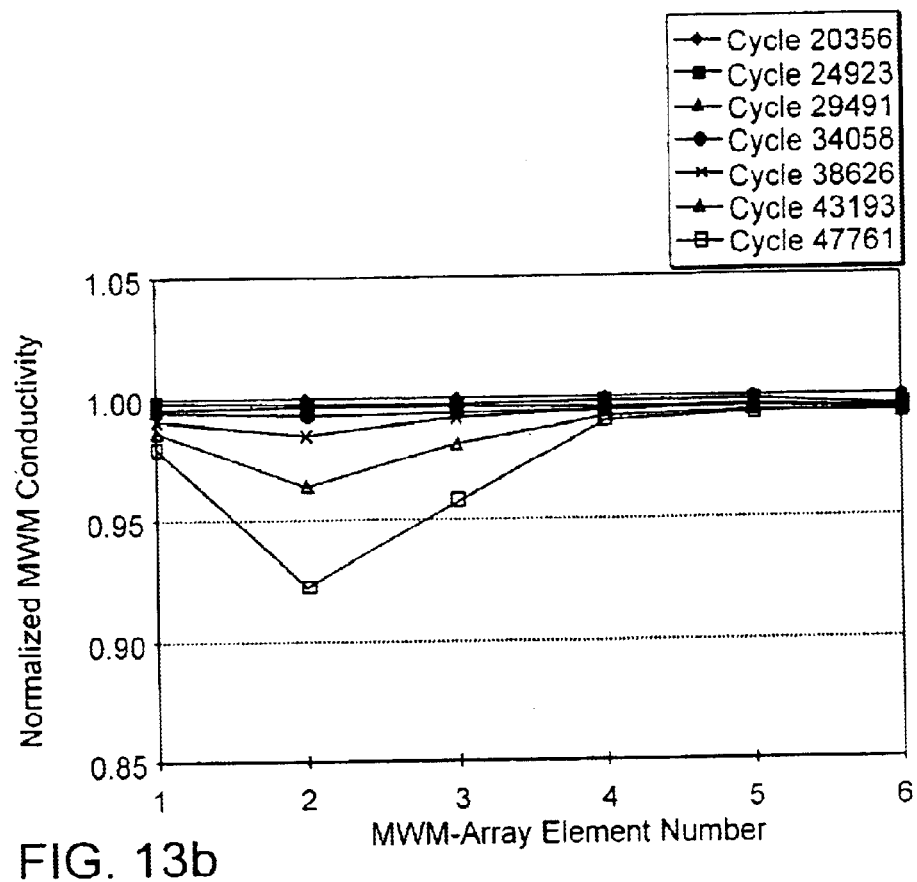
Figure 14A:
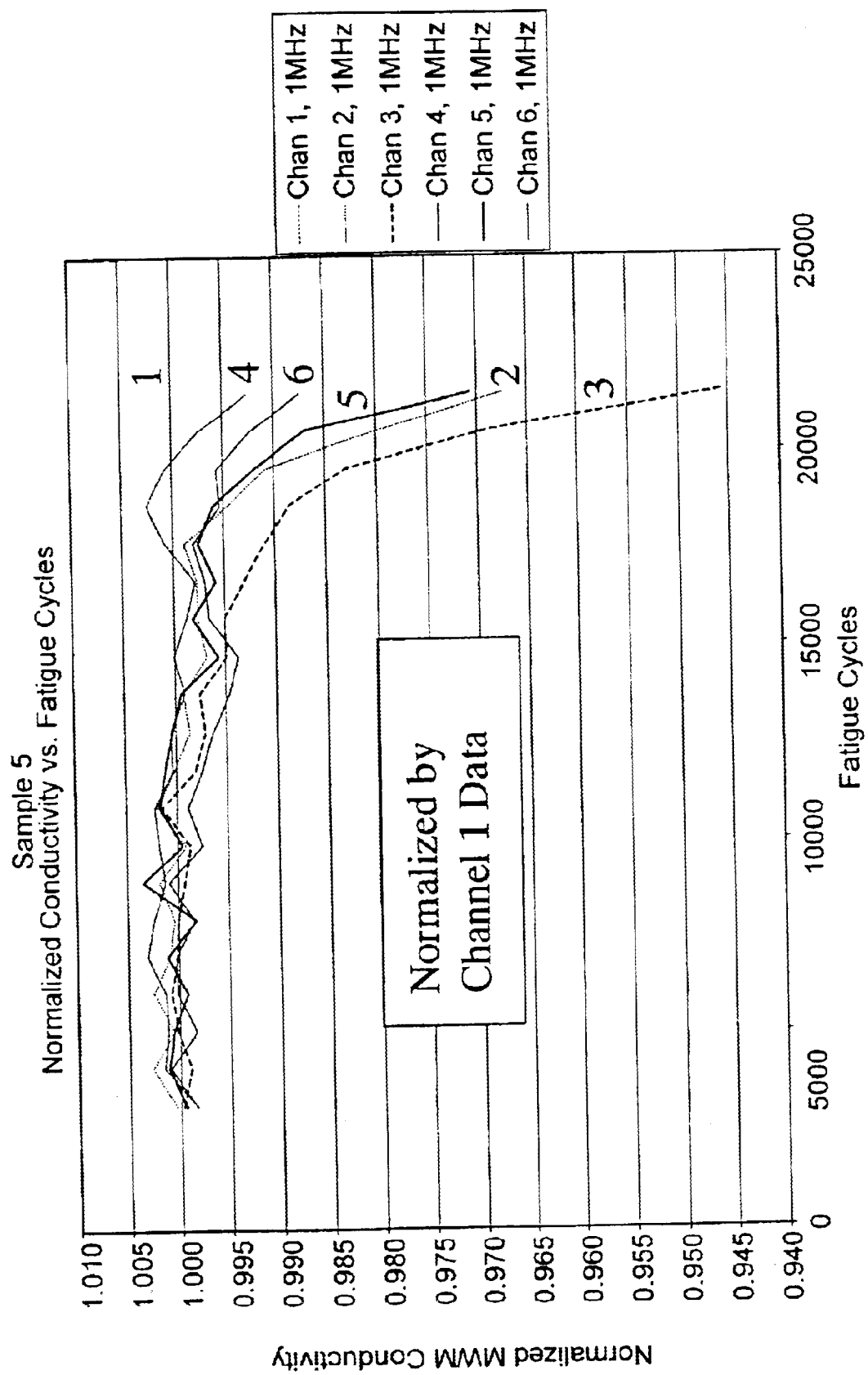
FIG. 14 shows the MWM measured conductivity variation with fatigue cycles for specimens (a) #5, (b) #34, and (c) #32.
Figure 14B:
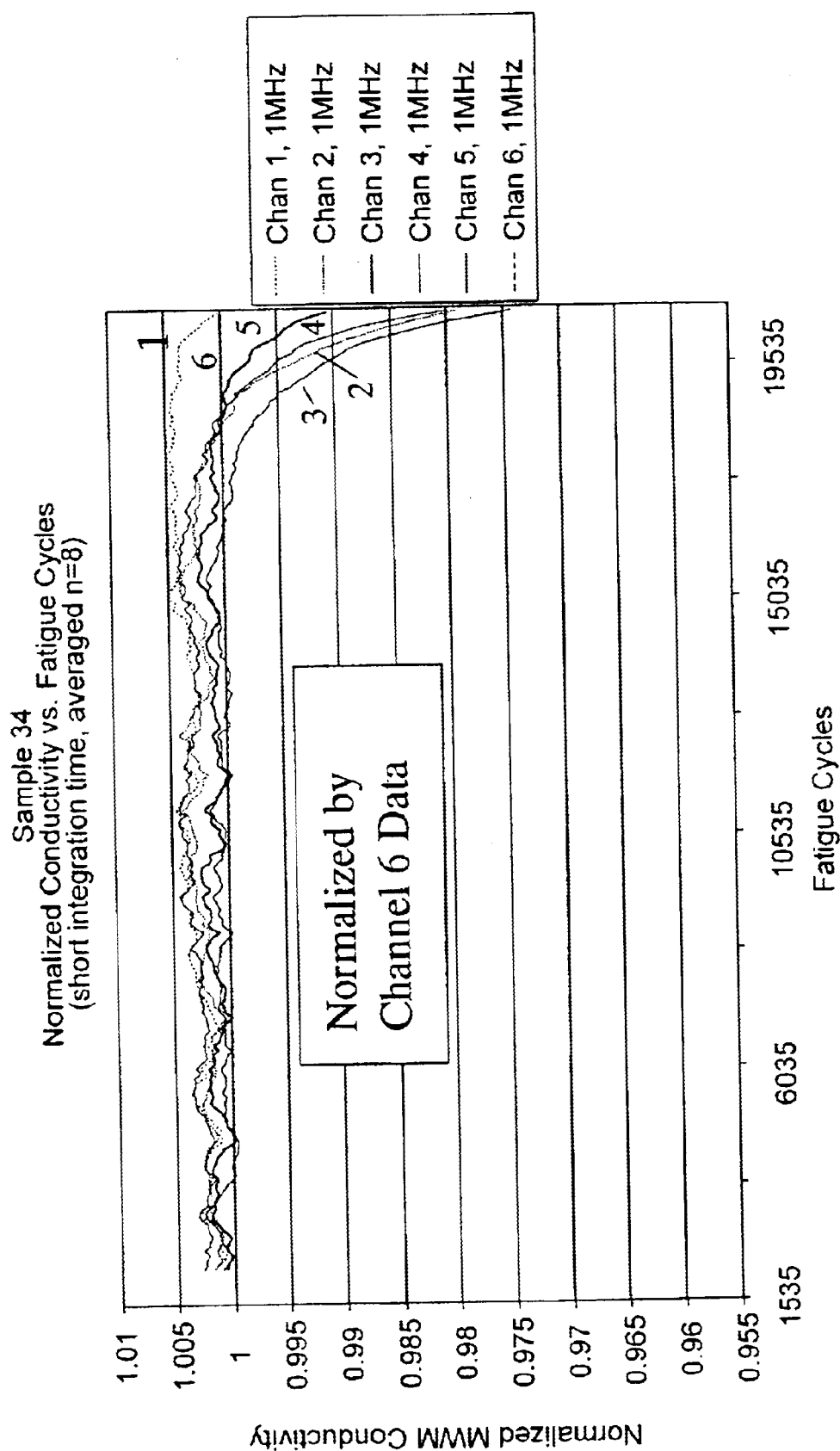
Figure 14C:
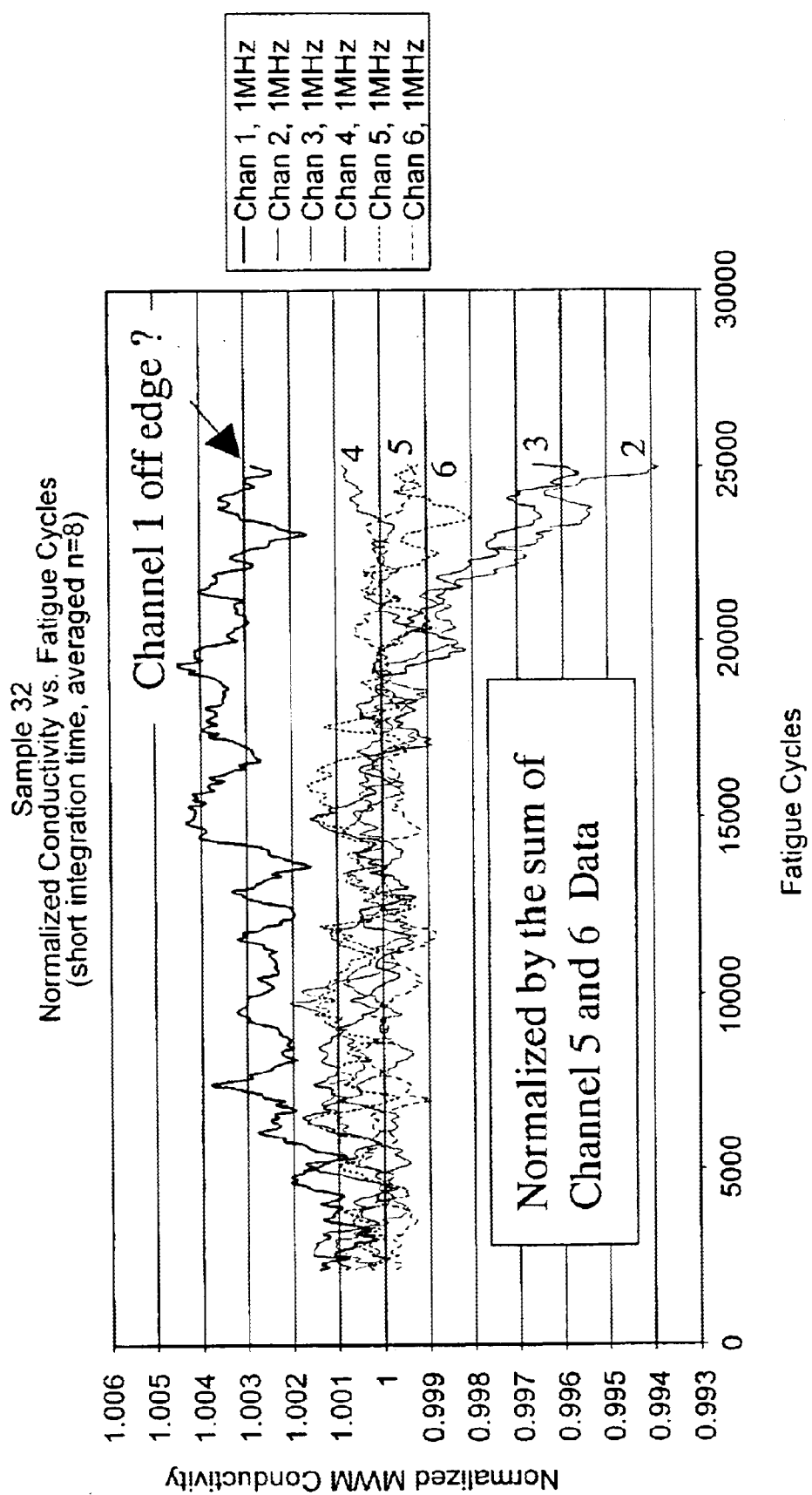
Figure 15A:
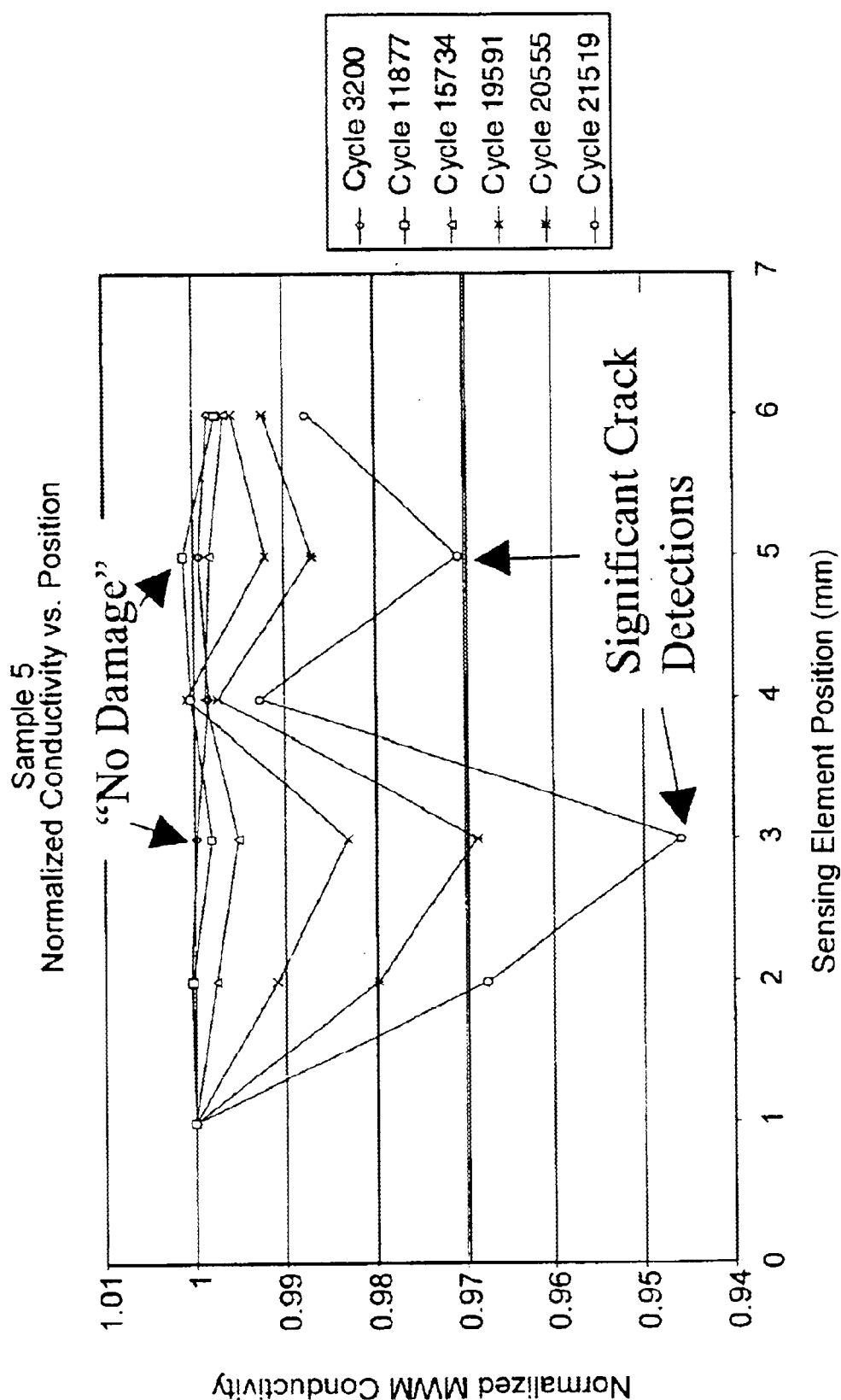
FIG. 15 shows the MWM measured conductivity variation with sensing element position for specimens (a) #5, (b) #34, and (c) #32.
Figure 15B:
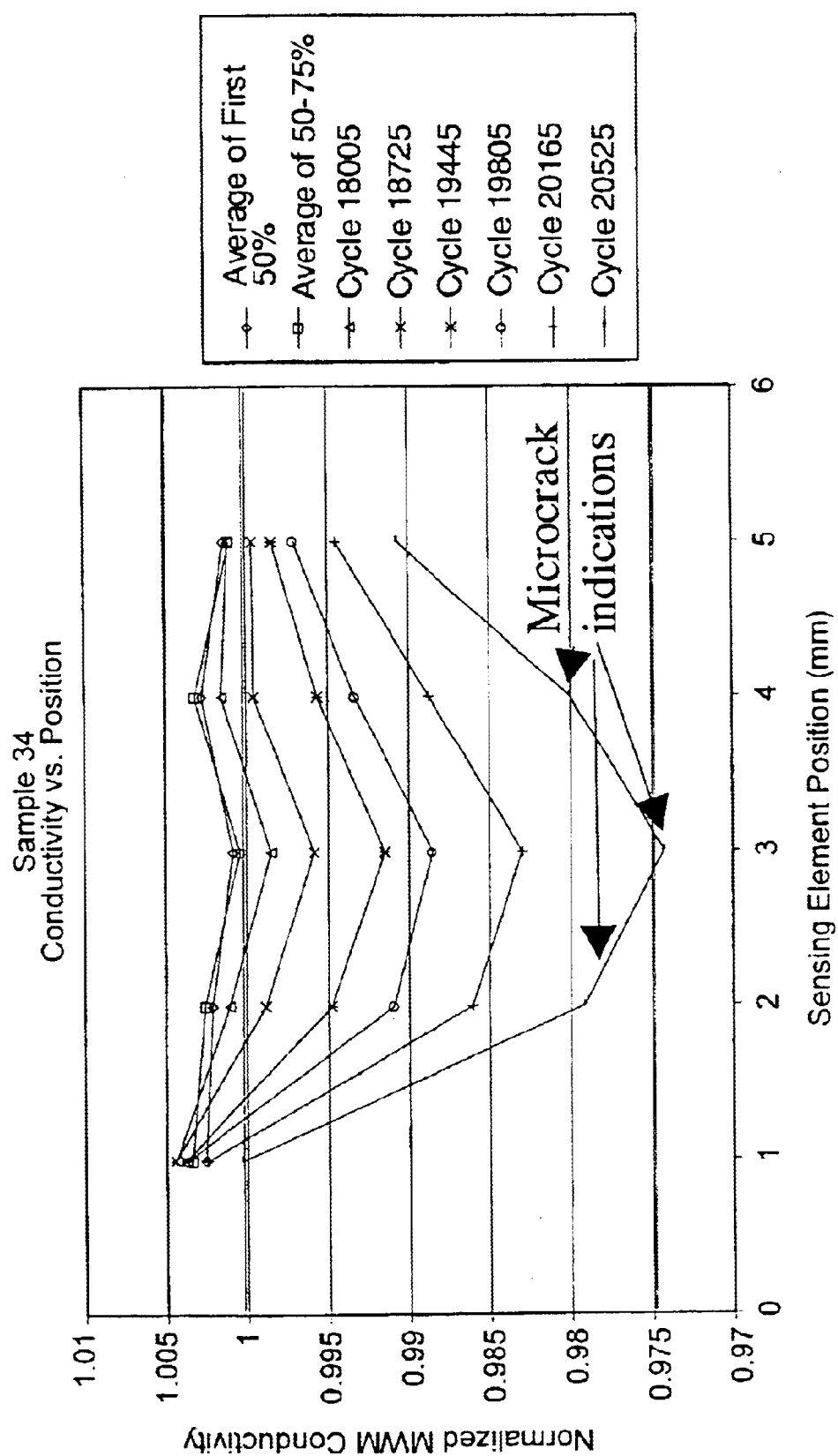
Figure 15C:
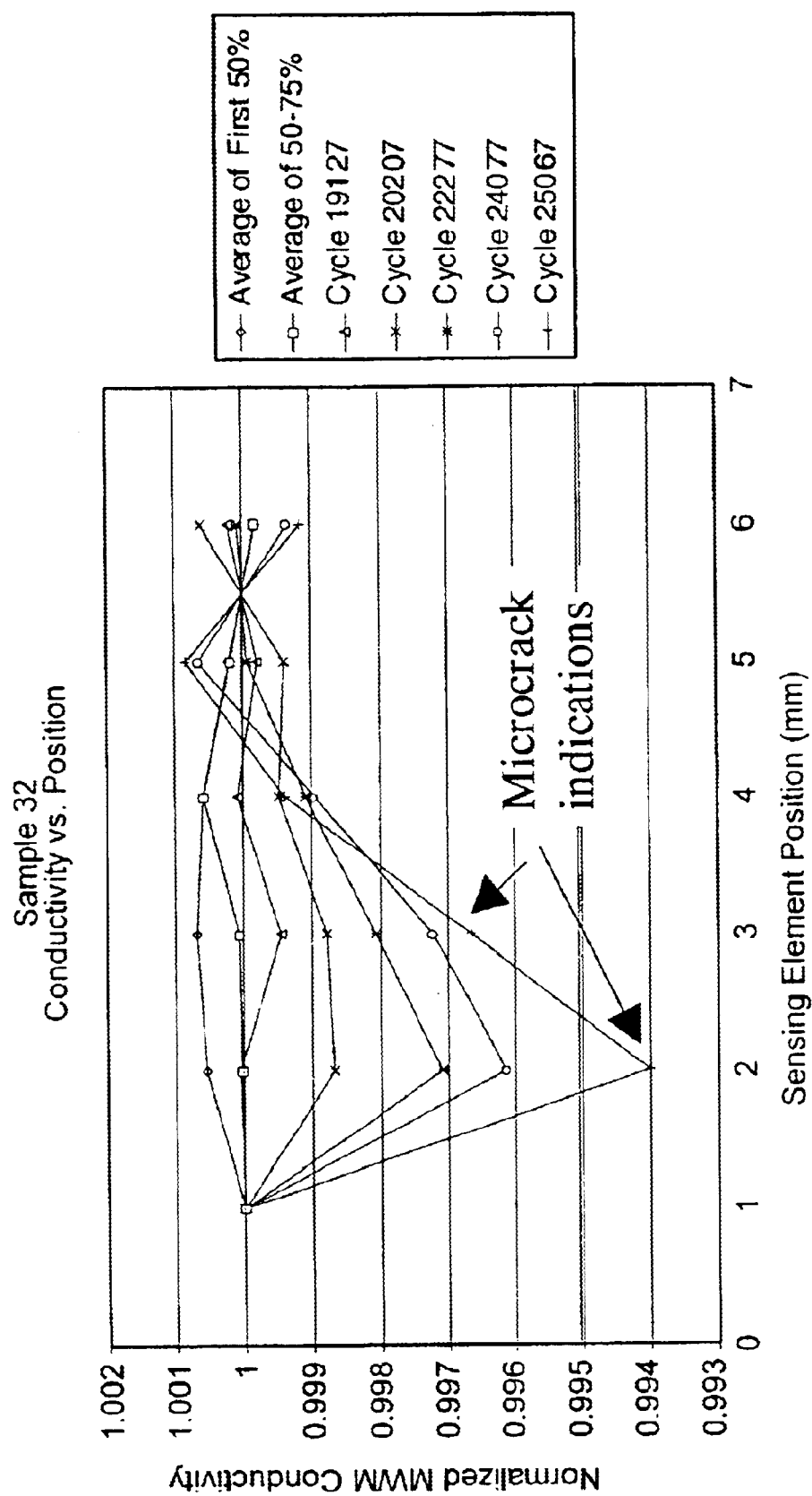

The ability to continuously monitor fatigue specimens while being loaded provides a capability to create samples with very early stage fatigue damage. FIGS. 13a and 13b show the response of an MWM-Array inside a Al 2024 fatigue test specimen and provide an image of the crack initiation and growth as a function of fatigue cycles and position. In this case the specimen was removed from the test after the decrease in MWM measured conductivity indicated the formation of a sizable crack at one location within the hole (Element 2) and the possibility of microcracking at multiple locations along the axis of the hole (Elements 1 and 3). Metallography performed on this specimen after scanning electron microscopy (SEM) identified a crack near Element 2 about 0.034 inches deep and substantially smaller cracks farther away from Element 2. The SEM examination of the area monitored with the MWM-Array revealed multi-site damage with predominantly axial cracks ranging from 0.004 inches to over ⅙ inch in length. Adjacent to the sizable crack detected by the MWM, the SEM examination revealed a series of intrusions parallel to the crack and normal to the machining marks from reaming. These intrusions might be associated with persistent slip bands (PSB). The uniform reduction in absolute conductivity across the six sensing elements as the fatigue coupon warms up (with increasing load cycles) is distinguishable from the local reductions in conductivity by individual elements and allows for compensation of the temperature variations during the measurement. Thermocouples, thermistors or other temperature monitoring methods can be used for this temperature correction.

FIGS. 14a, 14b, 14c, 15a, 15b, and 15c show the normalized electrical conductivities for several more fatigue test specimens. Specimen #5 was a 7075 aluminum alloy while specimens #32 and #34 were Al 2024 alloys. In order to help determine the threshold for detection of fatigue damage, these tests were stopped at different levels of conductivity reductions. In the case of Specimen #32, the fatigue test was stopped when the MWM conductivity drop (relative to the "background" level at neighboring channels) at Channels #2 and 3 were considered indicative of either microcrack formation or advanced stages of fatigue damage accumulation prior to formation of microcracks. These samples were examined thoroughly with an SEM by scanning the surface of the hole at magnifications up to 1,000× across the entire area monitored during the fatigue tests with MWM-Arrays. A number of areas were examined at higher magnifications, up to 10,000×. The SEM examinations are extremely time consuming, since one must cover substantial surface area looking for cracks on the order of 0.002 inches and smaller. Since the cracks for each of these specimens did not reach the outside surface of the component, it appears that the monitoring capability with the MWM-Array allows tests to be stopped with various crack sizes within the hole and particularly at various early stages of "pre-crack" accumulated fatigue damage, during the "short crack" growth stage as well as during "long crack" growth stage.

SEM examinations confirmed the presence and locations of cracks in the specimens. SEM examinations of Specimen #34 revealed a few microcracks, ranging from 0.0004 to 0.0036 inches (10 to 90 (m)) on the surface of the hole monitored by MWM. The 0.0036 inch long intermittent crack was in the area monitored by Elements 3 and 4 of the MWM. A crack in this location is consistent with the MWM response of FIGS. 14b and 15b. An examination of Specimen #34 by an NDE Level 3 inspector, using a very sensitive conventional eddy-current probe, did not reveal any crack-like indications in the area monitored by the MWM-Array during the fatigue test. However, the eddy-current examination detected small crack-like indications on the opposite side of the hole that was not monitored by the MWM-Array. This finding provides an additional confirmation that microcracks not detectable by a traditional eddy-current method but detectable and detected by MWM sensor should have existed on the side monitored by the MWM-Array. After carefully cross-sectioning the specimen to the position of the 0.0036 inch crack, examinations of the crack area with an optical microscope at several magnification levels verified the presence of the crack. Metallography revealed that the crack depth was approximately 0.001 inches (25 (m)). Similar SEM examinations performed on Specimen #5 indicated two cracks, which is consistent with the MWM data of FIG. 15a SEM examinations of Specimen #32 revealed a few cracks ranging in length from 0.0005 to 0.006 inches (12 to 150 (m)), with two distinct cracks that were less than 0.002 inches long. The longest detected crack was intermittent, i.e., consisted of a few adjacent continuous cracks. Assuming a semicircular geometry for the cracks, the estimated depth of individual continuous cracks ranging in length from 0.0005 to 0.0024 inches (12 to 60 (m)) would be between 0.00025 and 0.00125 inches (6 and 30 (m)).

Figure 17:
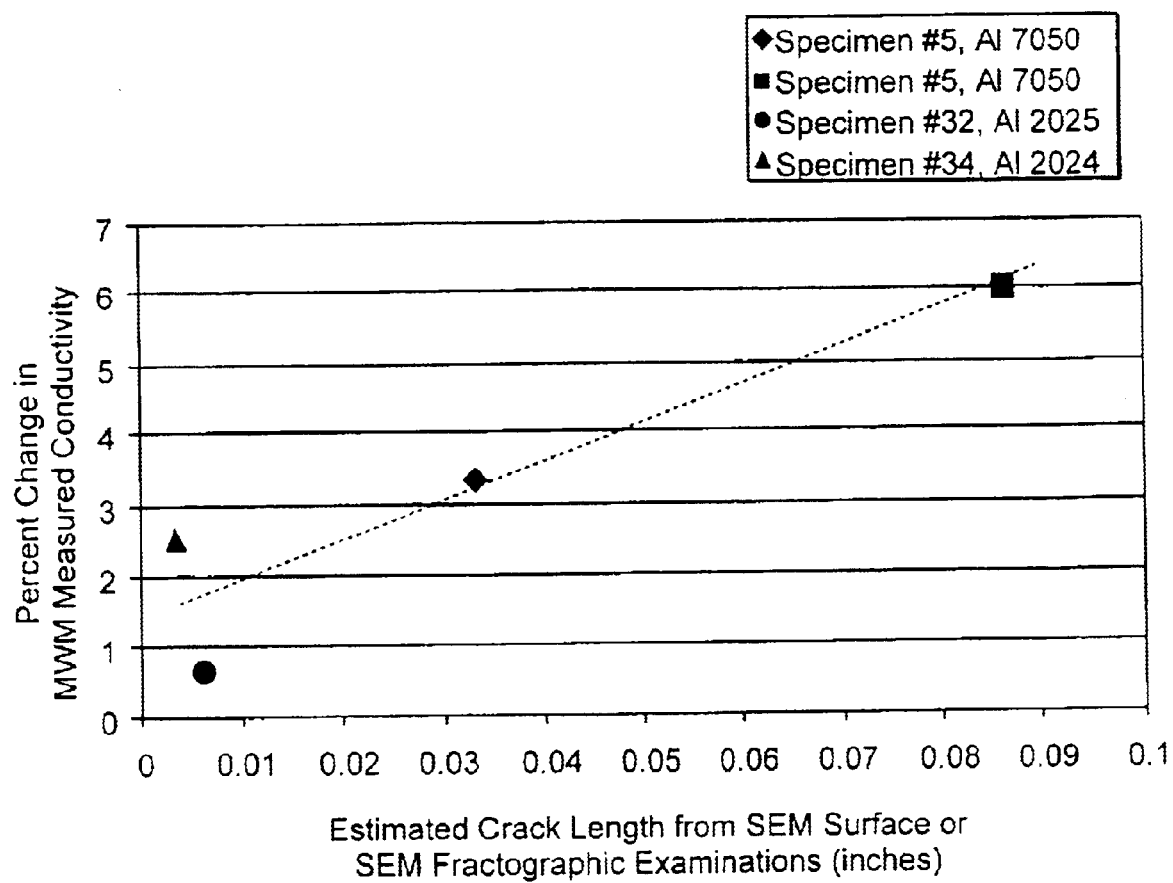
FIG. 17 illustrates the relationship between the MWM measured conductivity changes and crack length estimated from SEM.

FIG. 17 summarizes the results on the tested specimens in terms of crack length compared to the MWM measured data. The data for specimens #32 and #34 are difficult to analyze because there are multiple crack indications and the longer cracks (e.g., the 0.006 inch long crack in specimen #32) appear to be intermittent (i.e., formed from several shorter cracks). Furthermore, the depth of penetration of the MWM magnetic fields at 1 MHz is on the order of 0.003 inches so that cracks shallower than 0.003 inches will produce a MWM conductivity dependence based on depth as well as length. For these cracks, a higher frequency measurement (e.g. 6 or 10 MHz) is expected to provide a more reliable measure of crack length as well as a better signal to noise for improved sensitivity to microcrack detection. Multiple frequency measurements should then allow for estimating crack propagation in both length and depth directions.

Figure 16:
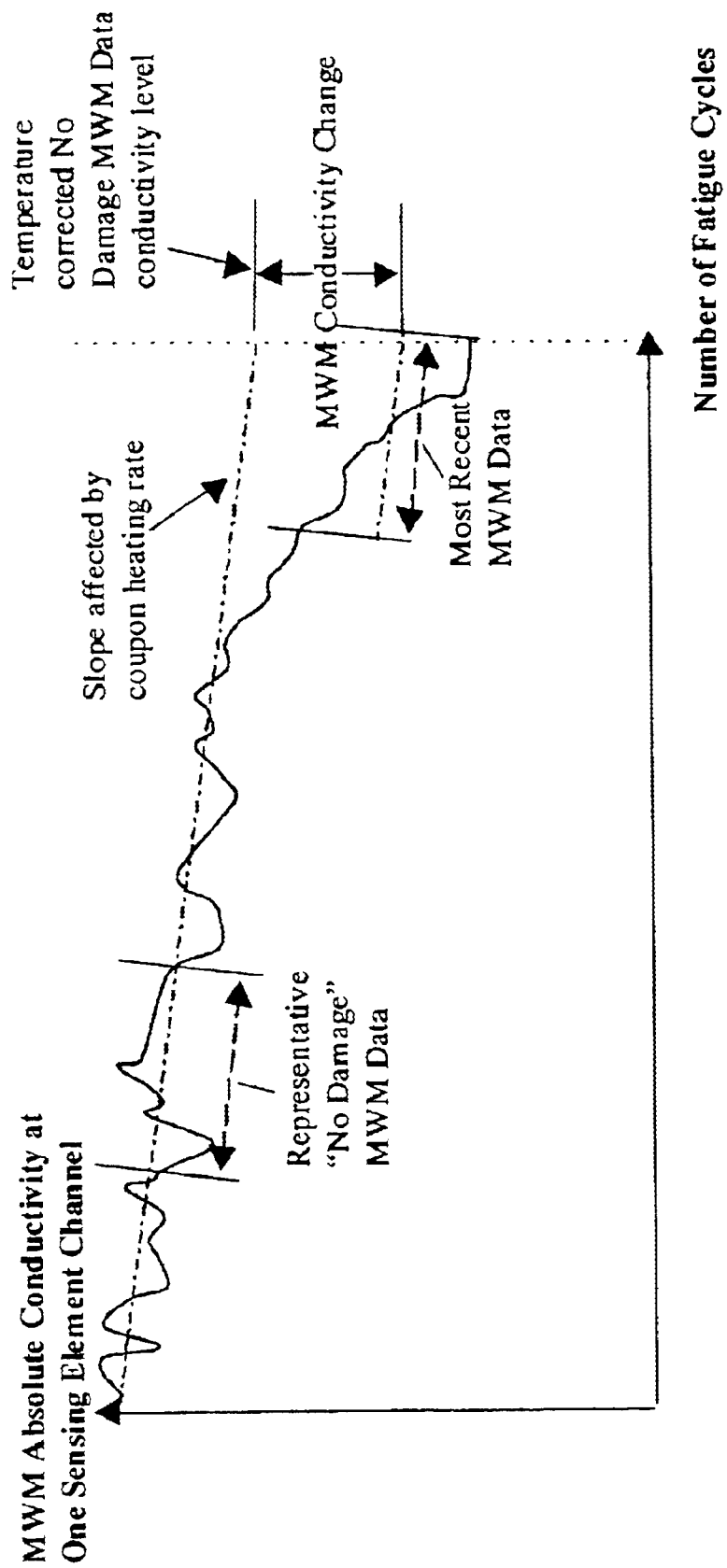
FIG. 16 shows an illustration of an algorithm for detection of the onset of fatigue damage using a surface mounted eddy-current sensor.

The reliable detection of the onset of fatigue damage and the number of cycles to crack initiation, $N_i$, can be performed automatically using trend detection algorithms. An example detection algorithm is to use a simple hypothesis test to build a first set of statistics (e.g., standard deviations) for the no damage MWM conductivity data at the beginning of the test and also a second set of statistics for a moving window of most recent data. This grouping of data is illustrated in FIG. 16 for an example conductivity variation with number of fatigue cycles. The data must first be corrected for thermal drift, either by using thermocouples or by filtering the (nearly linear) temperature trend from the damage related conductivity changes vs. number of fatigue cycles data A simple hypothesis test might require that the MWM conductivity change be at least twice the sum of the standard deviations of the No Damage MWM Data and the Most Recent MWM Data. An automated test would determine the confidence level of the statement that "the most recent data shows a conductivity drop not related to metal temperature changes, compared to the earlier no damage data." The confidence level will depend on the statistical separation of the two sets of data. Similar techniques are commonly used to detect downward trends in noisy data, such as the stock market. An automated test is an improvement over the human interpretation of visual data as human operators typically have an expectation of results, based on prior knowledge of the coupon material or expected number of cycles to initiation, that can influence the results.

Another aspect of the invention described here relates to unique geometries for fatigue specimens that intentionally shape the stress distribution so that the damage initiation sites will lie within the area under inspection by a surface mounted eddy-current sensor.

Figure 18C:
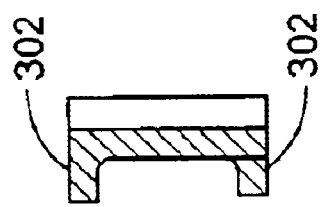
FIG. 18 shows an engineering drawing for a fatigue specimen having a reduced thickness center section and reinforcement ribs on the sides.
Figure 18A:
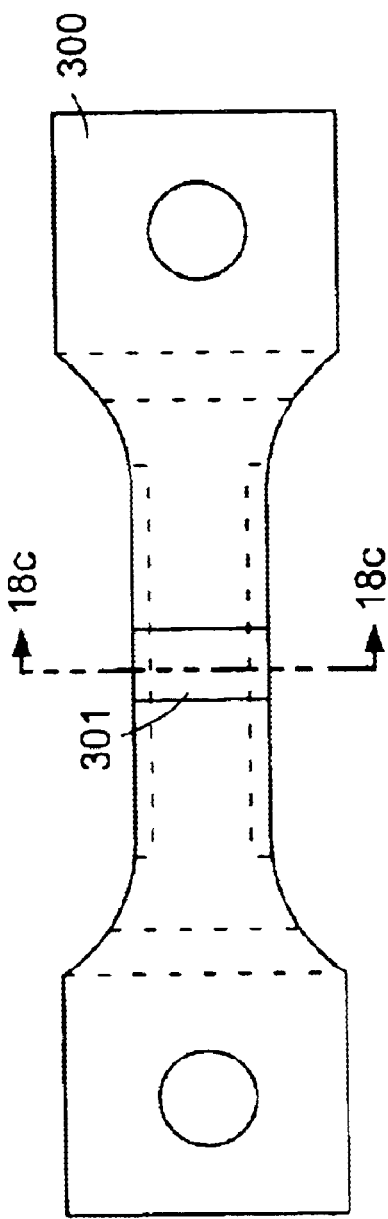
Figure 18B:
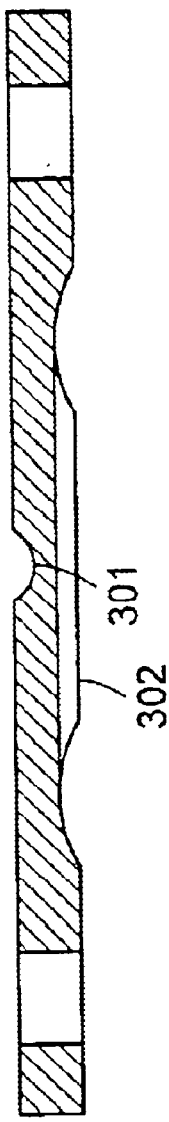
Figure 20C:
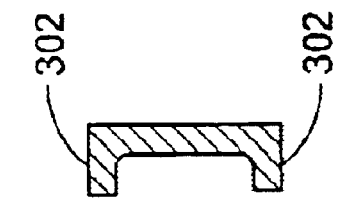
FIG. 20 shows an engineering drawing for a fatigue specimen having a reduced thickness center section, reinforcement ribs on the sides, and symmetrical radius cutouts on both sides of the thinned area.
Figure 20A:
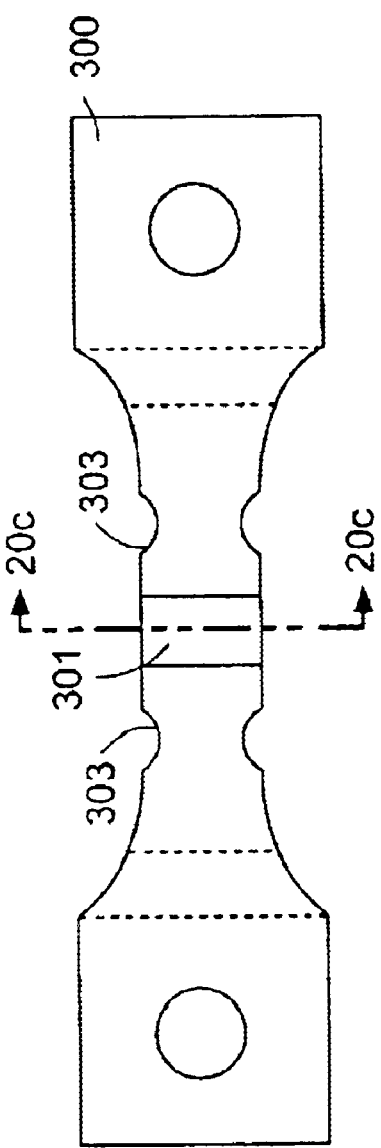
Figure 20B:
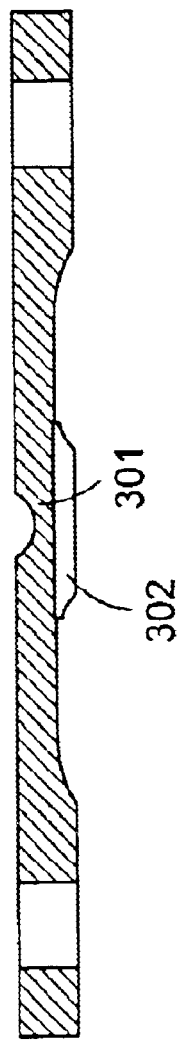

With a traditional dogbone design, fatigue damage starts in the middle of the specimen but is not localized along the length of the samples. Thus, there is no guarantee that the fatigue damage will initiate beneath the surface mounted sensor. The new specimen geometries described here, and illustrated in FIGS. 18, 19, and 20, localize fatigue damage both lengthwise to ensure it occurs in the reduced center section of the specimen 30 and in the middle of the reduced thickness center section in order to avoid cracks at the edges of the gage section. The lengthwise localization is accomplished by thinning across the center portion of the specimen 301. Reduction of the formation of cracks at the edges is accomplished with reinforcement ribs along the edges 302 and/or with symmetrical radius cutouts 303 on both sides of the specimen, above and below the gage section. FIG. 18 shows a dogbone specimen 300 with thinning at the center section of the specimen 301 and reinforcement ribs 302. The thinning at the center section can also be accomplished with cutout sections on each side in order to avoid bending moments. FIG. 19 shows a dogbone specimen 300 with thinning at the center of the specimen 301 with radius cutouts 303 on both sides of the thinned section. FIG. 20 shows a dogbone specimen 300 with thinning at the center section 301 and both reinforcement ribs 302 and radius cutouts 303. Each of these designs significantly reduces the stresses at the edges and thereby prevents initiation of fatigue damage at the edges in the early stages of fatigue.

FIGS. 21 through 41 illustrate new embodiments for the MWM-Array sensor structure and applications of these structures. These embodiments provide greater sensitivity to the flaws being investigated and can be applied to both surface mounting on and scanning across test materials.

Figure 21A:
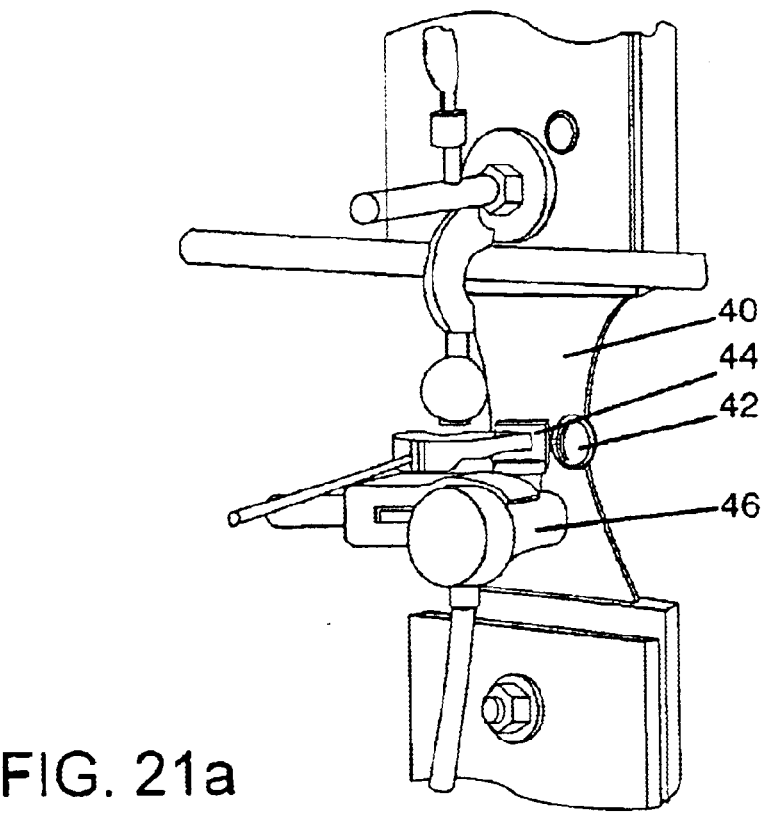
FIG. 21 shows (a) a fatigue test configuration with the MWM-Array mounted at a steel fastener installed on the Al 2024 test specimen and (b) a side view of the fatigue test configuration.
Figure 21B:
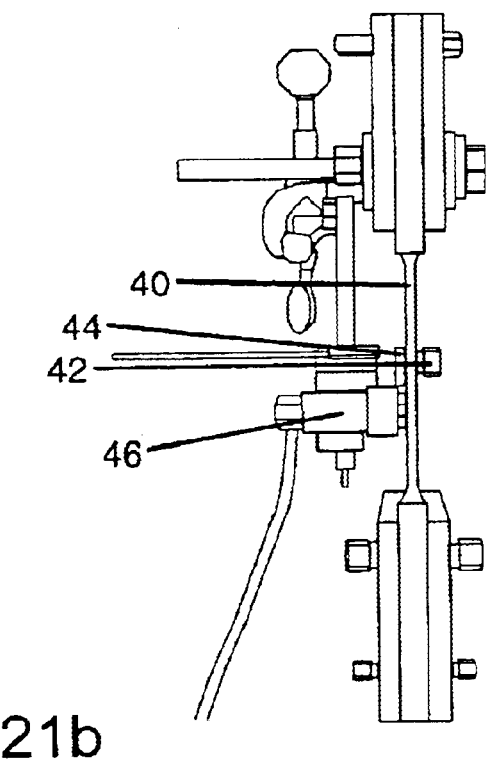

FIGS. 21a and 21b show a sample configuration for the detection of cracks near fasteners with MWM sensors mounted on the surface. A steel fastener 42 is attached to the fatigue test coupon 40 of Al 2024 at a semicircular notch. The mounting bracket 44 holds the MWM sensor against the surface of the test coupon throughout the duration of the tension-tension fatigue test. The electronics package 46 provides signal amplification of the sensing elements in the MWM sensor, as necessary. MWM sensors can be permanently mounted at fasteners in difficult-to-access locations and elsewhere.

Figure 22:
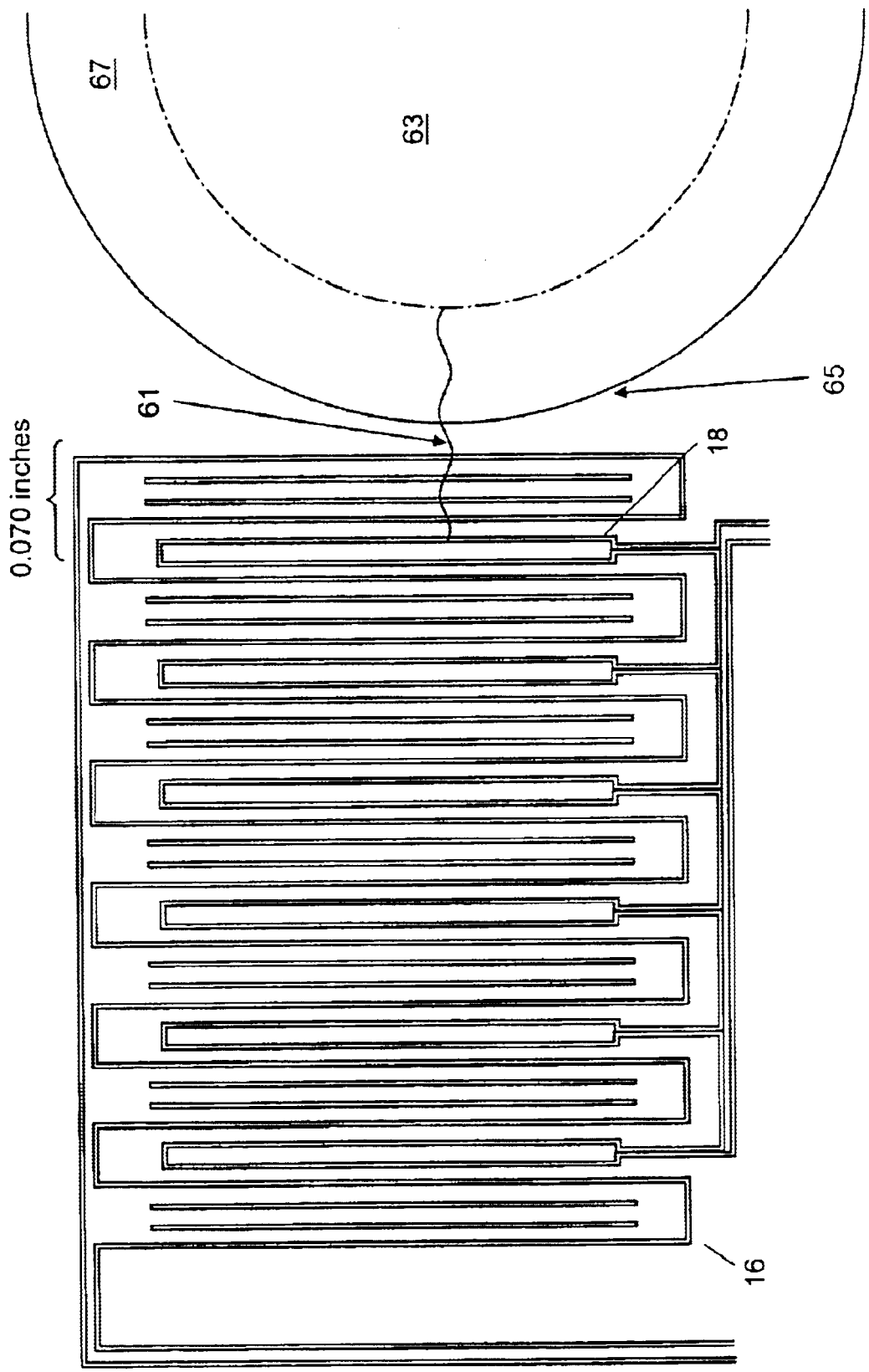
FIG. 22 is an illustration of the use of an MWM sensor for measuring crack length near a fastener.

FIG. 22 illustrates the positioning of an MWM sensor 16 near the hole 63 used for a steel fastener 67. A crack 61 formed beneath the fastener as a result of the tension fatigue load cycling on the test coupon of FIGS. 21a and 21b. The crack 61 originally initiated at the notch of the hole beneath the head of the fastener and was detected when it extended approximately 0.070 inches (1.75 mm) beyond the edge of the fastener head 65. However, this crack propagated only 0.020 inches under the footprint of the sensor array defined by the region covered by the active sensing element, as illustrated in FIG. 22. The signal measured by the MWM, and hence the effective conductivity and lift-off measured by the sensor, will change as the crack propagates across the sensing elements 18. Orienting the sensor so that the extended portions of the windings are perpendicular to the crack provides maximum sensitivity to the presence of the crack, as illustrated in FIG. 4a. The earliest detection of the crack occurs as the crack tip approaches the position of the end-most sensing element. This suggests that it is desirable to locate the first sensing element (as opposed to a dummy element, denoted by 14 in FIG 1) as close as possible to the edge of the primary winding meanders. Although eliminating the dummy element on the edge will influence the ability to perform an air calibration measurement, it can provide an earlier indication of the presence of a crack beneath the fastener. Furthermore, although this MWM sensor does not locate the position of the crack along a meander, the length of the crack can be estimated from the reduction in the effective conductivity as the crack propagates across each individual secondary element.

FIG. 23 illustrates an alternative embodiment for an MWM-Array. This linear sensing MWM-Array has a primary winding 52 for creating a spatially periodic magnetic field for interrogating the MUT and a plurality of secondary elements 54 along the length of each meander. The primary winding 52 is split into two parts, with lead connections 66 and 68 on either side of the sensor. This configuration for the primary winding uses two conducting loops to impose a spatially periodic magnetic field, similar to the single loop meandering winding 10 of FIG. 1. This configuration minimizes the effects of stray magnetic fields from the lead connections to the primary winding, which can create an extraneous large inductive loop that influences the measurements, maintains the meandering winding pattern for the primary, and effectively doubles the current through the extended portions of the meanders, as will be discussed with reference to FIGS. 35, 37, and 40. Secondary elements that couple to the same direction of the magnetic field generated by the primary winding, such as elements 54 and 56, are connected with connections 70, perpendicular to the primary winding meander direction, so that the sum of the secondary element responses appears at the winding leads 64.

To provide complete coverage when the sensor is scanned across a part or when a crack propagates across the sensor, perpendicular to the extended portions of the primary winding, secondary elements 58 in adjacent meanders of the primary are offset along the length of the meander. The dummy elements 60 are used to maintain the periodic symmetry of the magnetic field and the extension elements 62 are used to minimize differences in the coupling of the magnetic field to the various sensing elements, as described in patent application Ser. No. 09/182,693. Additional primary winding meander loops, which only contain dummy elements, can also be placed at the edges of the sensor to help maintain the periodicity of the magnetic field for the sensing elements nearest the sensor edges. The secondary elements are set back from the cross-connection portions 53 of the primary winding meanders to minimize end effects on the measurements.

The connection leads 64 to the secondary elements are perpendicular to the FU primary winding meanders, which creates a "T" shape and necessitates the use of a multi-layer structure in fabricating the sensor. The sensor of FIG. 23 has the layer containing the primary winding 52 separated from a layer containing the secondary windings by a layer of insulation. Generally, layers of insulation are also applied to the top and bottom surfaces of the sensor to electrically insulate the primary and secondary windings from the MUT.

All of the leads to the secondary elements can also be reached from one side of the sensor. In contrast, the basic sensor geometry of FIG. 1 has a single layer structure and connections to secondary elements, when placed on opposite sides of the primary winding meanders, require access to both sides of the sensor.

Figure 23A:
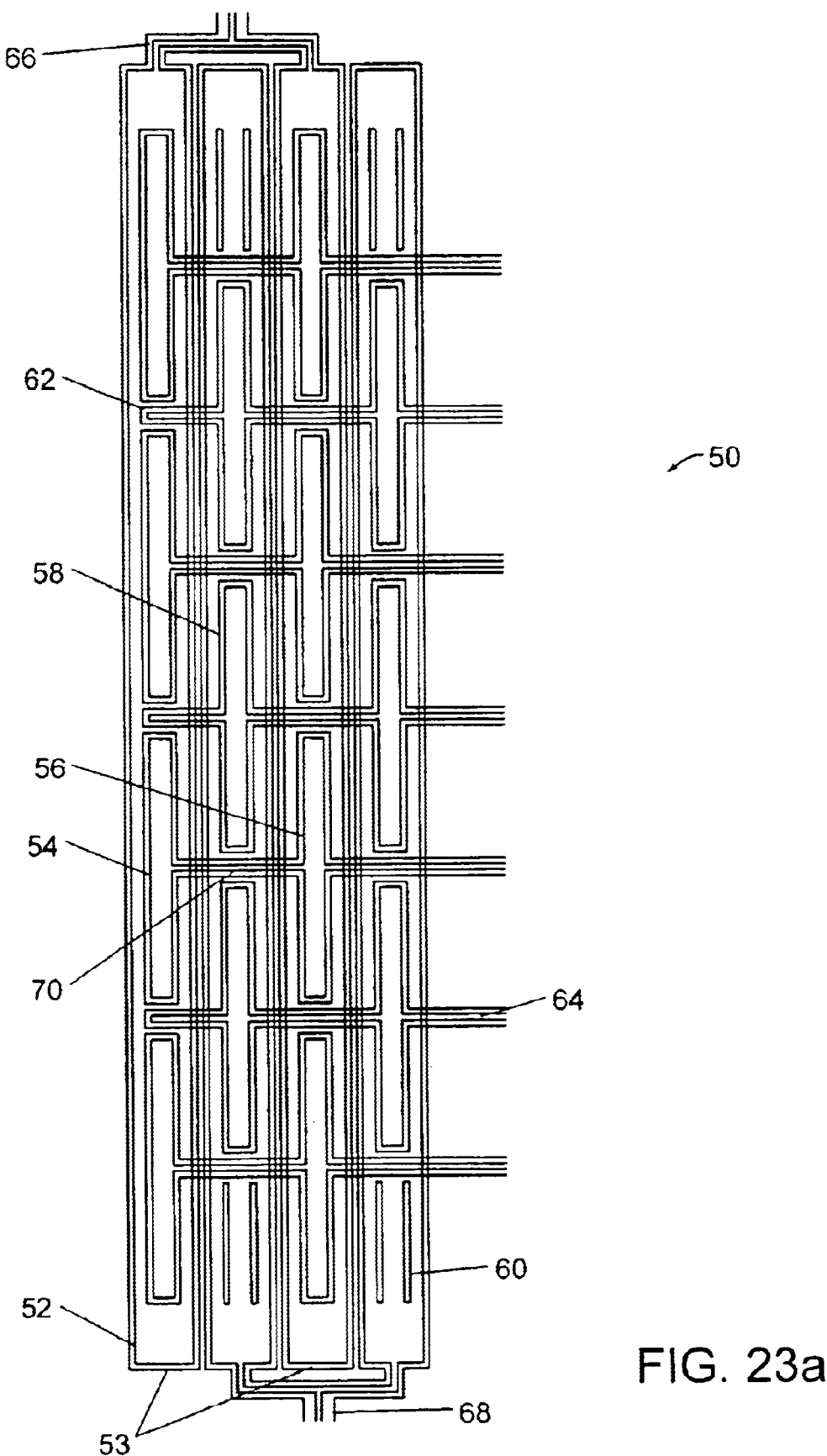
FIG. 23 is (a) a plan view of a linear MWM-Array for crack detection and determining crack location and (b) an expanded view of a sensing element in the linear MWM-Array.
Figure 23B:
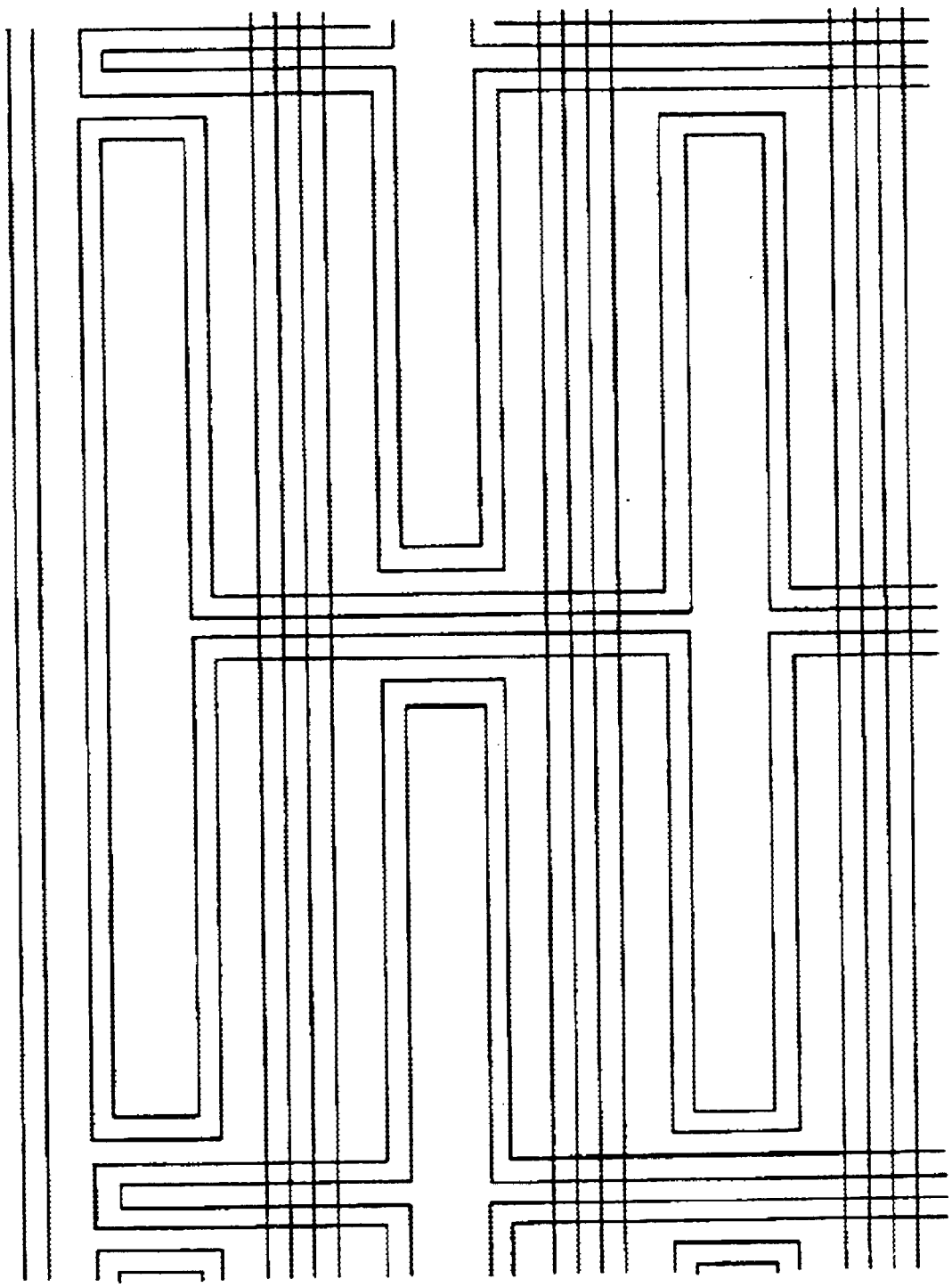

An advantage of the sensor of FIGS. 23a and 23b over the sensor geometry of FIG. 1 is that it can detect cracks and determine the crack location within the footprint of the sensor. When a crack propagates perpendicular to the primary winding meander direction, only the secondary elements directly over the crack will sense a significant change in signal or reduction in effective conductivity. As the crack continues to propagate, the signal from additional secondary elements will be affected. In principle, the crack length can be determined from the reduction in effective conductivity. In contrast, the secondary elements 12 of FIG. 1 span the length of the primary winding and cannot distinguish the crack position along the length of the meander.

Figure 24A:
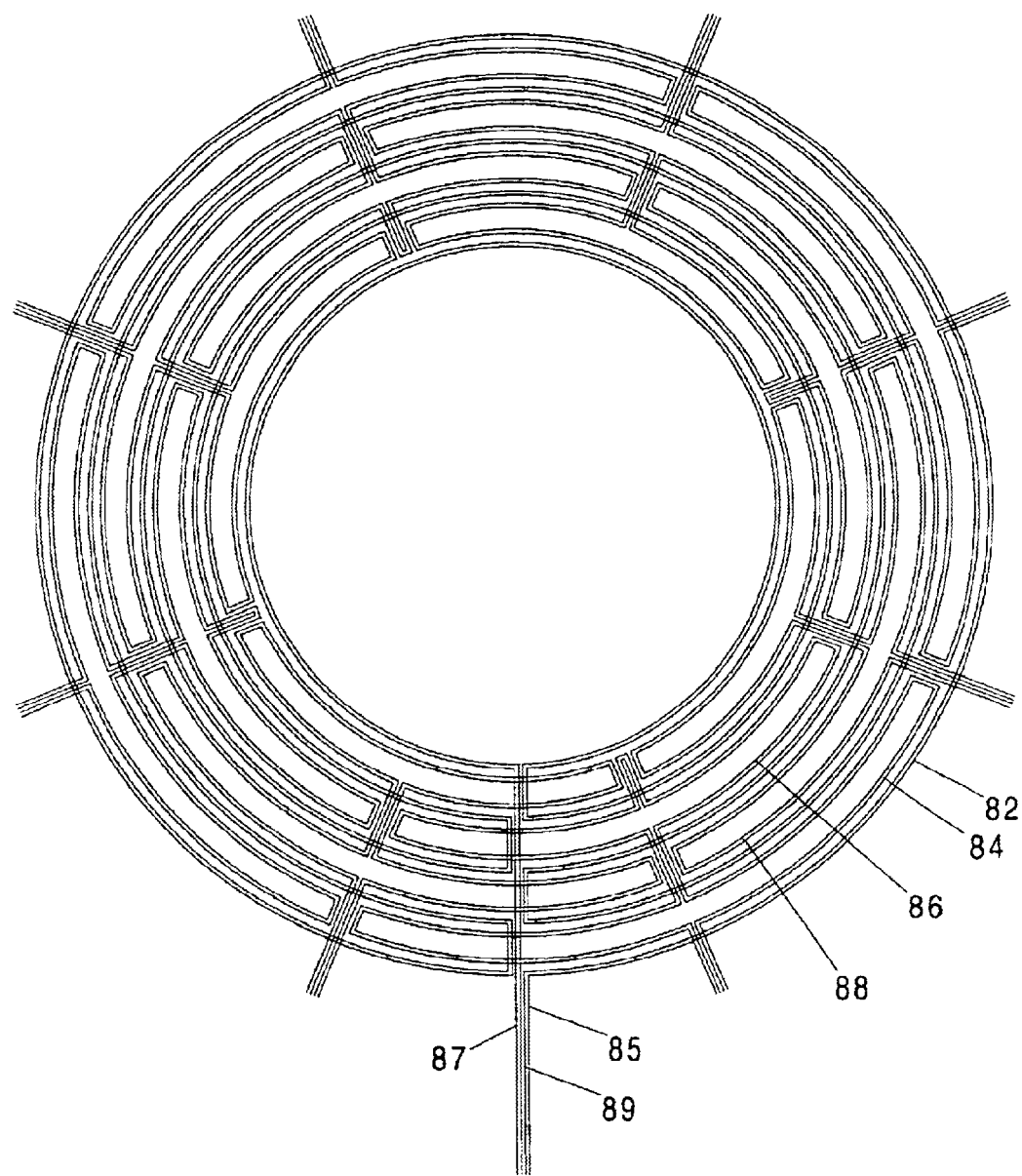
FIG. 24 is (a) a plan view of an MWM-Rosette for crack detection and determining crack circumferential (azimuthal) location and (b) an expanded view of some of the winding connections in an MWM-Rosette.
Figure 24B:
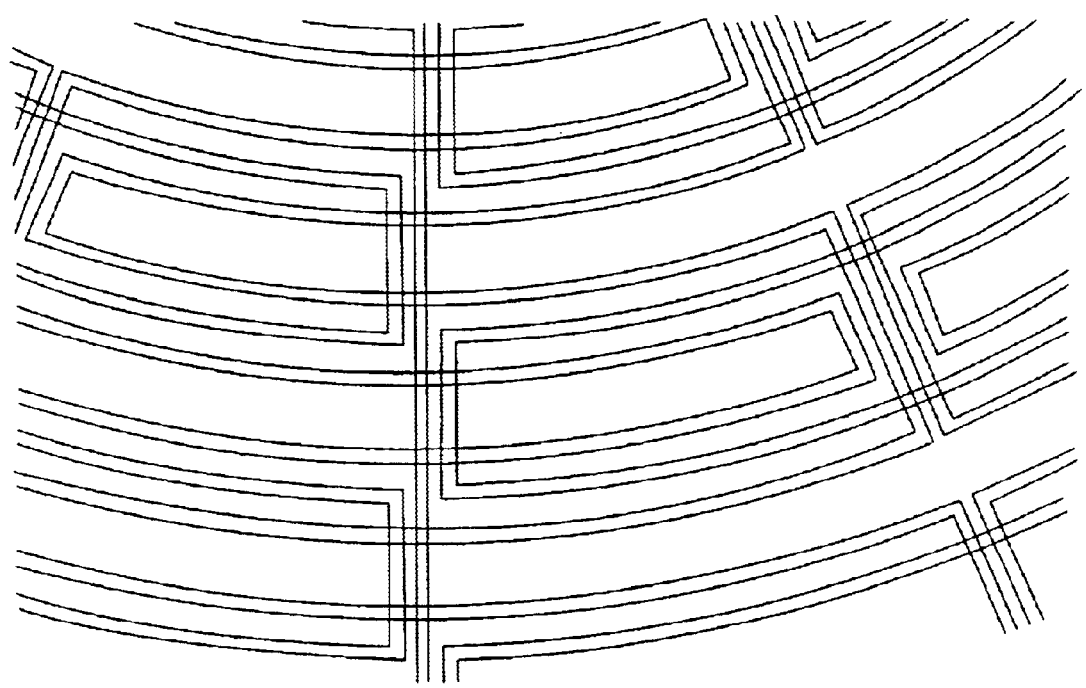
Figure 25:
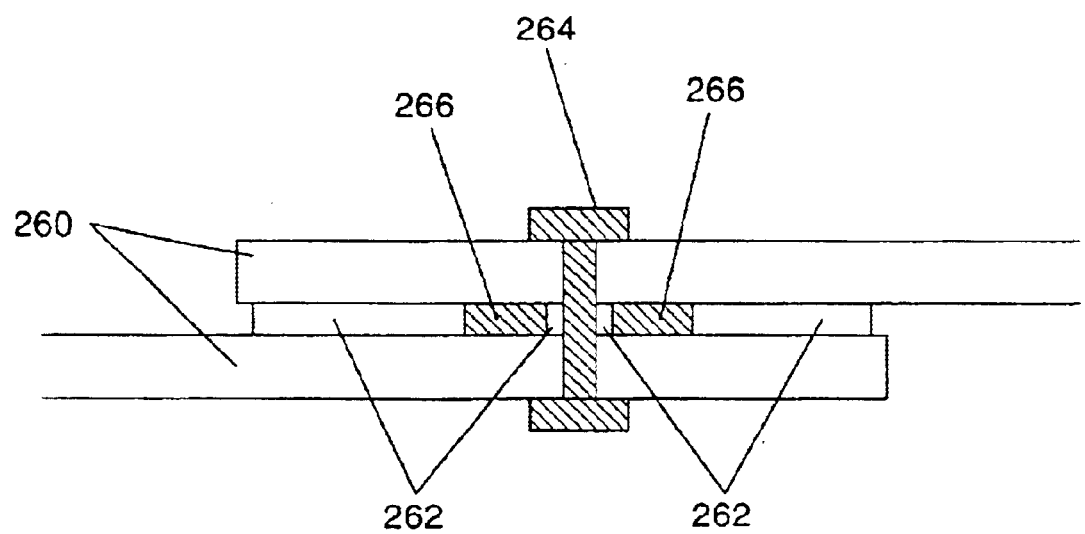
FIG. 25 shows an eddy-current array mounted between layers of a structure.
Figure 26:
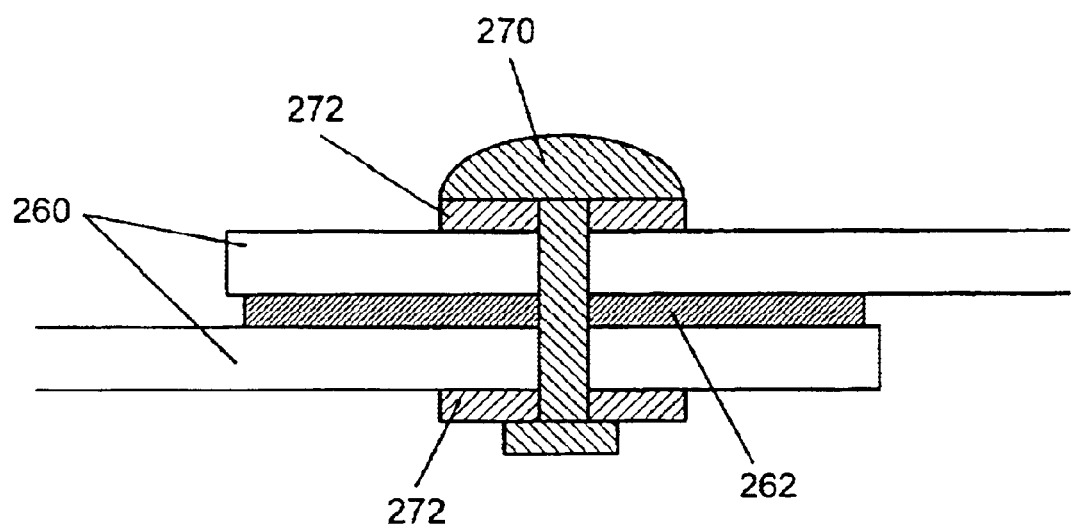
FIG. 26 shows an eddy-current array mounted underneath a fastener.
Figure 27A:
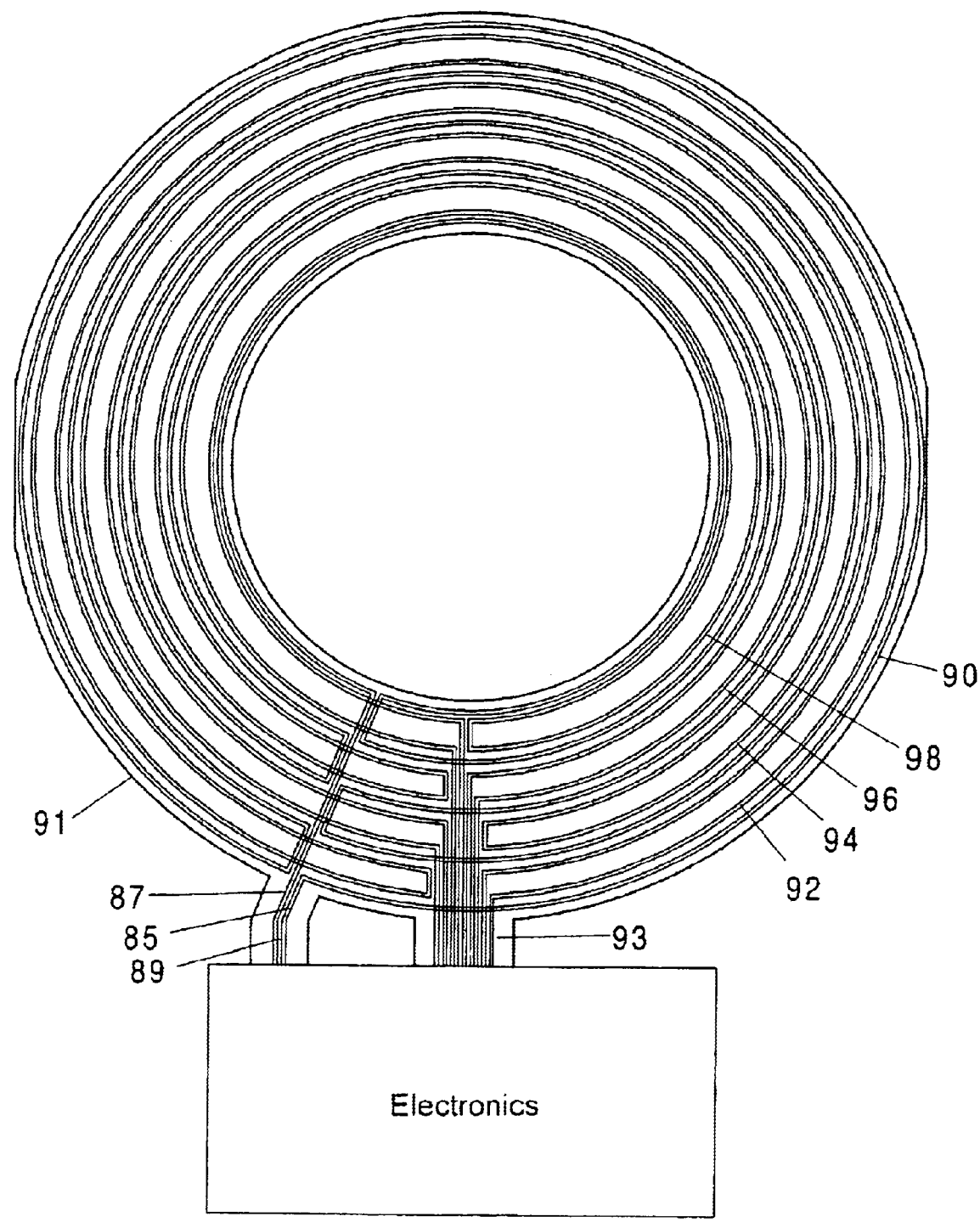
FIG. 27 is (a) a plan view of an MWM-Rosette for crack detection and crack length measurement and (b) an expanded view of some of the winding connections in an MWM-Rosette.
Figure 27B:
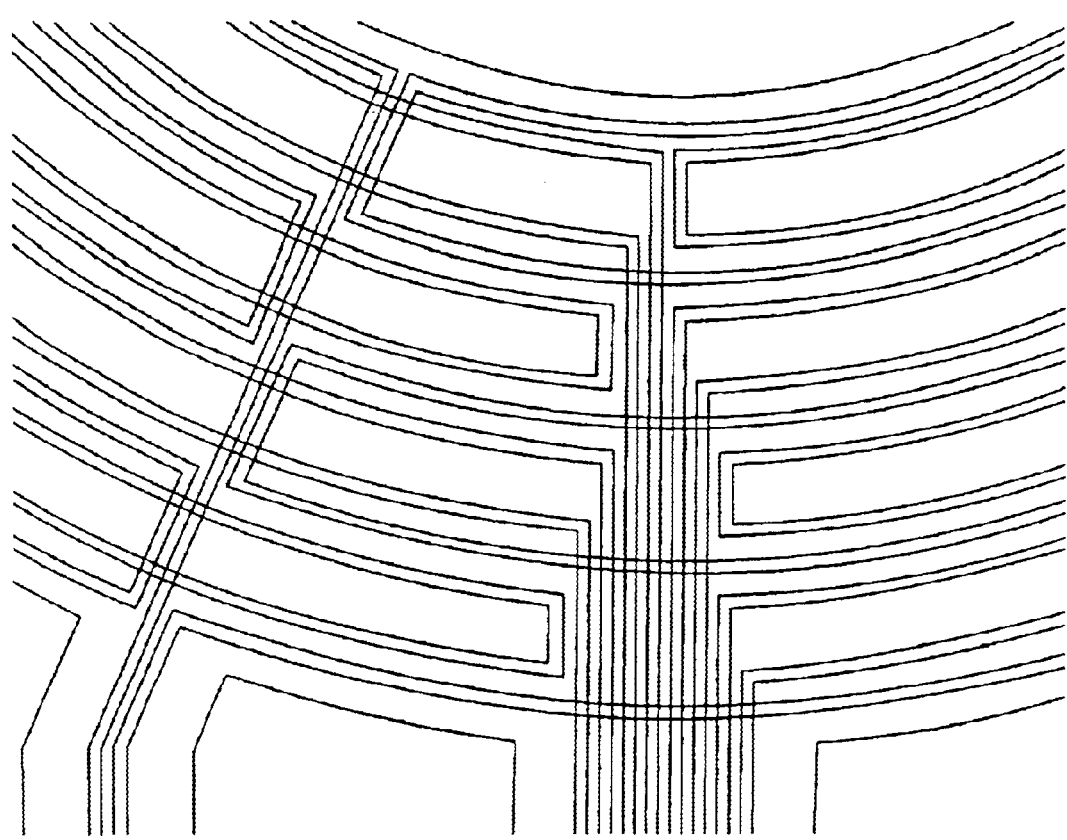

FIGS. 24a and 24b show a circularly symmetric embodiment of an MWM-Array. This MWM-Rosette or periodic field eddy-current-rosette (PFEC-Rosette) maintains the spatial periodicity of the magnetic field in the radial direction with primary winding 82. The characteristic dimension for this radial spatial periodicity is the spatial wavelength. The plurality of secondary elements 84, 86, and 88 provide complete coverage around the circumference of the sensor and can be used to detect cracks and determine the crack location. The gap 89 between the primary winding conductors 85 and 87 is minimized to reduce any stray magnetic fields from affecting the measurements. FIGS. 27a and 27b show a circularly symmetric variation of a standard MWM-Array. As with FIGS. 24a and 24b, the primary winding 90 maintains the spatial periodicity of the magnetic field in the radial direction. The secondary elements 92, 94, 96, and 98 provide complete coverage around the circumference of the sensor and can be used to detect cracks and determine the crack length. The first active sensing (secondary) element is located as close as possible to the inside of the sensor to enable early detection of cracks. The primary winding 90 is fabricated onto one side of a substrate 91 while the secondary elements 92, 94, 96, and 98 are fabricated onto the opposite side of the substrate. Individual connections 93 are made to each of the secondary elements for independent measurements of the response of each element. Alternatively, the net signal from all of the elements can be obtained by connecting the loops together.

The rosette configuration is most useful for crack detection and location around circularly symmetric regions, such as around fasteners. The rosette configuration can also be used in areas where the stress distribution and the crack initiation point and growth direction may not be known because of complex component geometry or service related repairs.

The MWM-Array configurations of FIGS. 23a, 24a, and 27a can be surface mounted on a part, as has been demonstrated for the standard MWM and MWM-Array of FIGS. 1, 8a, and 8b. This mounting can take the form of a clamp or pressure fitting against the surface, or the sensors can be mounted with an adhesive and covered with a sealant. Since the MWM sensors do not require an intimate mechanical bond, compliant adhesives can be used to improve durability.

The MWM sensors embodied in FIGS. 1, 8a, 23a, 24a, 27a, 38a, 39a, 46 and 47 can also be packaged on a roll of adhesive tape. Individual lengths of the tape may be cut to meet the length requirements of particular application. For example, a single strip of tape containing numerous MWM-Rosettes may be placed along a row of fasteners relatively rapidly. Electrical connections can be made to bond pads for the individual sensors or groups of sensors. When mounted against a surface, the adhesive can be provided along one surface of the supporting membrane to bond the selected length of the sensor array to a part to be tested. When mounted between layers, the adhesive should be provided along both the upper and lower exposed surfaces.

The sensors can also be embedded between layers of a structure, such as between layers of a lap joint or under repairs using composites or metal doublers, possibly with a sealant or other fillers to support compressive loads. This is illustrated in the cross-sectional view of FIG. 25 for MWM-Arrays 266 embedded in the sealant 262 between structural panels 260 and around a fastener 264. It also follows that the rosette configurations can be formed into "smart" washers that can be placed directly beneath the heads of fasteners. This is illustrated in the cross-sectional view of FIG. 26 for an MWM-Rosette 272 placed between the head of a fastener 270 and a structural panel 260. The sealant 262 may be placed between the structural panels, between the MWM-Rosette and the fastener head, or over the entire fastener head.

Since processing of the measured responses through the measurement grids provides the capability for each sensing element to be individually lift-off compensated and access to each element is not required for calibration, the sensor can be covered with a top coat of sealant to provide protection from any hazardous environments. Furthermore, the sensor can intentionally be set off a surface, or fabricated with a porous (or liberally perforated) substrate material, to avoid or minimize interference with the environment causing the corrosion process to occur on the surface and to provide continuous monitoring and inspection for stress corrosion cracking or corrosion fatigue.

Figure 28A:
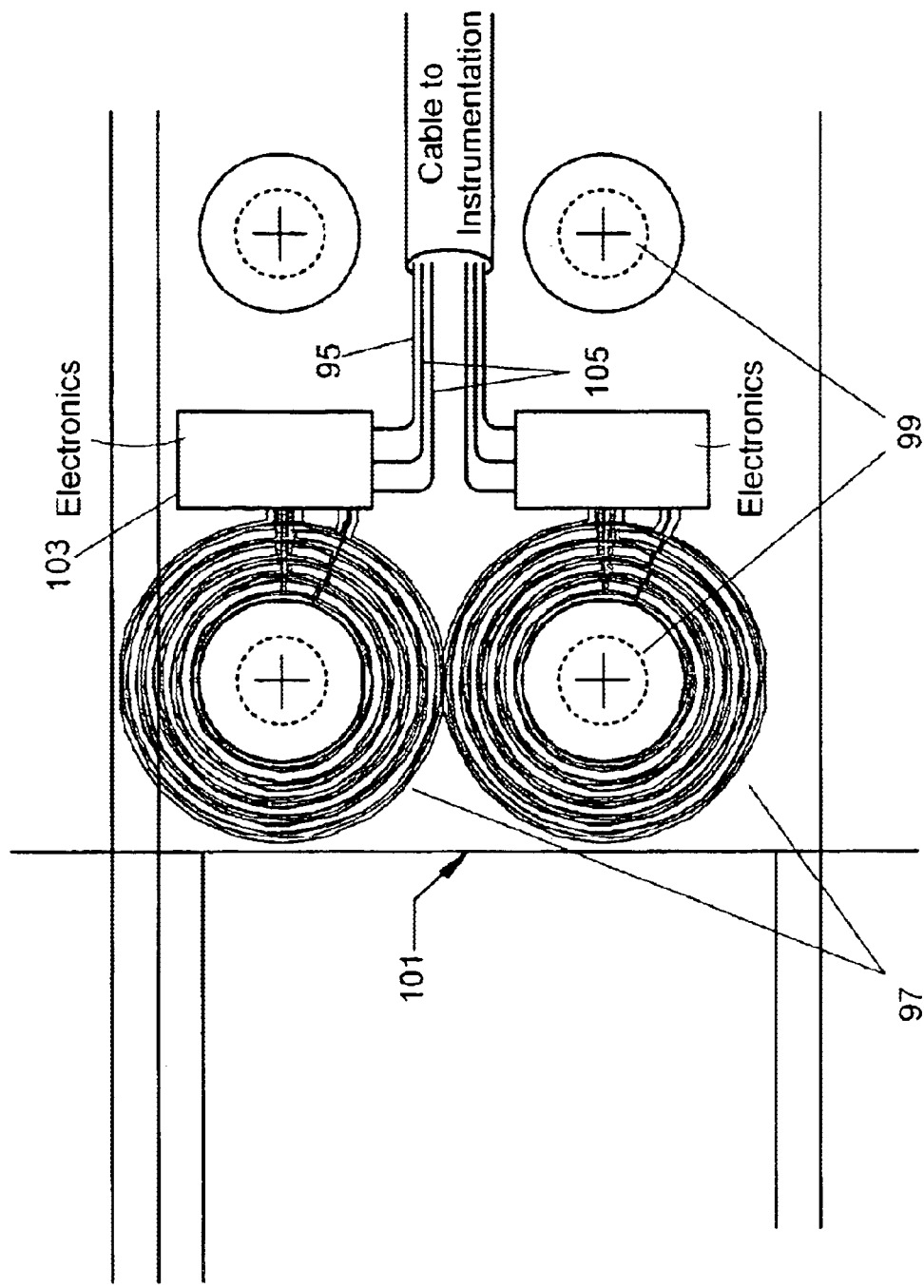
FIG. 28 is an illustration of a pair of MWM-Rosettes placed around fastener heads near a corner fitting.
FIG. 28b is an illustration of a pair of MWM-Rosettes placed around fastener heads with interconnected drive windings.
Figure 28B:
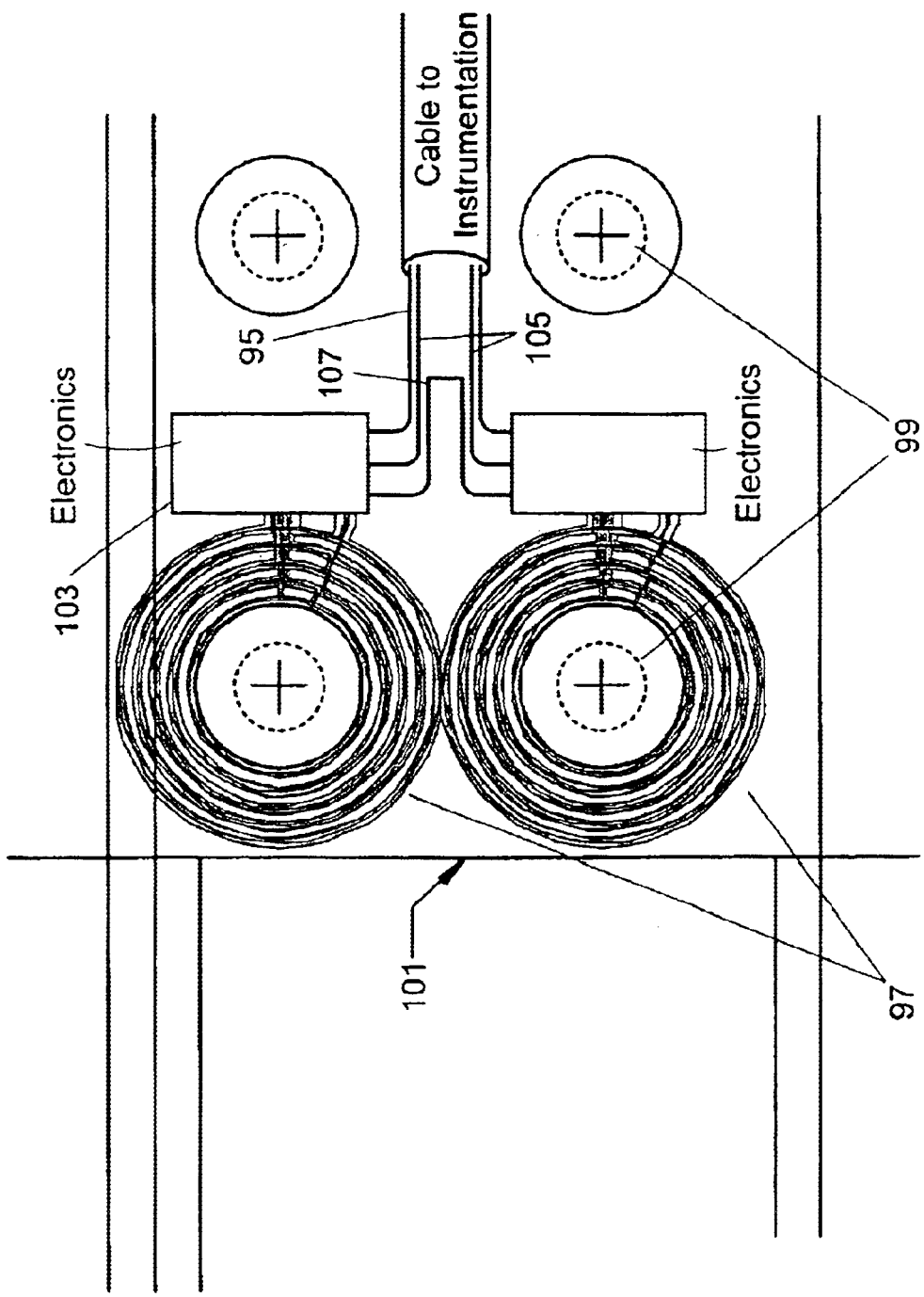

FIG. 28 illustrates an example configuration in which two closely spaced MWM-Rosettes 97 are placed around two fasteners 99. The fasteners are also near a corner fitting 101. This is meant to illustrate that the rosettes can operate when next to one another, and they can be driven either simultaneously or sequentially. The winding patterns for the primaries help cancel the magnetic fields outside the footprint of each sensor so that the cross-coupling of fields between rosettes is minimal. A distributed architecture can be used for the electrical connections to each of the rosettes. The electronics 103 can be distributed'so that each rosette has independent amplification and connection cables. Alternatively, multiplexing or parallel processing of each of the individual sensing elements, as appropriate, can reduce the number of independent amplifiers and cables. The electronics can be located near the sensing elements or at the opposite end of the connecting cables, far from the sensing elements, as necessary. In addition, the electronics can also be made flat and flexible for embedding in the structure so that relatively few signal and power line connections are required for each rosette. The cable to instrumentation can include separate connections 105 to the drive windings and connections 95 to the sense elements. The drive windings can also be connected together, with the example series connection 107 of FIG. 28b, to provide a common dive signal to the sensors.

These configurations, particularly when applied in a surface mount application, provide new capabilities for fatigue damage monitoring. For example, there is a stated requirement in both military and commercial sectors to more accurately determine the number of cycles to crack initiation, $N_i$, in fatigue test coupons and component tests. For coupons, this is necessary to determine the fatigue behavior of new alloys and to qualify production runs for materials used in aircraft structures. For fatigue tests of complex structures, determination of both the number of cycles to crack initiation and monitoring of crack propagation and crack propagation rates, da/dN (depth vs. cycles) and dl/dN (length vs. cycles), is required and would provide essential information for both aging aircraft management and newer aircraft design and modification. When cracks initiate in difficult-to-access locations, however, crack propagation rates can not be determined during fatigue testing. Thus, either costly disassembly is required during fatigue tests, or very conservative damage tolerance-based inspection scheduling for in-service aircraft will result. Surface mounting of the sensors substantially reduces the disassembly requirement and allows for more periodic inspections.

Figure 29:
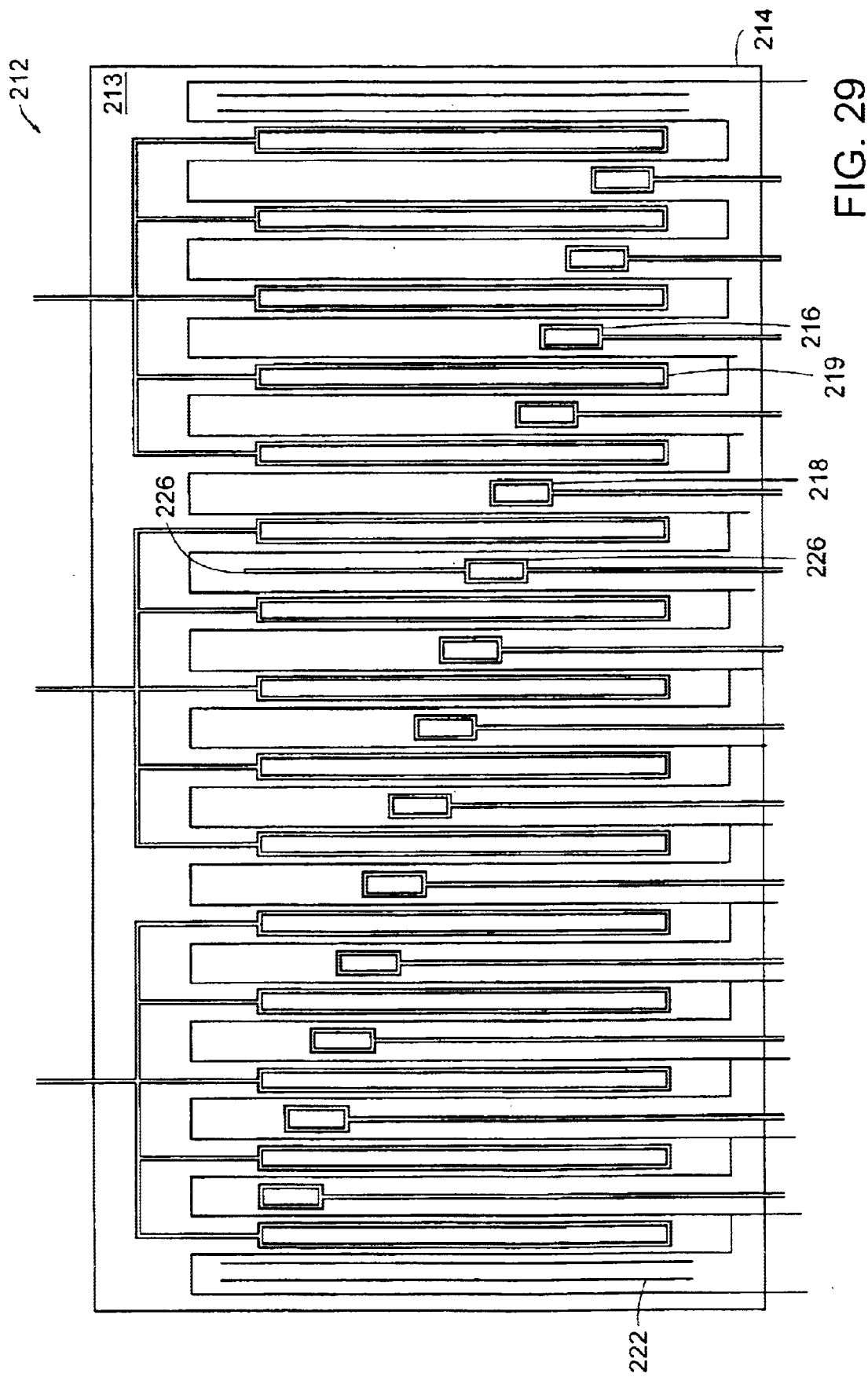
FIG. 29 is a schematic plan view of an MWM-Array with staggered positions of secondary elements. On one side the secondary elements are connected individually; the elements on the opposite side of the meandering primary are grouped or connected individually.
Figure 46:
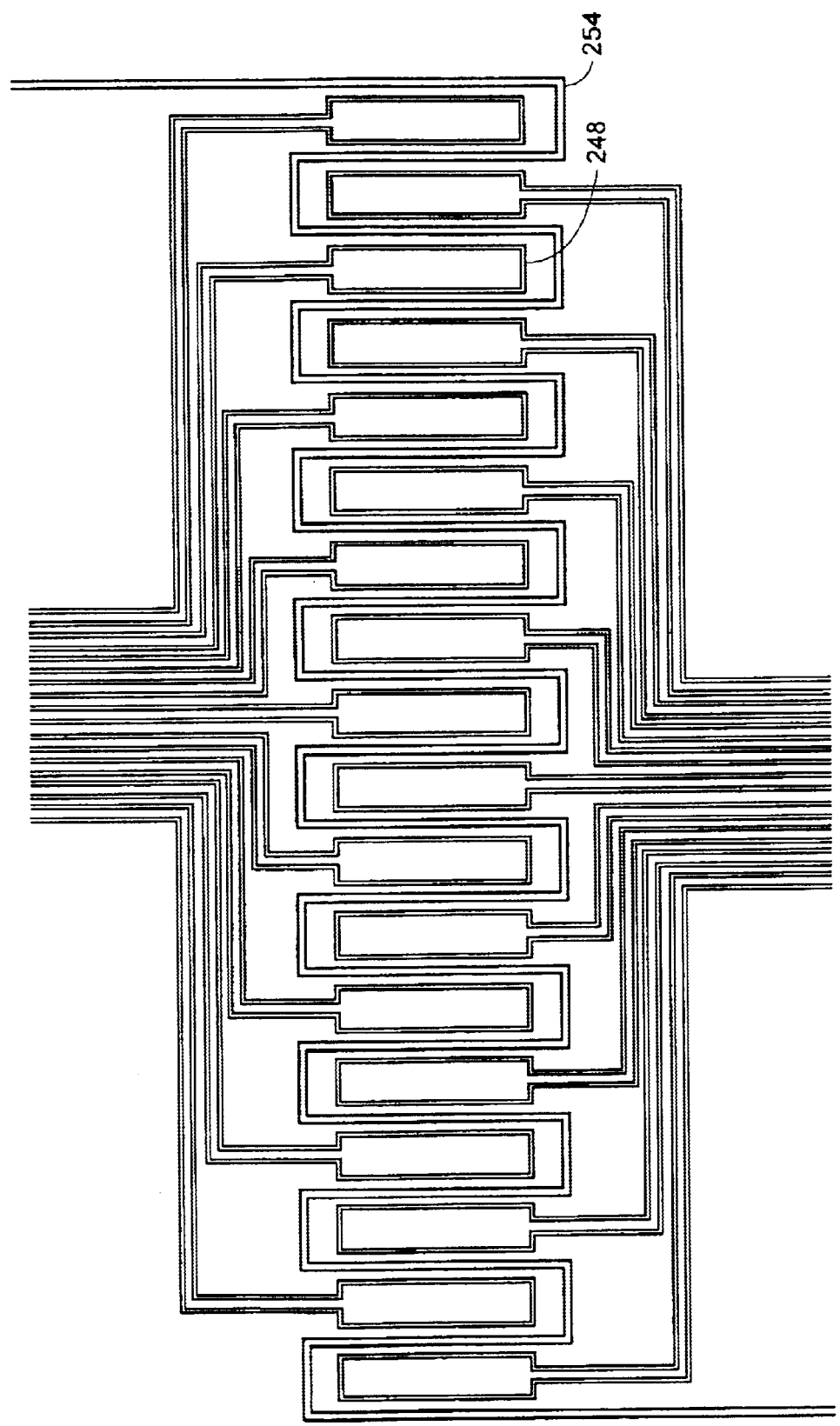
FIG. 46 is a plan view of an alternative embodiment for a linear sensor array.
Figure 47:
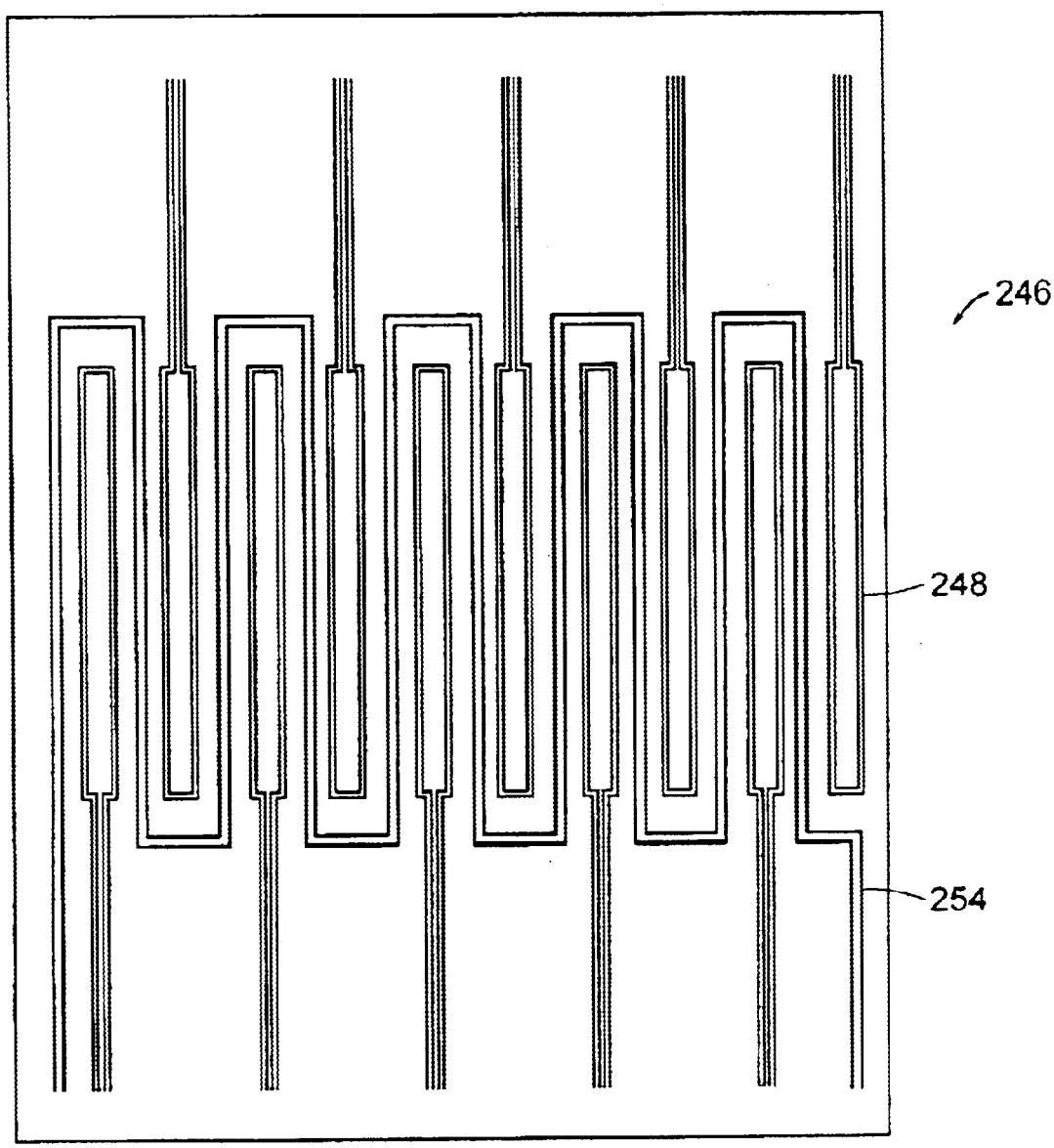
FIG. 47 is a plan view of an alternative embodiment for a linear sensor array.

FIG. 29 shows an alternative embodiment for a sensor 212 having a primary winding 214 and a plurality of sensing elements 216 mounted onto a common substrate 213. The sensing elements 218 of the sensing elements 216 on one side, those in the channels opening to the bottom of FIG. 29, are smaller sensing elements. The sensing elements 218 are offset, starting at the top on the left of FIG. 29. The offset is perpendicular to the scan direction to support image building of the "crack" response. The staggering of the secondary positions provides for complete coverage when the sensor is scanned over the MUT in a direction perpendicular to the primary meanders. Individual connections to each of the staggered secondary elements 216 also support the construction of images of the measured properties. Elongated extensions 226 to the secondary elements (224) can help to minimize variations in the parasitic coupling between the primary and the secondary elements. Dummy elements 222 can also be added to the endmost primary meanders, as taught in patent application Ser. No. 09/182,693. The elements 219 on the opposite side of the meandering primary are shown grouped and can be used to provide a measure of the background properties of the material which can complement the higher resolution property image obtained from the smaller sensing elements. FIG. 46 and FIG. 47 show two additional embodiments for linear sensor arrays where a single primary winding creates the imposed magnetic field and individual connections are made to each secondary element in the array.

Figure 30:
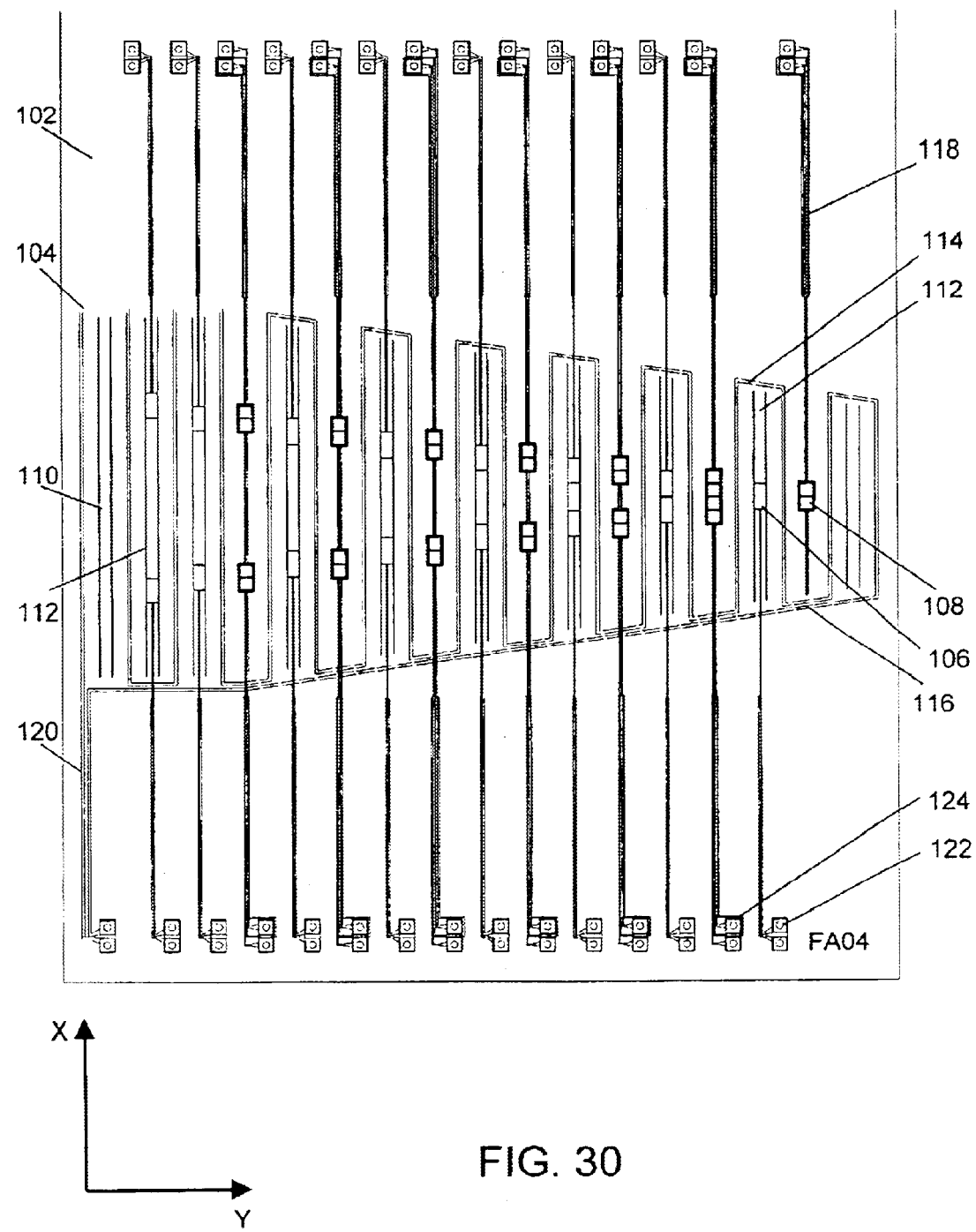
FIG. 30 shows a plan view of a tapered MWM-Array.

FIG. 30 shows a schematic for a multilayer sensor array that provides high imaging resolution and high sensitivity to hidden macrocracks and distributed microcracks. This deep penetration array design is suitable for the detection of hidden fatigue damage at depths more than 0.1 inches. The sensor array contains a single primary winding 104 and an array of secondary or sensing elements designed for absolute 106 or differential 108 measurements as described below with respect to FIGS. 31 and 32. In this tapered MWM-Array current flow through the primary winding creates a spatially periodic magnetic field that can be accurately modeled. The voltage induced in the secondary elements by the magnetic field is related to the physical properties and proximity to the MUT. Except for the rightmost sensing elements, two sensing elements are located within each meander of the primary winding. The absolute elements are offset in the x direction from other absolute elements to provide an overlap and complete coverage of the MUT when the array is scanned in the y direction. Similarly the differential elements are offset from one another to also provide complete coverage.

This sensor also uses a single primary winding that extends beyond the sensing elements in the x and y directions. This has the specific advantages of eliminating the problem of cross-coupling between individually driven sensing elements and reducing parasitic effects at the edges of the sensor. These parasitic effects are further reduced by the introduction of passive, dummy elements that maintain the periodicity of the sensor geometry. These elements are illustrated in FIG. 30 in the end meanders 110 and within the meanders containing the sensing elements 112.

Furthermore, the distance between the sensing elements and the primary (drive) winding is large enough to minimize coupling of short spatial wavelength magnetic field modes. As a result, the sensing element response is primarily sensitive to the dominant periodic mode. This produces improved depth of sensitivity to the properties of an MUT.

The design of the sensor in FIG. 30 also minimizes differences in coupling of the magnetic field to the sensing elements. The taper of the primary winding in the y direction maintains the distance between the sensing elements and the edge segments of the primary winding 114 and 116. This also effectively balances the fringing field coupling to the electrical leads 118 for connecting to the sensing elements. These leads are kept close together to minimize fringing field coupling. The leads for the primary winding 120 are kept close together to minimize the creation of fringing fields. The bond pads 122 and 124 provide the capability for connecting the sensor to a mounting fixture. The trace widths for the primary winding can also be increased to minimize ohmic heating, particularly for large penetration depths that require low frequency and high current amplitude excitations.

In order to maintain the symmetry for the sensing elements, multiple layers are required for the winding patterns. In FIG. 30 the primary winding is fabricated on one side of an electrical insulator 102 while the secondaries are deposited onto the opposite side of the insulator. The three-layer structure is then sandwiched between two additional layers of insulation, with adhesives bonding the layers together. This deposition can be performed using standard microfabrication techniques. The insulation used for the layers may depend upon the application. For conformable sensors, the insulating layers can be a flexible material such as Kapton™, a polyimide available from E. I. DuPont de Nemours Company, while for high temperature applications the insulating layers can be a ceramic such as alumina.

Although the use of multilayer sensors and sensor arrays is widespread in the literature, one unique approach here is the offset combination of absolute and differential elements within a meandering winding structure that provides a spatially periodic imposed magnetic field and has been designed to minimize unmodeled parasitic effects. Specific advantages of this design are that (1) it allows complete coverage with both types of sensing elements when the array is scanned over an MUT, (2) the response of the individual elements can be accurately modeled, allowing quantitative measurements of the MUT properties and proximity, and (3) it provides increased depth of sensitivity. In particular, while U.S. Pat. No. 5,793,206 teaches of the use of numerous sensing elements within each meander of a primary winding, the design of FIG. 30 illustrates how the layout of the primary and secondary windings can provide improved measurement sensitivity.

Figure 31:
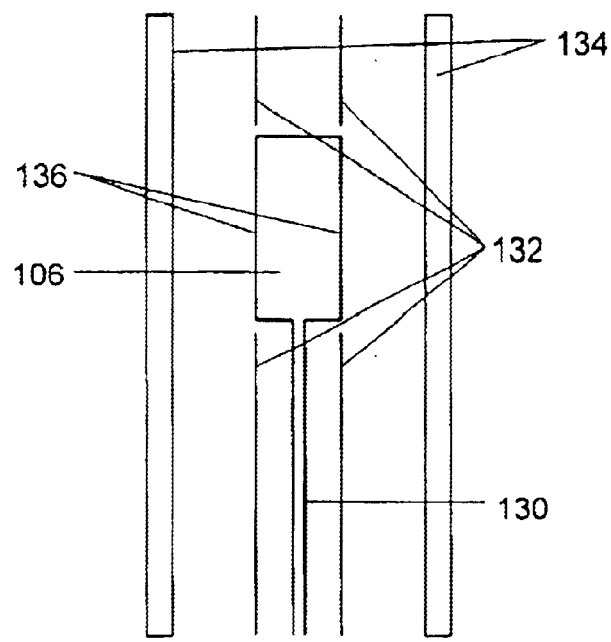
FIG. 31 shows an expanded view of an absolute sensing element.

FIG. 31 shows an expanded view of one of the absolute sensing elements 106. Electrical connections to the sensing loop are made through the leads 130 and the bond pads 122.

The dummy elements 132 maintain the periodicity of the winding structures and reduce element to element variability. The distance between the primary winding segments 134 and the secondary winding segments 136 can be adjusted to improve measurement sensitivity, as described in patent application Ser. No. 09/182,693. It is particularly advantageous to have this distance as large as possible when attempting to detect deep defects, far from the surface. With each absolute sensing element independent of the response of the other elements, the measured signal can be processed with measurement grids, as described in U.S. Pat. No. 5,543,689, to independently measure the local material property and proximity to the MUT. The measured properties from each absolute sensing element can then be combined together to provide a two-dimensional mapping of the material properties.

Figure 32:
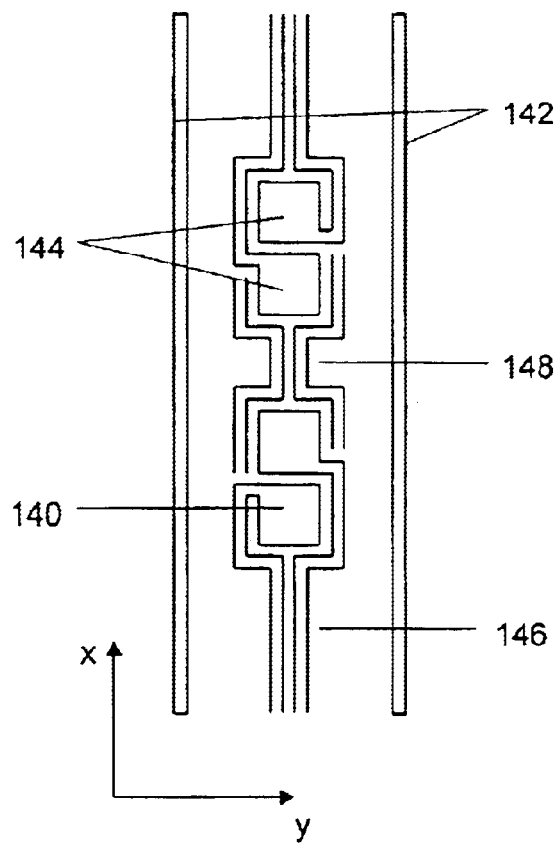
FIG. 32 shows an expanded view of a differential sensing element.

FIG. 32 shows an expanded view of two differential sensing elements 140 placed adjacent to one another, between two primary windings 142. Each differential element includes two sensing coils 144 with associated connection leads 146. The meandering pattern of the leads provides essentially the same coupling areas and fields across the sensing region between the sensing coils. Dummy elements 148 are placed on the sides and between the pairs of differential coils closest to the center of the sensor in the x direction to further minimize any differences between the coils. By maintaining the symmetry between the coils and the sensing leads, the coil differences can be taken at the bond pads 124 or with electronics external to the sensor itself Similar to the absolute coils, the gap spacing between the primary windings and the secondary coil can be adjusted and optimized for a particular measurement application. When scanned in the y direction, the offset of these elements in the x direction provides the capability for creating a two-dimensional mapping of the differential response, which indicates local variations in the material properties and proximity.

Figure 33:
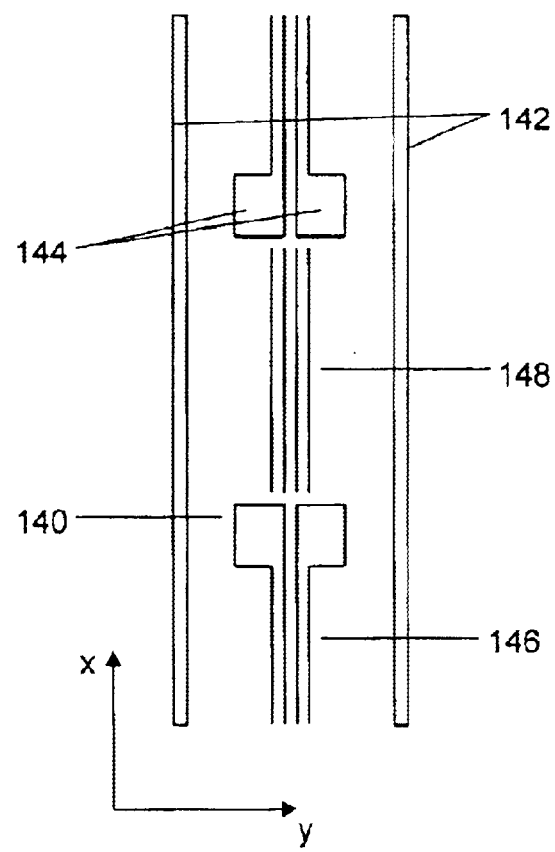
FIG. 33 shows an expanded view of a differential sensing element.

FIG. 33 shows an alternative orientation for the differential sensing elements 140 between the primary windings 142. In this case, the individual windings 144 of the sensing elements are placed symmetrically on opposite sides of the centerline between the primary windings and perpendicular to the extended portions of the primary windings. In this orientation the differential response is parallel to the scan direction for the sensing array.

This combination of both differential and absolute sensing elements within the same footprint of a meandering primary winding is novel and provides new imaging capabilities. The differential elements are sensitive to slight variations in the material properties or proximity while the absolute elements provide the base properties and are less sensitive to small property variations. In one embodiment, the raw differential sensor measurements can be combined with one, some or all of the raw absolute measurements to provide another method for creating a two-dimensional mapping of the absolute material properties (including layer thicknesses, dimensions of an object being imaged, and/or other properties) and proximity. In another embodiment, the property and proximity information obtained from the absolute measurements can be used as inputs for models that relate the differential response to absolute property variations.

Figure 34:
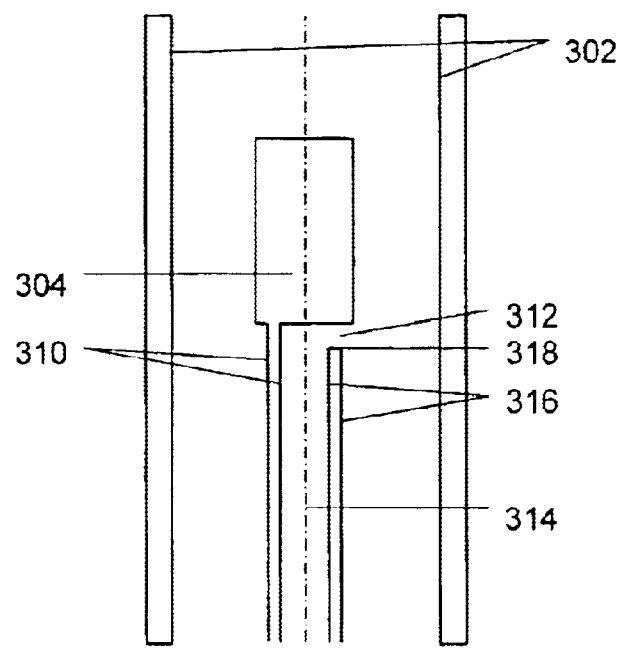
FIG. 34 shows an alternative method for connecting to an absolute sensing element.

FIG 34 shows an expanded view of an alternative method for connecting to an absolute sensing element 304. Electrical connections to the sensing loop are made through the leads 310, which are offset from the centerline 314 between adjacent conductors for the primary winding 302. A second set of leads 316 are offset the same distance from the centerline on the other side of the centerline and connected together to form a flux linking loop with conductor 318. The connection leads 310 to the sensing element are then connected to the second set of leads 316 in a differential format to so that the flux linked by the second set of leads essentially subtracts from the flux linked by the leads to the sensing element. This is particularly useful when the sensing elements are made relatively small to provide a high spatial resolution and the flux (or area) linked by the loop created by the connection leads becomes comparable to the flux (or area) of the sensing element. The distance 312 between the cross-connection 318 on the second set of leads and the sensing element should be minimized to ensure that the flux linked by the connection leads is nearly completely canceled. Dummy elements can also be used, as illustrated in FIG. 31, to help maintain the periodicity of the conductors.

Figure 35:
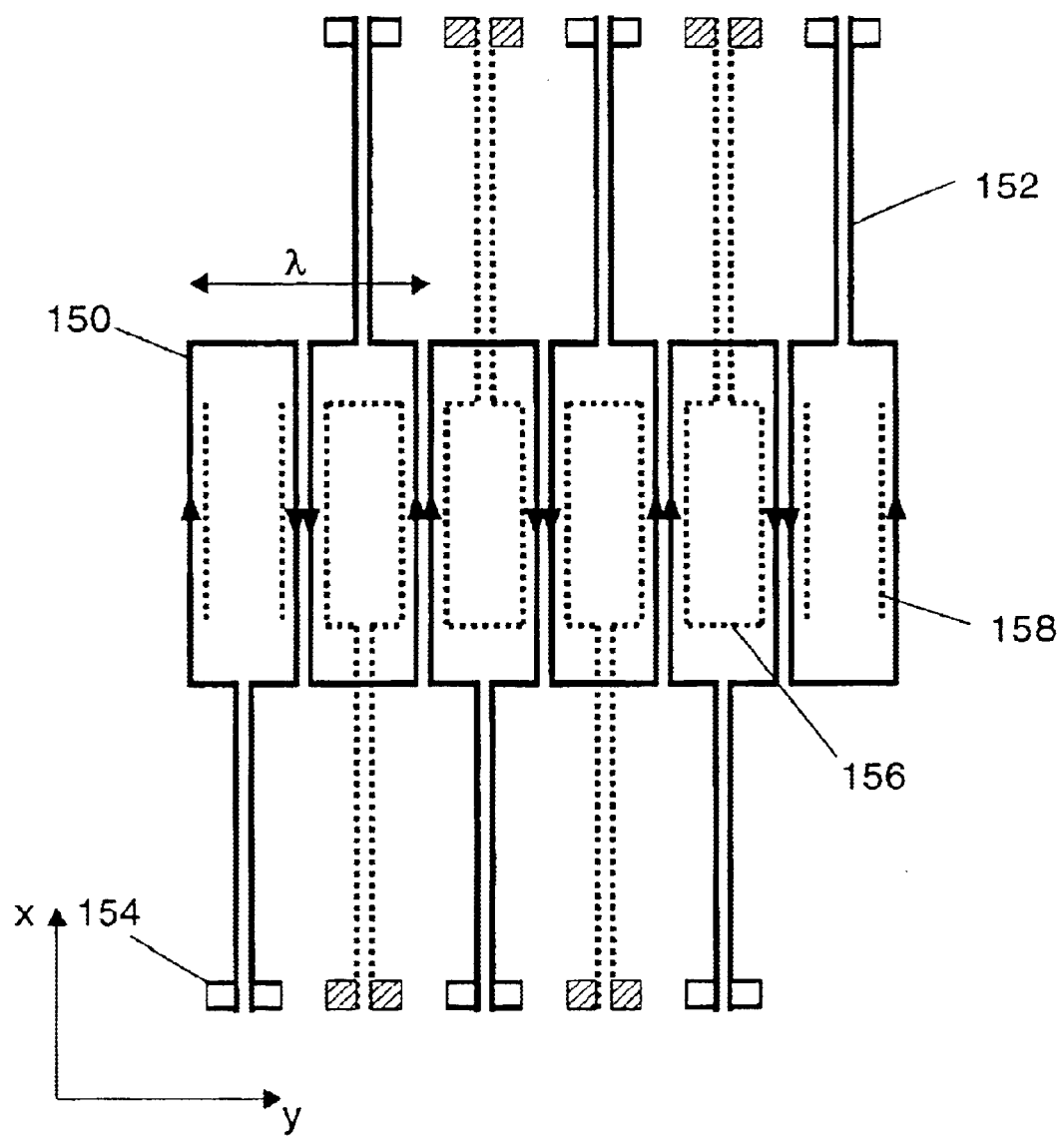
FIG. 35 illustrates an alternative design for a meandering primary winding.

One of the issues with planar eddy-current sensors is the placement of the current return for the primary winding. Often the ends of the primary winding are spatially distant from one another, which creates an extraneous and large inductive loop that can influence the measurements. One embodiment for a layout for a primary winding that reduces the effect of this inductive loop is shown in FIG. 35. The primary winding is segmented with the width of each segment 150 determining the spatial wavelength $\lambda$. The segments of the primary winding are connected to bond pads 154 through leads 152, where the leads are brought close together to minimize the creation of stray magnetic fields. After wrapping the leads and bond pads behind the face of the primary winding, the individual segments are then connected together in series. The arrows then indicate the instantaneous current direction. The space behind the sensor array can be filled with rigid insulators, foam, ferrites, or some combination of the above. This three-dimensional layout for the sensor effectively creates a meandering winding pattern for the primary with effectively twice the current in the extended portions of each segment and moves the large inductive loop for the primary winding connections far from the sensing region. The sensing elements 156 and dummy elements 158 are then placed in another layer over the primary winding. This design can also be applied to the tapered MWM array format of FIG. 30, where the primary windings become trapezoidal loops.

Figure 36:
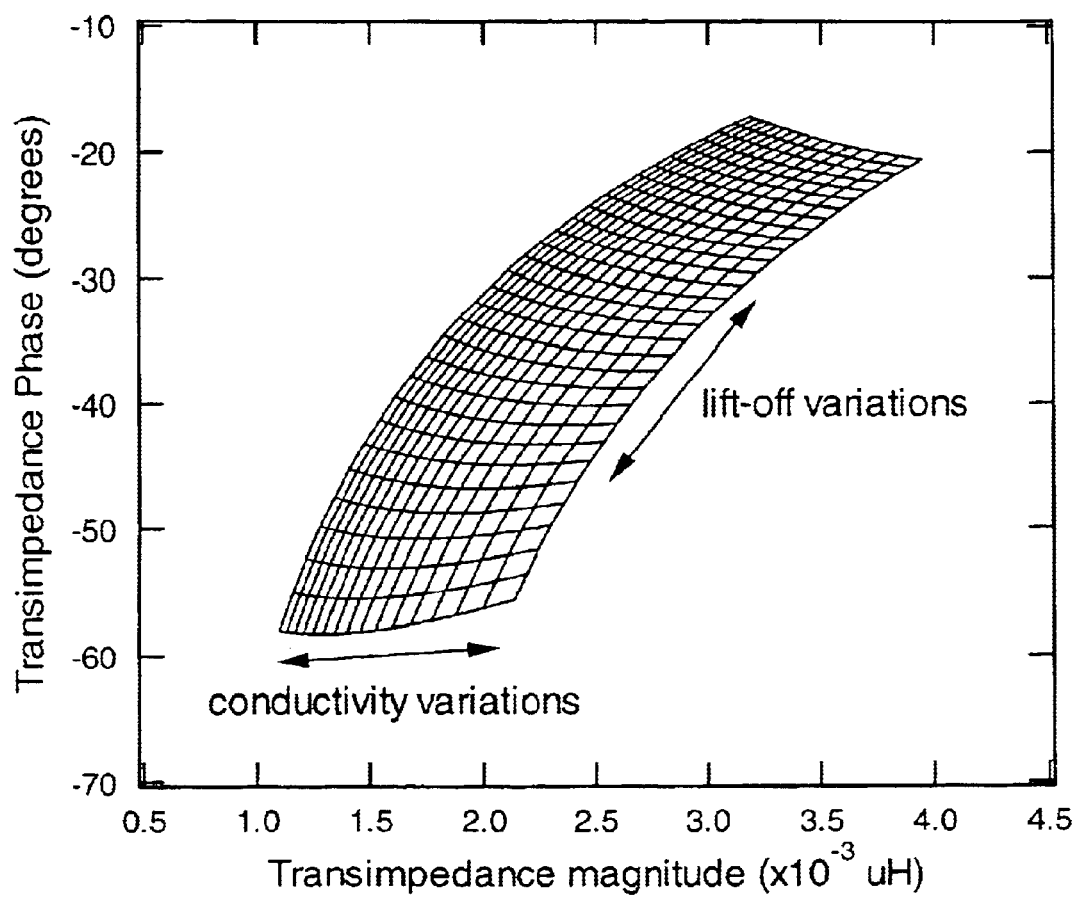
FIG. 36 shows a measurement grid for a layered winding design.

Grid measurement methods can also be applied to multi-layer sensor constructs. For example, FIG. 36 shows a measurement grid for the two layer MWM sensor of FIGS. 38a and 38b. This measurement grid provides a database of the sensor response (the transimpedance between the secondary winding voltage and the primary winding current) to variations in two parameters to be determined. In FIG. 36, these parameters are the lift-off and the test material conductivity. The sensor response values are typically created with a model which iterates each parameter value over the range of interest to calculate the sensor response, but in circumstances where extensive reference parts are available which span the property variations of interest, empirical responses can be used to create the grids. After measuring the sensor response on a test material, the parameter values are determined by interpolating between the lines on the measurement grid.

Figure 37:
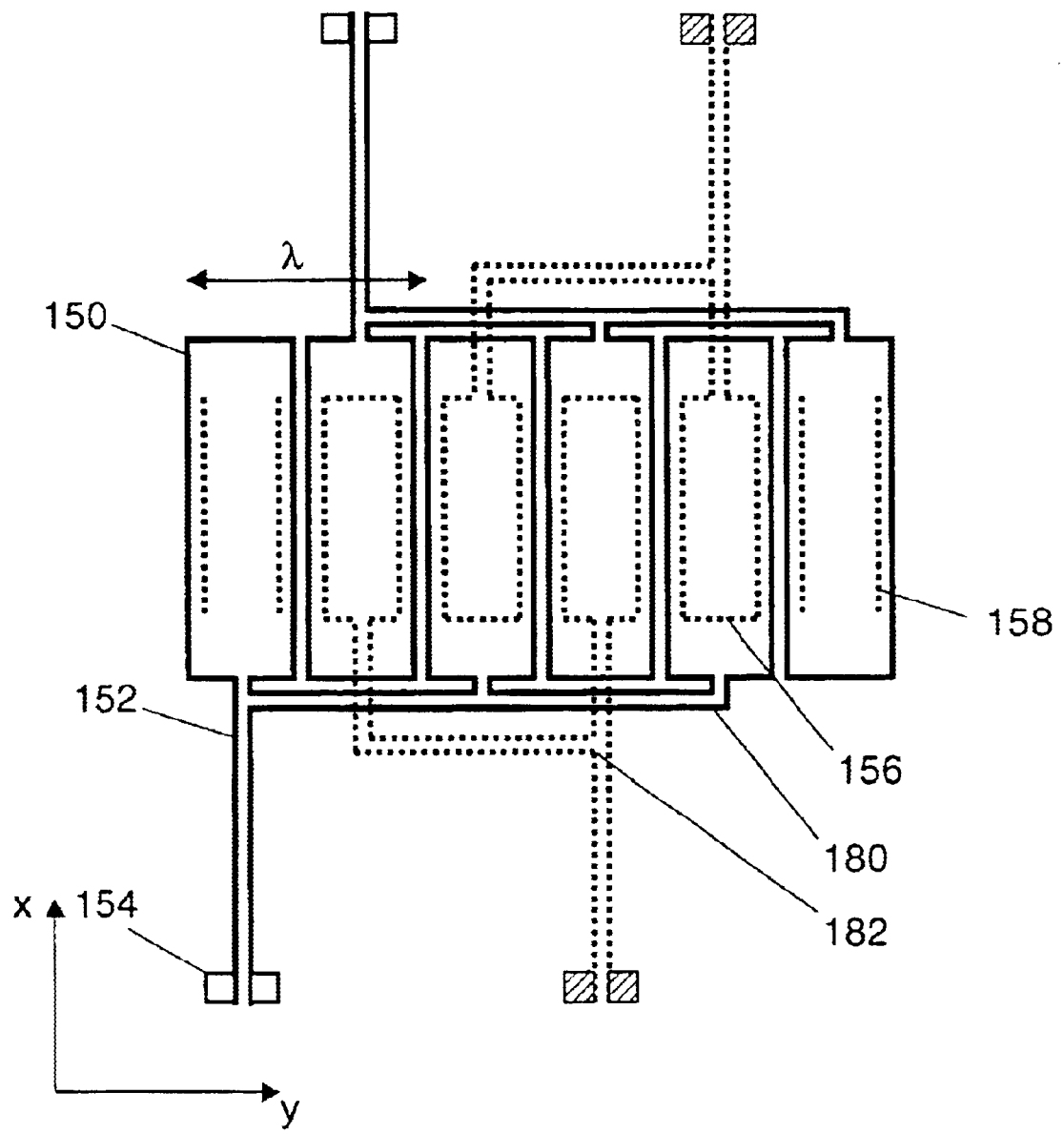
FIG. 37 illustrates a design for cross-connecting the meanders of the primary winding which greatly reduces the necessary number of bond pad connections.
Figure 38A:
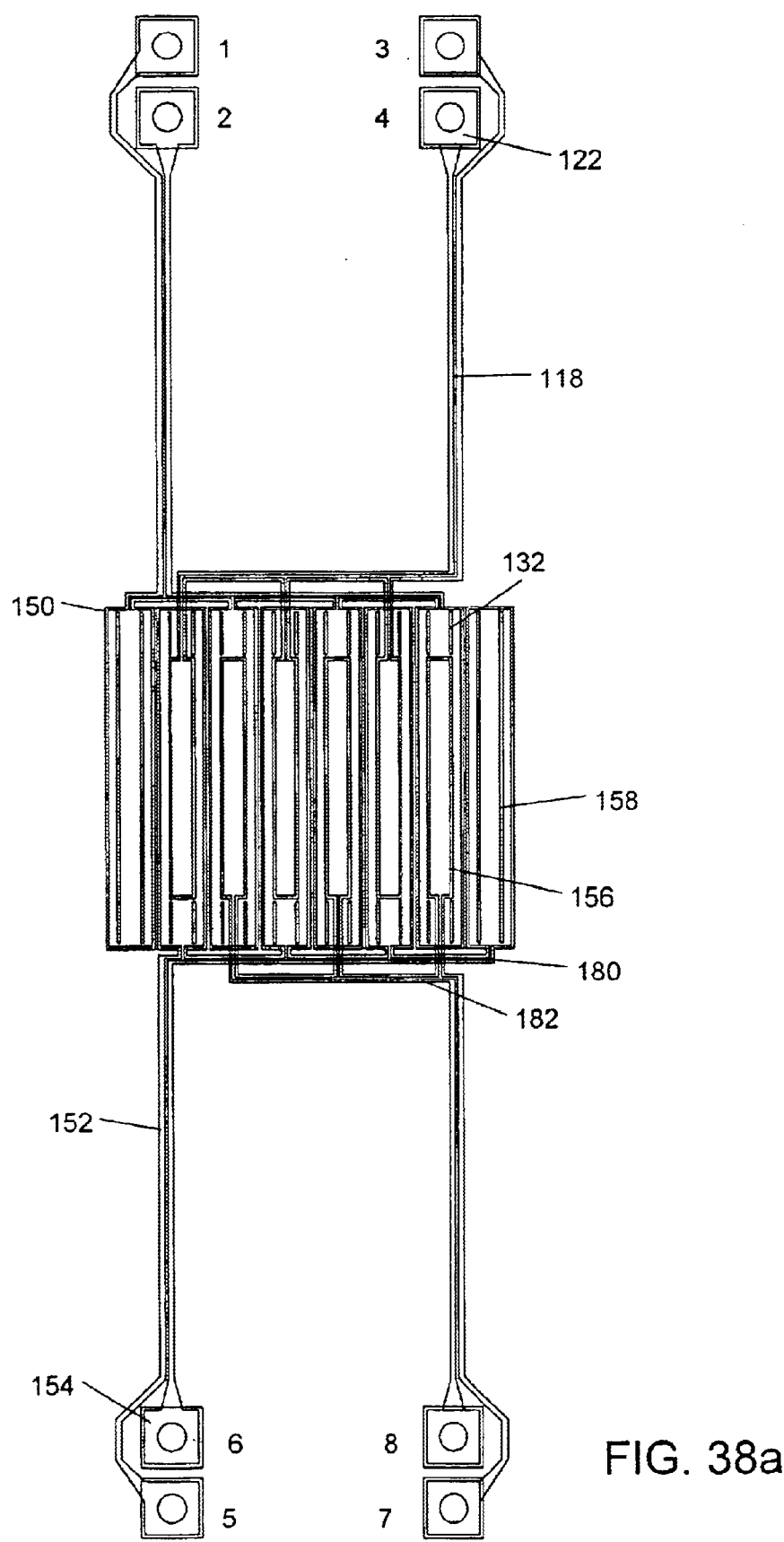
FIG. 38 is (a) a plan view of a multi-layer electrode geometry and (b) an expanded view of the winding segments.
Figure 38B:
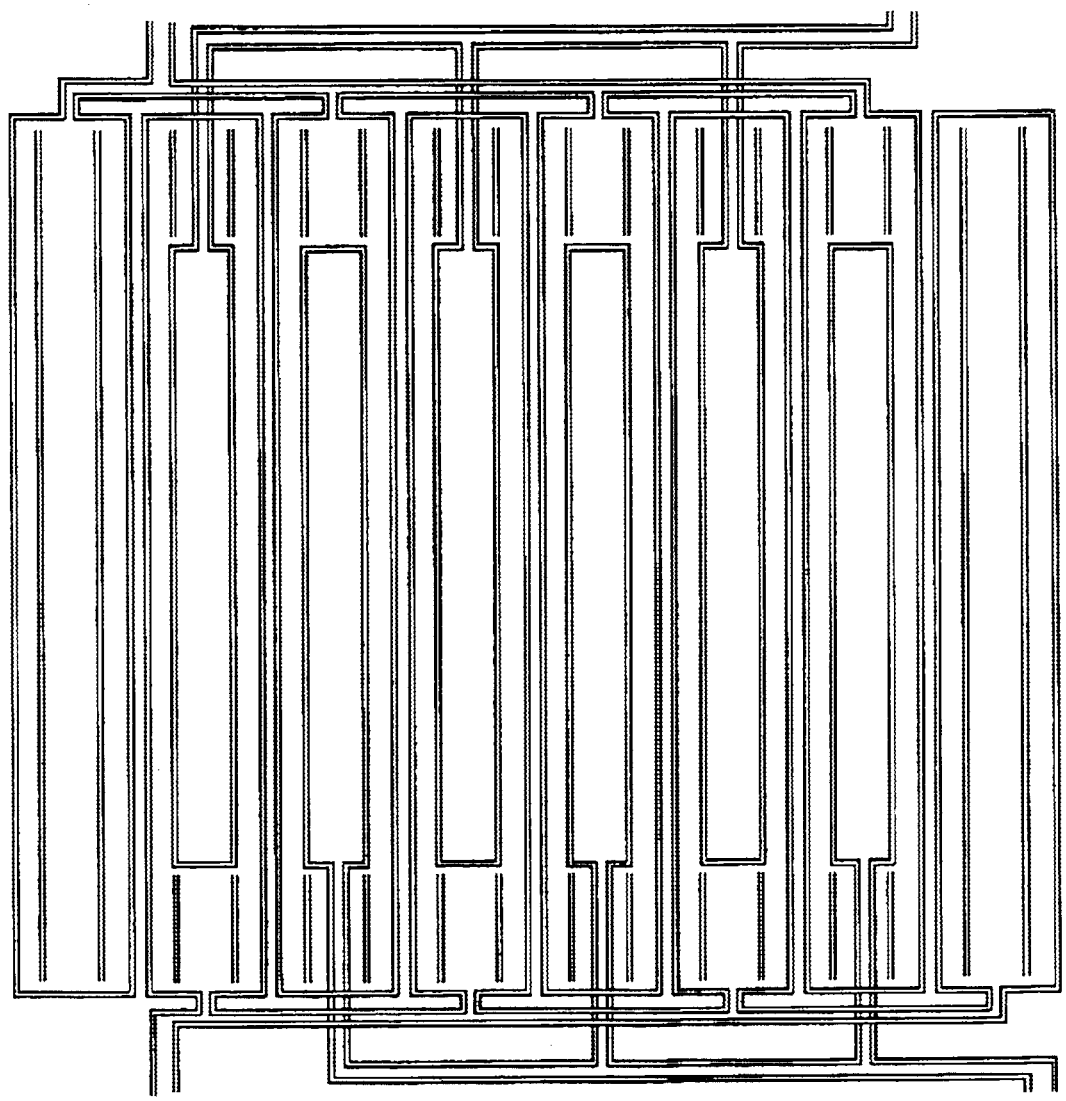

An alternative method of making connections to the various components of the primary winding elements is shown in FIG. 37. In this case, the cross-connections 180 between the various segments of the primary winding reduces the number of bond pad connections 154 for the primary windings. This greatly simplifies the electrical connections to the sensor as only four bond pads are required, independent of the number of meanders in the footprint of the sensor. The same concept can be applied for the secondary elements, as the connections 182 indicate. This is useful whenever a combination of secondary elements is desired or independent connections to each of the secondary elements is not required. FIGS. 38a and 38b illustrate another example of the "split" primary winding design. Dummy elements 132 near the ends of the sensing elements are also included in this case. Furthermore, the dummy elements 158 are extended along almost the entire length of the primary winding loops in order to maintain the design symmetry.

Figure 39:
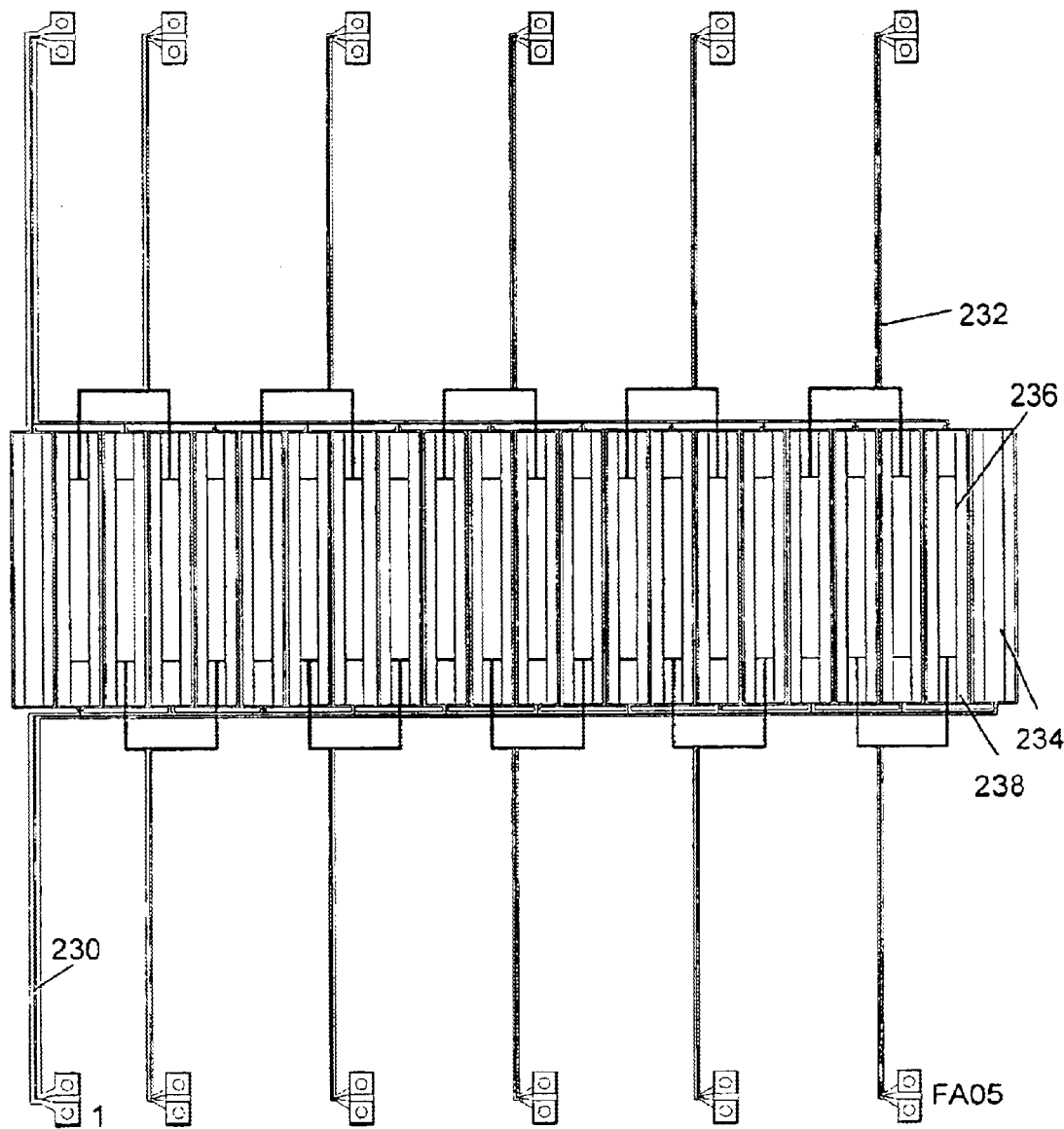
FIG. 39 is a plan view of a sensor similar to that shown in FIG. 38, except the grouping of sensing elements cover different sections of the meandering primary footprint.

An embodiment of an MWM-Array with multiple sensing elements is shown in FIG. 39. The primary winding meanders 230 have connections similar to the primary shown in FIGS. 38a and 38b. Secondary element connections 232 are made to groups of secondary elements 236 that span different regions of the primary winding structure so that scanning of the array over an MUT in a direction parallel to the meanders of the primary provide measurements of spatially distinct areas. Dummy elements 234 and 238 help minimize parasitic coupling between the primary and secondary elements to improve air calibrations.

Figure 40:
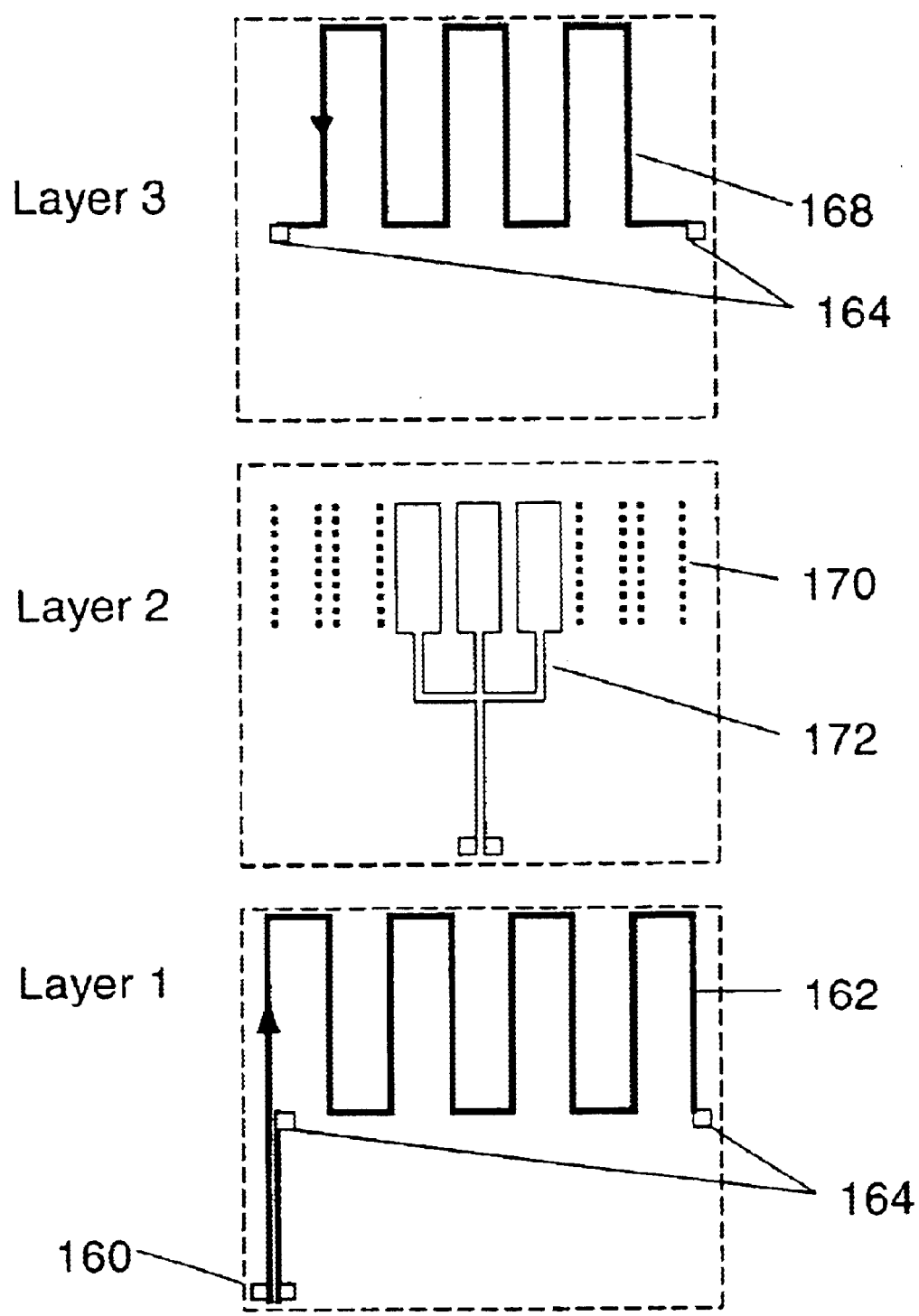
FIG. 40 is a schematic plan for a layered primary winding design.

Another embodiment for a layout of the planar primary winding reduces the effect of the primary winding inductive loop as illustrated in FIG. 40. The sensing windings 172 with dummy elements 170 are sandwiched between a meandering winding 162 in the first layer and a second meandering winding 168 in the third layer, with electrical insulation between each layer. Vias 164 between the first and third layers provide an electrical connection between the meanders. The connections to the primary are made at the bond pads such as 160. When stacked together, the current in the primary winding is effectively twice the current of a single layer primary winding.

It is also possible to calibrate and verify the integrity of the surface mounted MWM-Arrays by utilizing the accurately modeled and reproducible array geometry and measurement grids so that extensive sets of reference parts are not required. An initial "air" calibration is performed prior to mounting on the surface. This involves taking a measurement in air, for each array element, and then storing the calibration information (e.g., in a computer) for later reference after mounting the sensors. After the sensor has been mounted to a surface, the instrument and probe electronics can be calibrated by connecting to a duplicate sensor so that an air calibration can be performed. After connecting the surface mounted sensor to the instrumentation, the sensor operation and calibration can be verified by measuring the lift-off at each element. The sensor is not operating properly if the lift-off readings are too high, which may result from the sensor being detached from the surface, or if the measurement points no longer fall on a measurement grid, which generally corresponds to a lack of continuity for one of the windings. A final verification involves comparing baseline measurements to other measurement locations that are not expected to have fatigue damage or cracks. This reference comparison can verify sensor operation and may assist in compensating for noise variables such as temperature drift. This may involve using elements of the array that are distant from the areas of high stress concentration.

Figure 41:
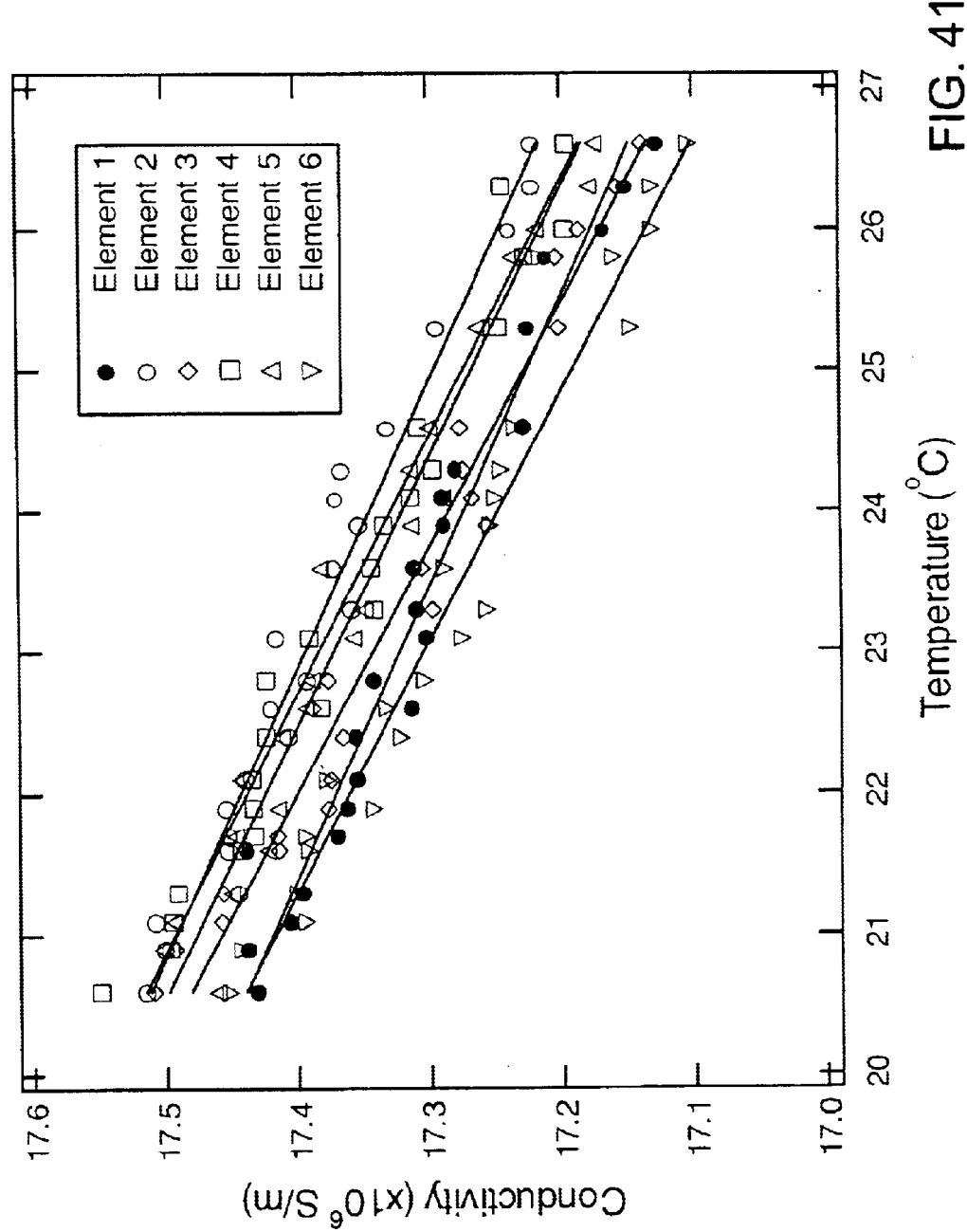
FIG. 41 is an illustration of the temperature dependence of the MWM measured electrical conductivity.

The electrical conductivity of many test materials is also temperature dependent. This temperature dependence is usually a noise factor that requires a correction to the data. For example, FIG. 41 shows a representative set of conductivity measurements from the elements of the MWM-Array of FIG. 8 inserted inside a hole in a fatigue test coupon as the coupon temperature is varied and monitored with a thermocouple. The MWM was designed to be insensitive to variations in its own temperature, as described in U.S. Pat. Nos. 5,453,689 and 5,793,206 and U.S. patent application Ser. No. 09/182,693. The temperature of the component can be changed in a variety of ways: with the ambient conditions in the room, with the mechanical loading as the component is fatigued, by grasping it with a hand, and by blowing a hot or cold air jet across it. FIG. 41 shows that the conductivity has an essentially linear temperature dependence, over this range of temperatures, so that conductivity measured by each element can be corrected for temperature drift.

Thermally induced changes in the electrical conductivity also provide a mechanism for testing the integrity of the sensor. Heating the test material locally, in the vicinity of the MWM-Array should only lead to a change in conductivity, not lift-off, when the array is compressed against the part. Monitoring the conductivity changes with temperature, without significant lift-off changes then verifies the calibration of the sensor and also that the sensor elements themselves are intact.

Another component of the life extension program for aircraft is the rapid and cost-effective inspection of engine components such as the slots of gas turbine disks and spools. Cracks often form in regions of fretting damage. The fretting damage often leads to false positive crack detections with conventional eddy-current sensors, which severely limits the usefulness of conventional eddy-current sensors in this inspection. For a number of disks/spools, ultrasonic (UT) inspection is the current standard inspection method. The current UT threshold for "reliable" detection of cracks in fretting damage regions is thought to be between 0.150 and 0.250 inches but there is an ongoing need to reliably detect smaller cracks, possibly as small as 0.060 to 0.080 inches in length. The JENTEK GridStation(System with the conformable MWM eddy-current sensor and grid measurement methods offers the capability to detect these small cracks in fretting regions, while eliminating the need for crack calibration standards other than to verify performance. Calibration can be performed with the sensor in the middle of any slot on the engine disk. A scan of this slot is then performed first to verify that no crack existed at the calibration location. Then all slots on a disk are inspected without recalibration.

Figure 42A:
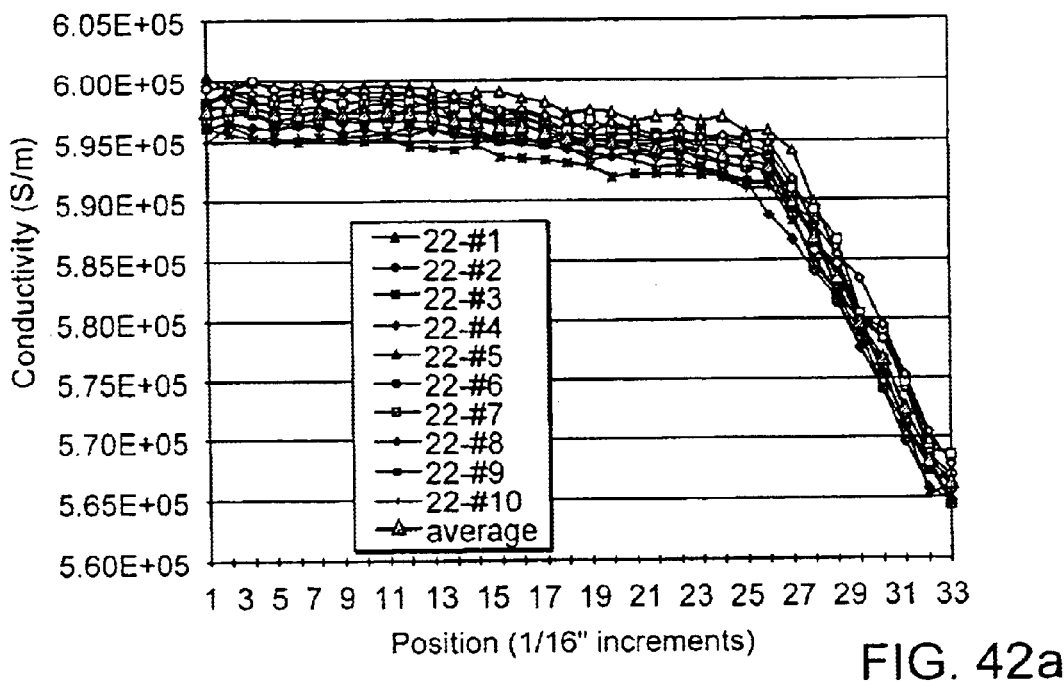
FIG. 42 is an illustration of the absolute conductivity data from repeated MWM scans in slots (a) 22 and (b) 23 of a Stage 2 fan disk.
Figure 42B:
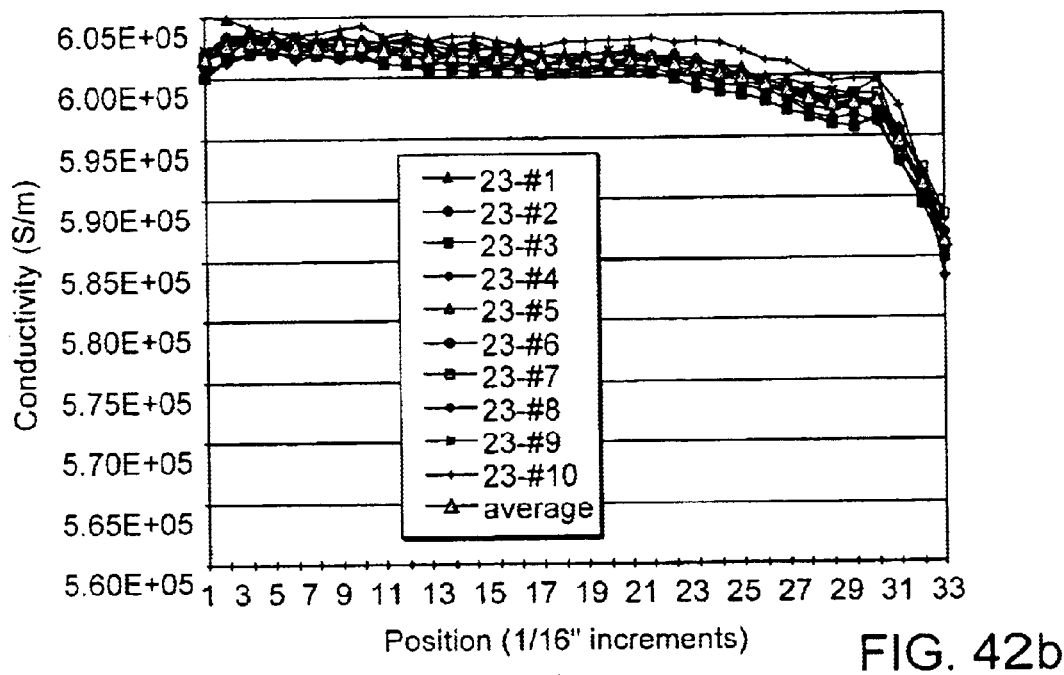

For the inspection of nonmagnetic disks, such as titanium disks, absolute electrical conductivity and proximity (lift-off) measurements can be performed with MWM sensors. When a crack within a slot is encountered, it manifests itself by a distinct and repeatable drop in conductivity. FIGS. 42a and 42b shows an example of repeated inspections on the same slots for a Stage 2 fan disk. No calibration standards were used to perform these inspections. At the start of the inspection, a selected area within a single slot (near the middle) was used for reference calibration and was the only calibration required for the inspection of all of the slots. The inspection consisted of scanning each slot with the MWM probe along the entire length to within approximately 0.08 inches from the edge. These scans can be performed in an incremental mode, where the sensor positioned is moved in increments of 1 to 2 mm, or in a continuous mode, where a position encoder automatically records the sensor position as the sensor is moved along the slot.

Figure 43:
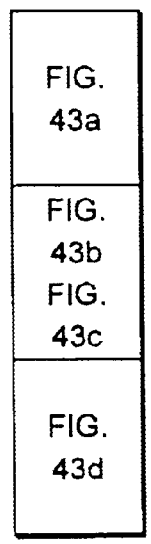
FIG. 43 is an illustration of the absolute conductivity data from MWM scans in all 46 slots in a Stage 2 fan disk. Arrows indicate slots that had cracks detected by the MWM and UT. Encircled slot numbers denote cracks detected by the MWM but not UT.
Figure 43A:
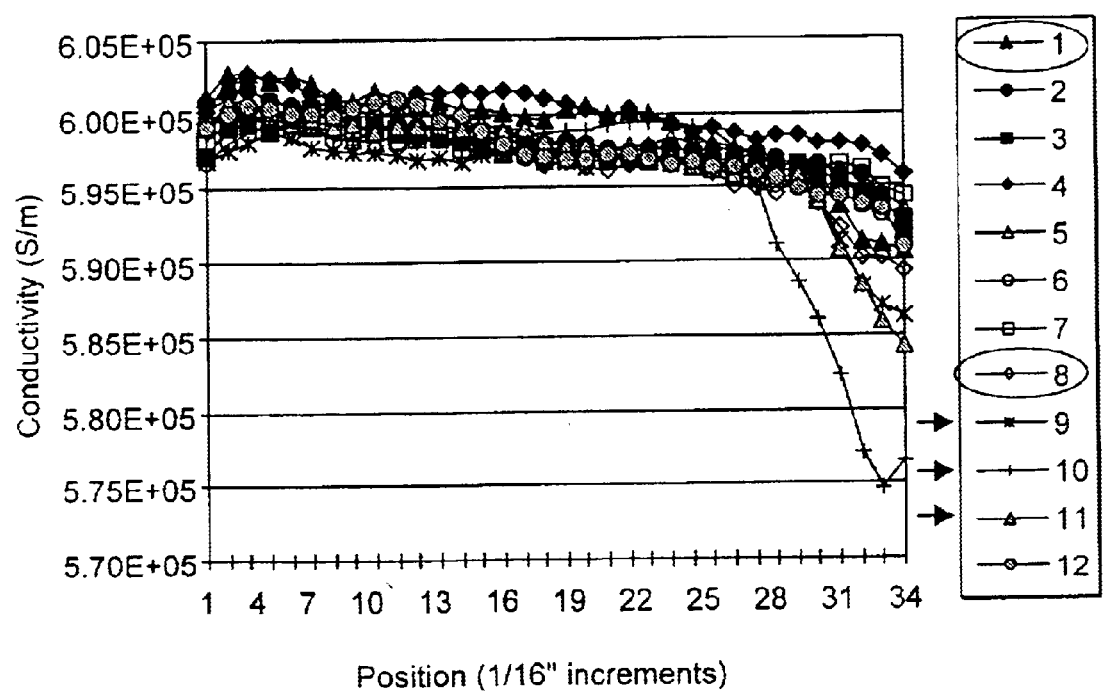
Figure 43B:
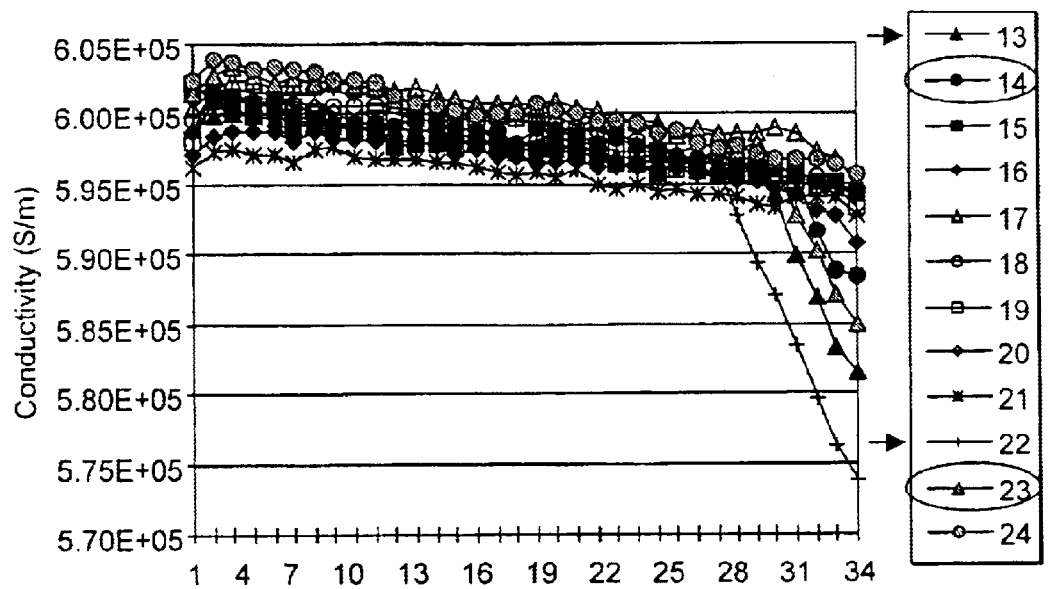
Figure 43C:
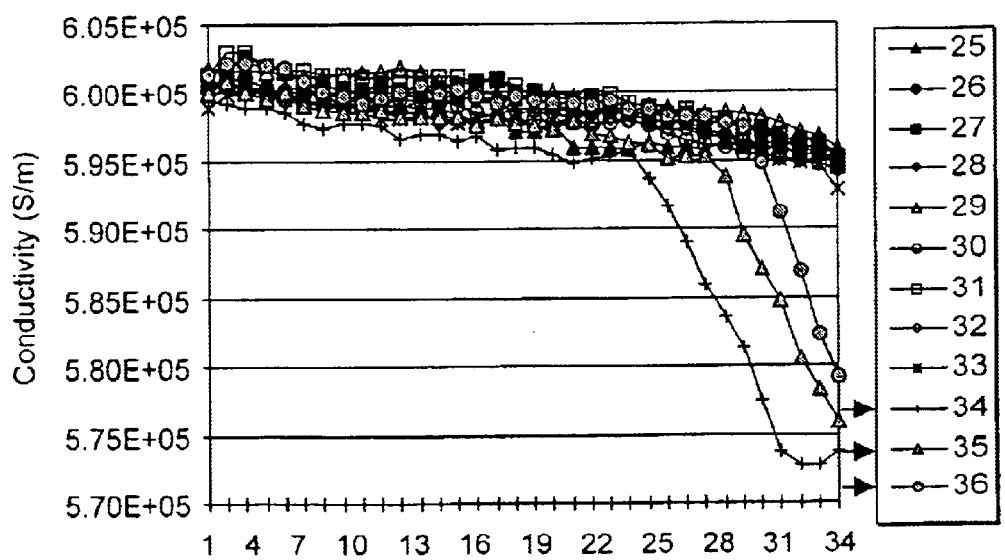
Figure 43D:
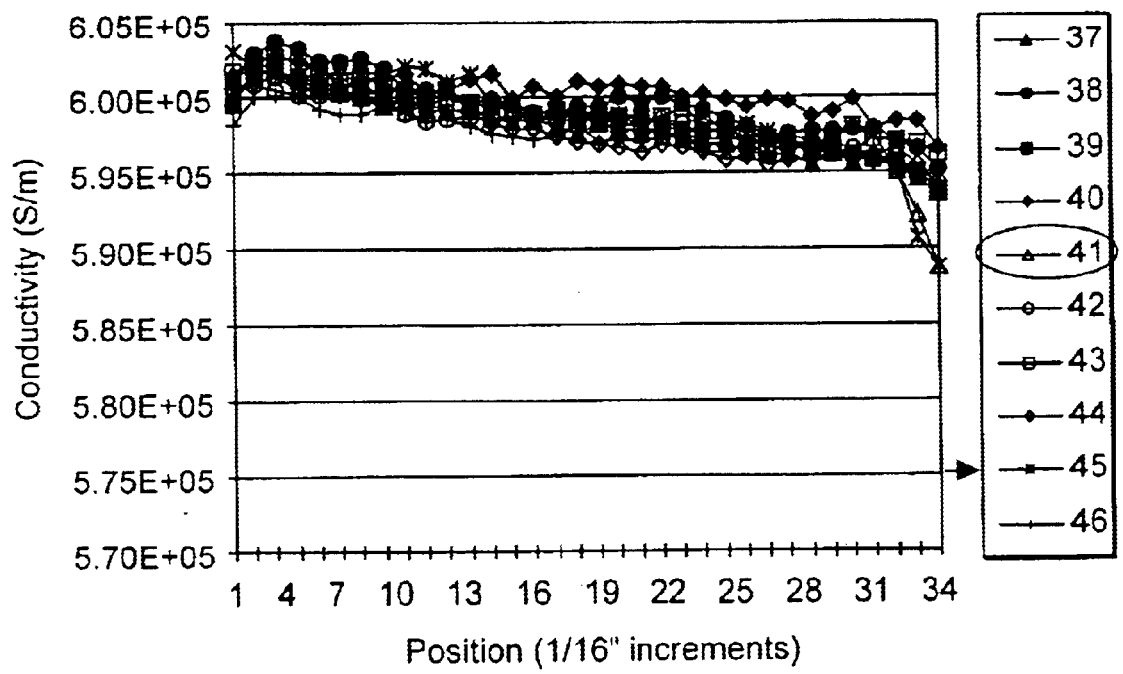
Figure 44:
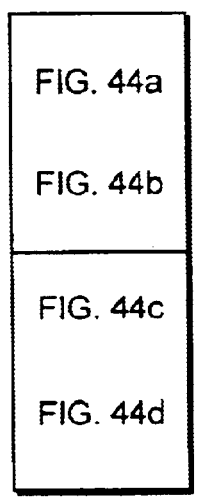
FIG. 44 is an illustration of the normalized conductivity data corresponding to the data of FIG. 43.
Figure 44A:
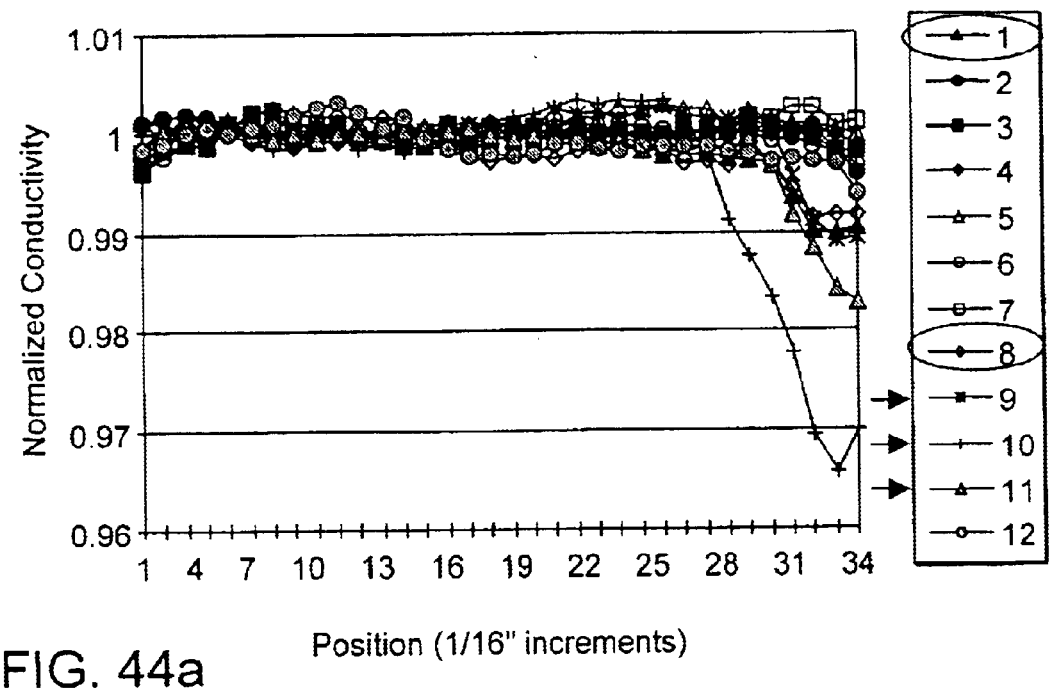
Figure 44B:
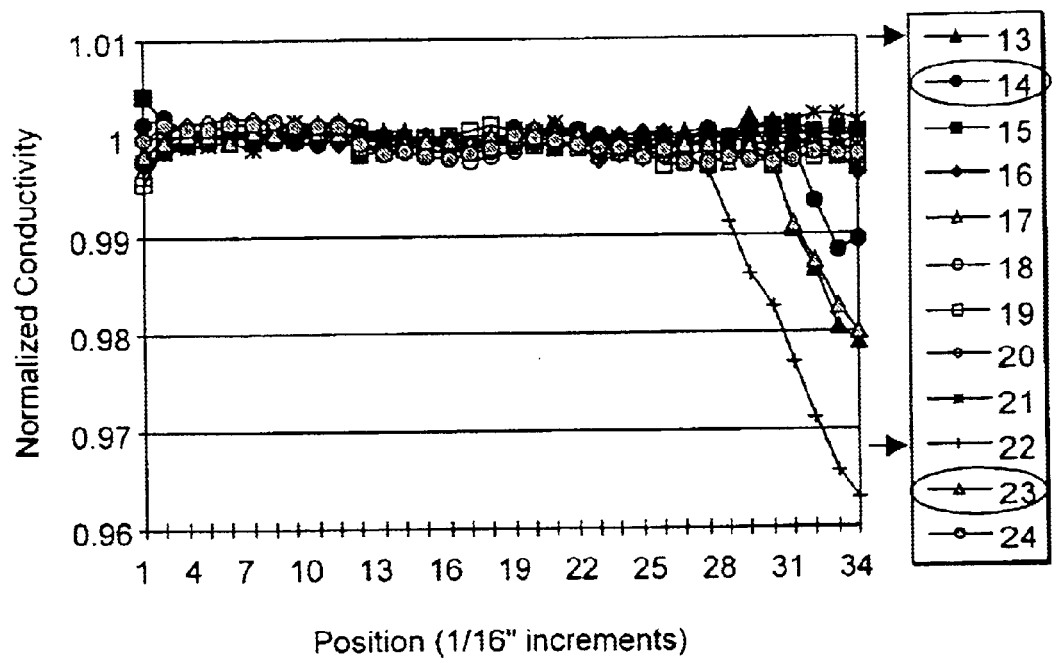
Figure 44C:
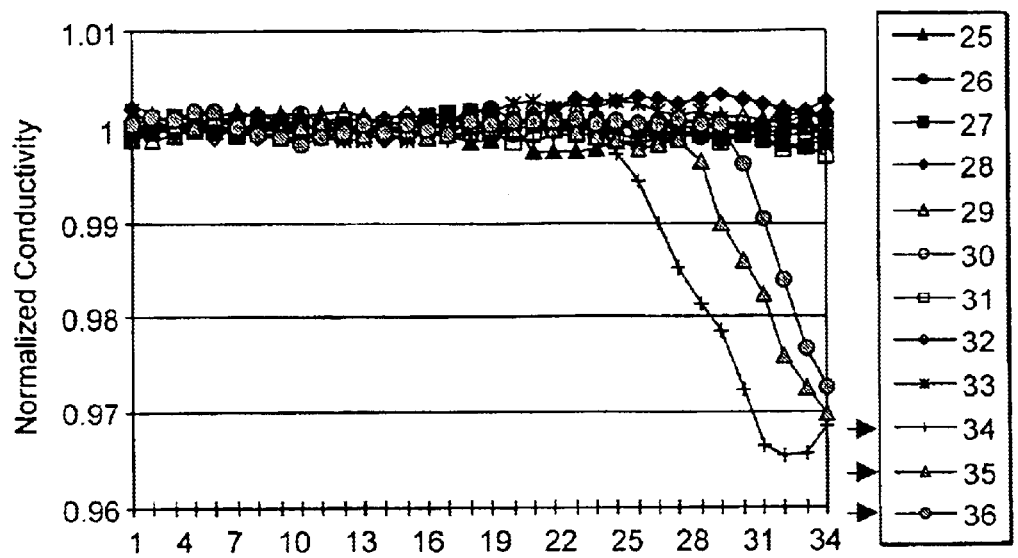
Figure 44D:
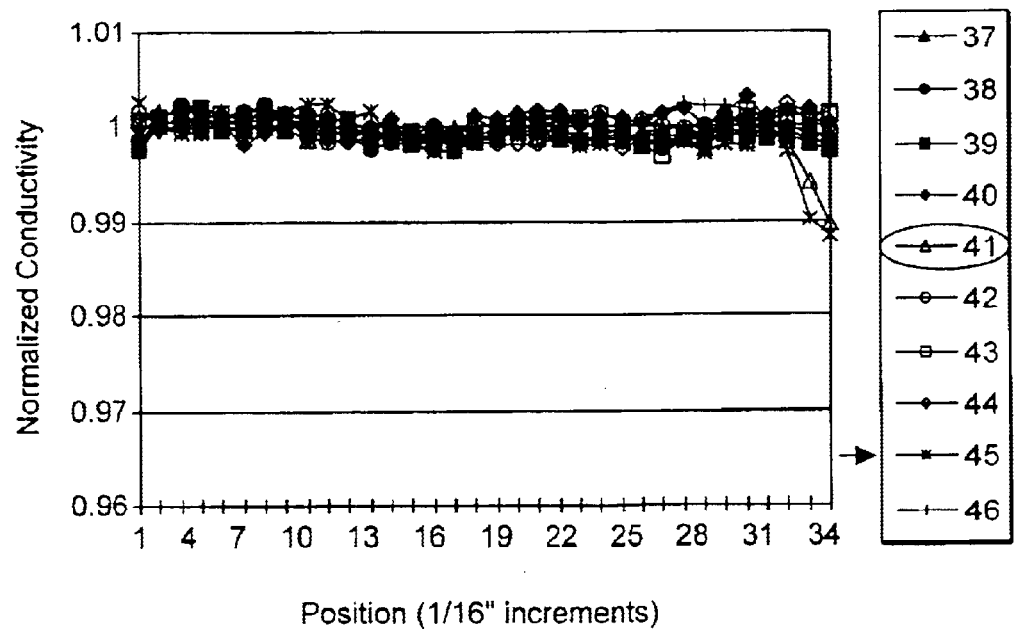

FIG. 43 shows the results of the slot inspection in all 46 slots, with some slots showing the characteristic decrease in conductivity associated with a crack. Both FIGS. 42a, 42b, and 43 present the absolute electrical conductivity without any normalization. The data from FIG. 43 after normalization to account for edge effects are given in FIG. 44. The slots that contained a distinct conductivity decrease and indicate the presence of a crack are marked in the legend for each plot. The arrows mark the slots where the UT inspection reported reject indications; the slots where the MWM detected cracks while the UT indications were below the reject threshold of 30% are encircled. In addition to conductivity vs slot location information, the grid measurement methods provide lift-off vs slot location information. The lift-off data appear to indicate the extent and relative severity of fretting.

Table 1 compares the findings of the MWM inspections with the UT inspection. The UT report identified rejected indications (>30%) in nine of the 46 slots (slots # 9, 10, 11, 13, 22, 34, 35, 36, and 45). The disk slots had regions of fretting damage and, according to the UT inspection report, some of the slots contained cracks in the fretting damage regions. In contrast, the MWM with Grid methods reliably detected cracks within fretting damage regions in 14 slots, including all nine slots with rejected UT indications and five additional slots (slot # 1, 8, 14, 23, and 41). For verification, the well-known procedure for taking acetate replicas, that provide a "fingerprint" image of the surface, was adapted for the characterization of the surface condition within the slots. These replicas confirmed the MWM findings and showed images of cracks in fretting damages regions.

TABLE 1

Comparison of crack detection by MWM with reported UT indications for an F110 Stage 2 fan disk.

| Slot # | UT Acceptance | UT Response % | MWM Detection | Crack Length as Verified by Replicas | Distance from slot edge to the nearest crack tip |
|---|---|---|---|---|---|
| 1 | Accept | 23 | Yes (E) | 0.16 in. | 0.23 in. |
| 2 | Accept | 20 | ?(A/ART/ERT) | 0.05 in. | 0.16 in. |
| 3 | Accept | 20 | No (A) | No cracks | No cracks |
| 4 | Accept | 20 | No (A) | ~0.015 in. | 0.26 in. |
| 5 | Accept | 23 | No (A) | 0.045 in. | (0.20 in. |
| 6 | Accept | 20 | ?(A/ERT) | 0.080 | >0.12 in. |
| 7 | Accept | 22 | No (A) | No cracks | No cracks |
| 8 | Accept | 21 | Yes (E) | 0.16 in. | 0.32 in. |
| 9 | Reject | 34 | Yes (E) | 0.20 in. | 0.26 in. |
| 10 | Reject | 116 | Yes (E) | 0.21 in. | 0.2 in. |
| 11 | Reject | 52 | Yes (E) | 0.22 in. | 0.28 in. |
| 12 | Accept | 9 | No (A) | Possibly <0.015 in. | 0.44 in. |
| 13 | Reject | 47 | Yes (E) | 0.28 in. | 0.20 in. |
| 14 | Accept | 15 | Yes (E) | 0.13 in. | 0.22 in. |
| 15 | Accept | 10 | No (A) | Possibly 2 adjacent cracks (combined length (0.03 in.) | 0.22 in. |
| 16 | Accept | 10 | ?(A/ART/ERT) | 0.005 to 0.015 in. long intermittent cracks over 0.15 in | 0.13 in. |
| 17 | Accept | 12 | No (A) | No cracks | No cracks |
| 18 | Accept | 8 | No (A) | No cracks | No cracks |
| 19 | Accept | 9 | No (A) | Possibly one 0.03 in. crack? | 0.29 in. |
| 20 | Accept | 10 | No (A) | No cracks | No cracks |
| 21 | Accept | 10 | No (A) | No cracks | No cracks |
| 22 | Reject | 63 | Yes | 0.44 in. | 0.18 in. |
| 23 | Accept | 15 | Yes | 0.19 in. | 0.16 in. |
| 29 | Accept | 7 | ?No (A) | 0.005 to 0.025 in. long intermittent cracks over 0.165 | 0.29 in. |
| 30 | Accept | 7 | ?(A/ART/ERT) | Two adjacent cracks (comb. length (0.04 in.) plus two 0.05 in. cracks | 0.26 in. |
| 33 | Accept | 17 | ?(A/ART) | Possibly 2 cracks, 0.02 in. each, about 0.1 in. apart | |
| 34 | Reject | 120 | Yes | (0.34 in.) | 0.25 in. |
| 35 | Reject | 68 | Yes | (0.440 in | 0.16 in |
| 36 | Reject | 54 | Yes | Not replicated | Not replicated |
| 41 | Accept | 12 | Yes | 0.15 in. | 0.36 in. |
| 45 | Reject | 41 | Yes | 0.15 in. | 0.21 in. |

Note: A-accept; E-evaluate (subject to an evaluation for repair/retire decisions); ART-accept on retest; ERT-evaluate on retest. These decisions depend on the threshold settings in the application module.

Figure 50:
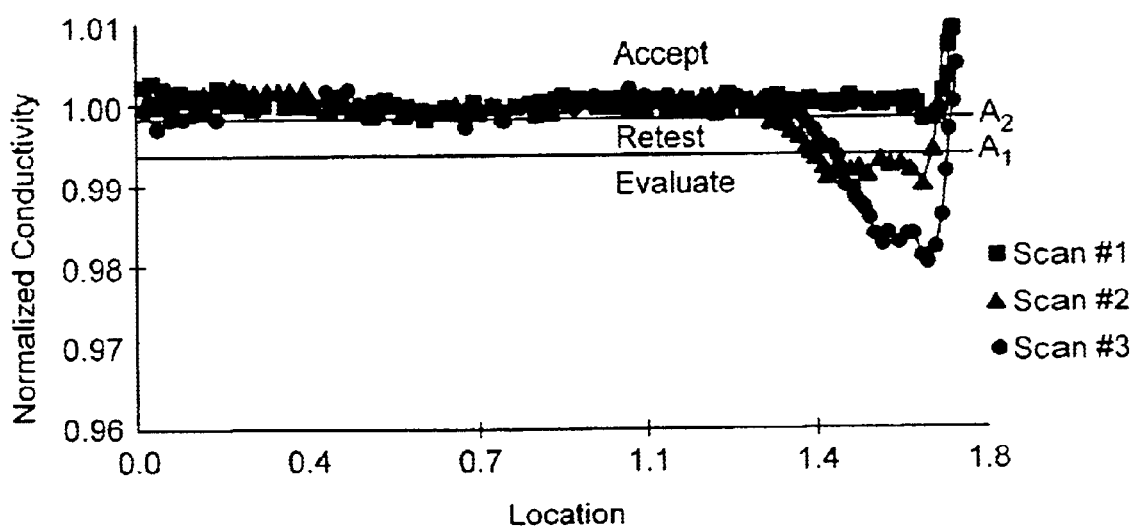
FIG. 50 illustrates several measurement scans across three engine disk slots, along with nominal detection thresholds.

Additional measurements were also performed to illustrate the use of an encoder for determining the position in a slot and sequential thresholds for determining the acceptability of a disk slot. A typical set of measurement scan results is illustrated in FIG. 50. The normalized electrical conductivity, measured with the MWM, is plotted against the sensor position, measured with the linear encoder. For each scan, the initial position of the sensor in the slot is set visually, usually by aligning a "corner" of the shuttle with the top surface of the slot. The conductivity is then measured as the shuttle is passed through the slot at a reasonably constant rate. The presence of a crack in the slot causes a reduction in the electrical conductivity as the sensor approaches the slot edge; as the sensor leaves the slot and goes off the edge, the effective electrical conductivity dips and becomes very large (eventually going off of the measurement grid). The measured electrical conductivity is normalized by the average conductivity near the center of the slot, prior to reaching the region of interest near the slot edge. Typically, the averaging was performed over the 0.8 to 1.3 inch region while the edge of the slot was in the 1.7 to 1.9 inch region; based on a limited number of scans, averaging from 0.5 to 1.3 inches does not appear to affect the measurement results. Although the cracks in some of the slots extend from the edge into the averaging region, the signal obtained from the cracks still fall into the "evaluate" region for the response, as described below. The minimum value measured for the normalized electrical conductivity is used to determine the presence of a crack.

In these tests the protocol for the acceptance decision for each slot is based on a sequential decision process. Two thresholds were used in this process and are denoted by the labels A1 and A2 in FIG. 50. In the decision process, each slot scan is compared to the two thresholds. A1 is the RetestEvaluate threshold while A2 is the Accept/Retest threshold. If the normalized conductivity is above A2, then the decision is ACCEPT (e.g., both A1 and A2 pass). If the normalized conductivity is below A1 on the initial scan, the slot is thought to contain a flaw and EVALUATE is the final decision (e.g., both A1 and A2 do not pass). If the minimum normalized conductivity falls between A1 and A2 (e.g., A1 pass, A2 does not pass), the slot must be retested several times. Then the average of the inspection scans is used to reach a decision on the slot. Now, if the average is below A2, the final decision is EVALUATE upon retest. Otherwise, the outcome will be ACCEPT upon retest. In the case a slot is accepted upon retests, a supervisor concurrence and signature are required. Thus, for the case of "ACCEPT," no further action is required other than making a record. For the case of "RETEST," the slot has to be re-inspected several times. The Retested slot will then be labeled as either Accept or Evaluate. "EVALUATE" means that the slot is likely to have a significant flaw that needs to be evaluated by other methods.

These thresholds are based on statistics for the disks being measured and the training set population. In this case, the threshold level A1 was set to provide an Evaluate decision for a 0.16 inch long crack while the threshold level A2 was set to be near the minimum in normalized conductivity for a 0.080 inch long crack. As the number of disks and slots inspected increases, the threshold levels can be determined with statistical methods based on the probability of detection for a given crack size. Representative threshold levels are A1=0.992 and A2=0.995

Figure 51:
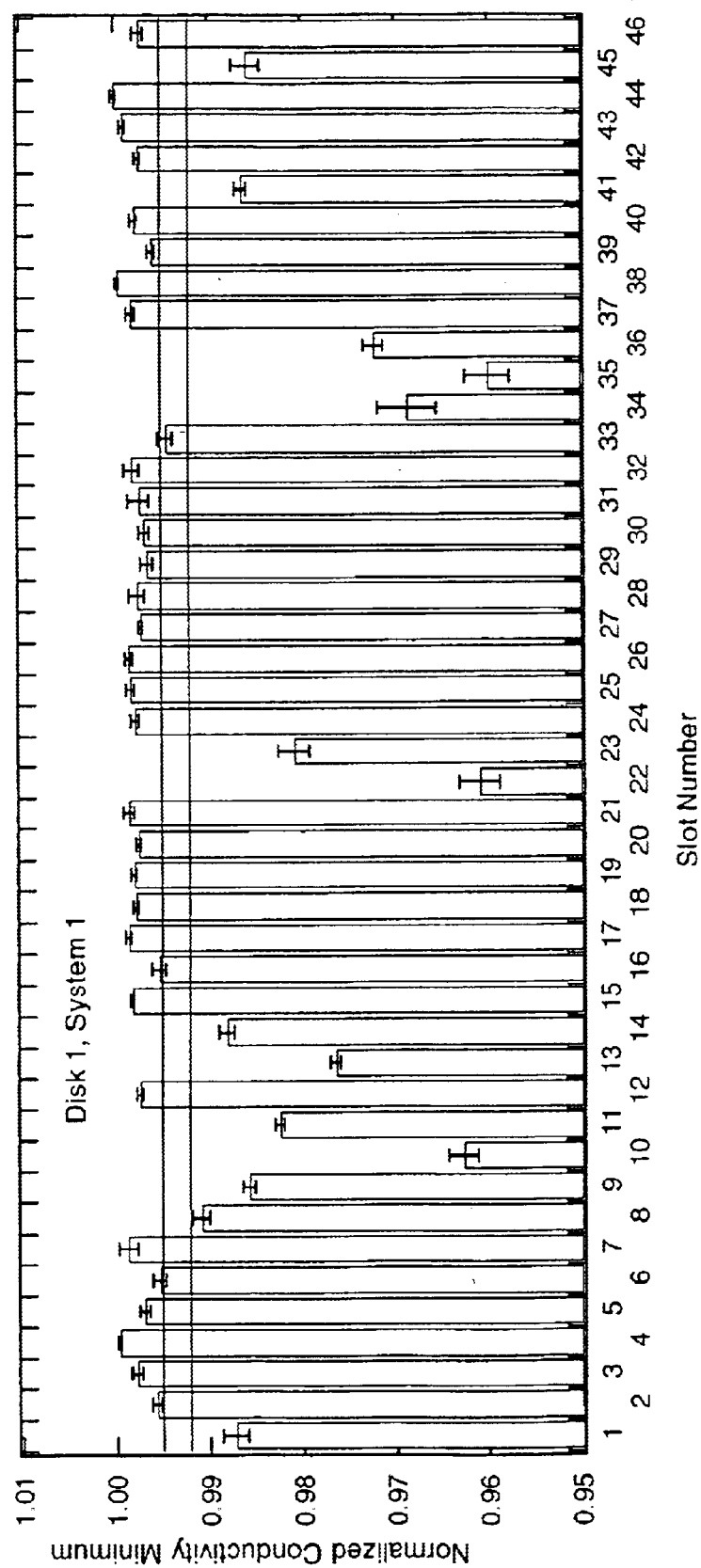
FIG. 51 illustrates the variation in the normalized conductivity due to the formation of cracks in engine disk slots.

The minimum in the normalized conductivity for all of the slots on a disk are illustrated in FIG. 51. The column bars denote the average values while the error bars show the standard deviation of the measurements. The effect of altering the threshold levels can be seen. The A1 (lower) threshold is typically set so that larger cracks (greater than 0.1 inches long) are evaluated after the first scan. The A2 (upper) threshold is set to differentiate the smaller cracks from the noise in unflawed slots. Again, the error bars denote the variability in the measurements so choosing an A2 threshold that passes through (or near) the error bars will have an intermediate (i.e., between zero and one) probability of detection. Once more cracks have been characterized (e.g., replicated), better statistics can be applied to determining the thresholds that should be used for detection of a given crack size.

Figure 45A:
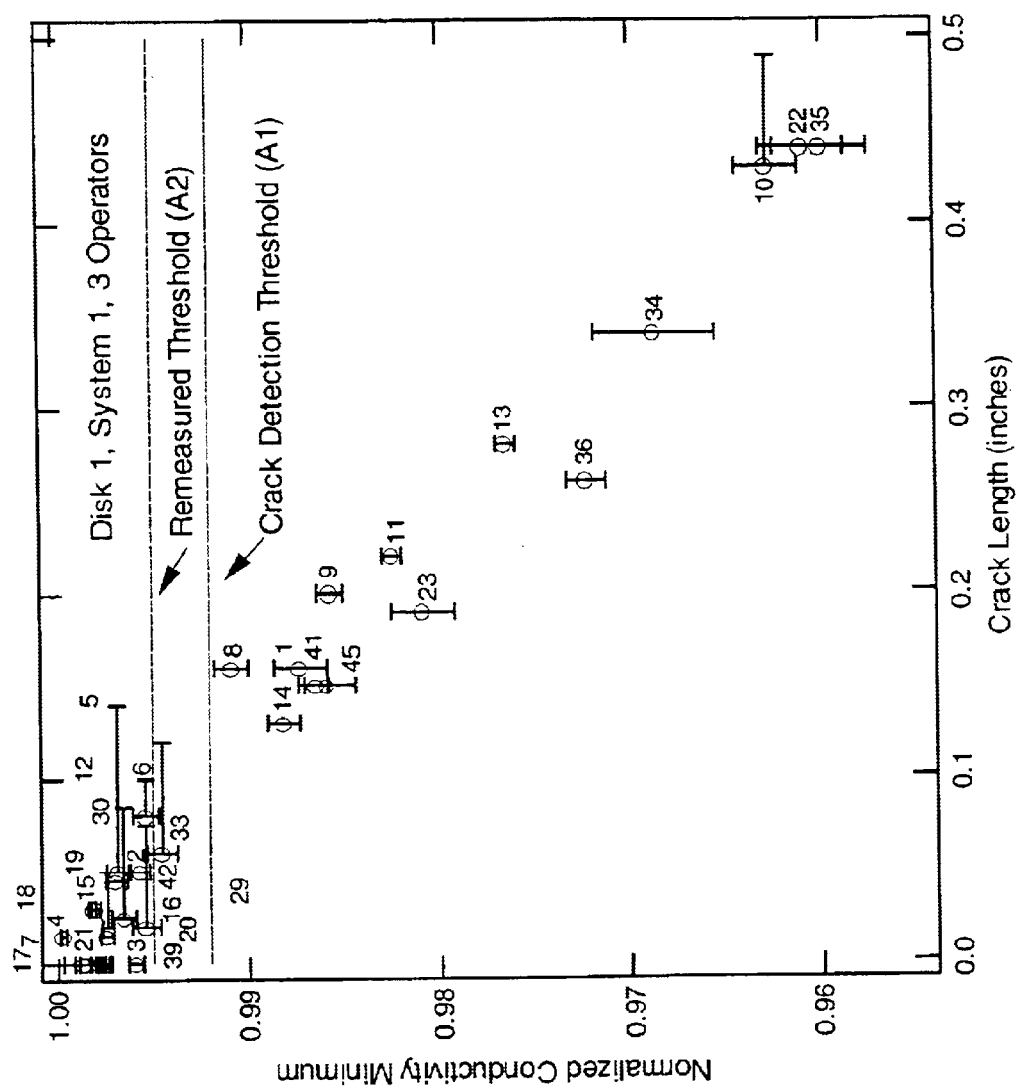
FIG. 45(a) is an illustration of the reduction in the normalized conductivity dependence on crack length for the slots listed in Table 1. Nominal thresholds for crack detection is indicated. (b) provides an expanded view of the response of the smaller cracks.
Figure 45B:
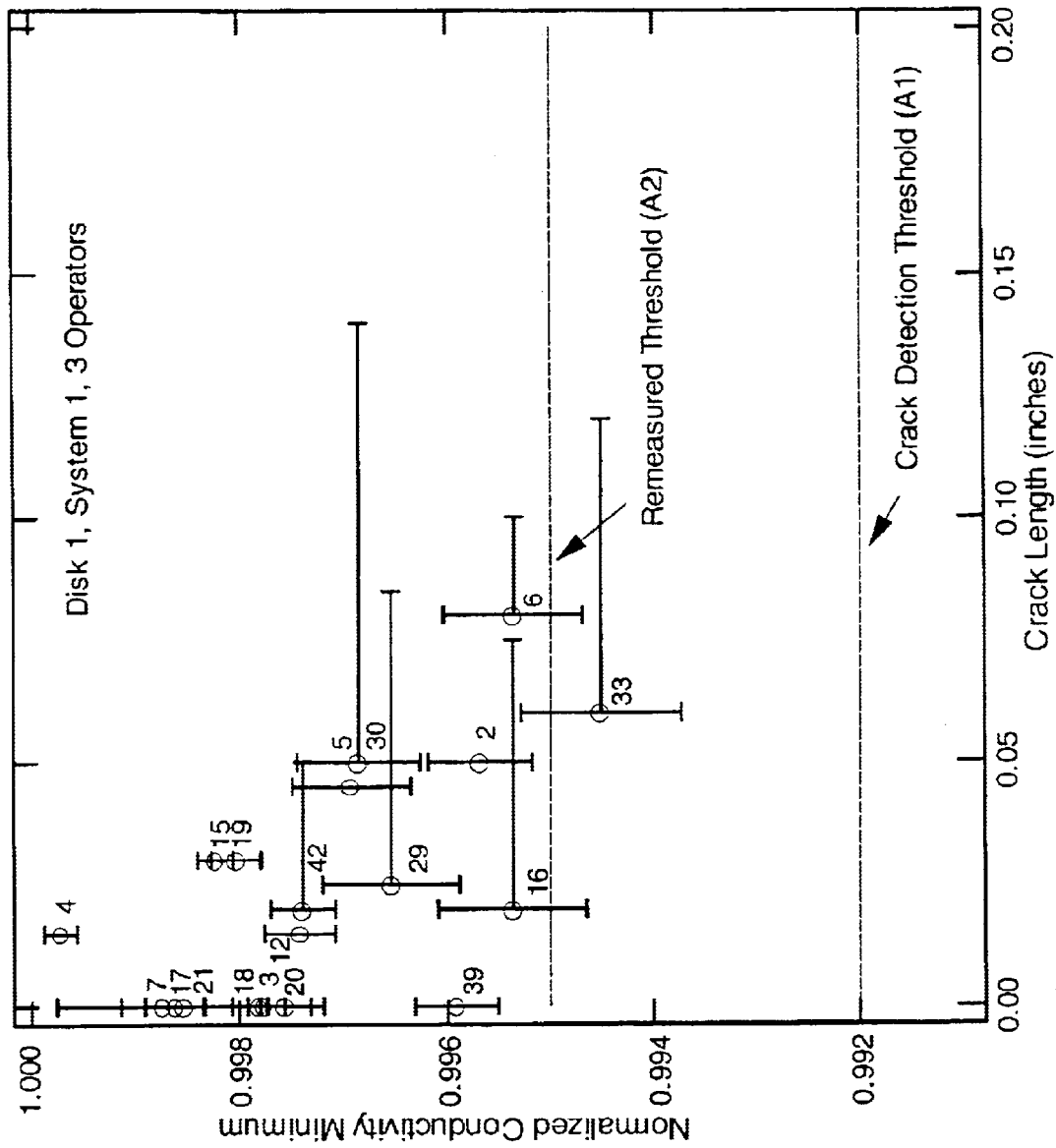

FIGS. 45a and 45b illustrate the crack length dependence of the minimum in the normalized conductivity for the slots of Table 1 which had been replicated. In this case, three to 11 measurements were performed on each slot. Three different inspectors inspected each slot. The average and standard deviation for the measurements on each slot are illustrated in FIGS. 45a and 45b. The vertical error bars represent the standard deviations in the measurements between the operators and illustrates the operator variability in the measurement results. The horizontal error bars denote the effective crack length due to multiple cracks or clusters of cracks greater than 0.005 inches long. The slot number is given on the right side of each data point. The thresholds indicate the evaluate (A1) and retest (A2) levels for the minimum in the normalized conductivity. Clearly, adjusting the retest level (A2) slightly will affect the probability of detection of the smaller cracks, such as the 0.080" and 0.050" long cracks (slots 6 and 2, respectively). The minimum detectable crack size depends upon the selection of the detection thresholds and the variability of the instrument, operators, and other noise factors. The detection thresholds set the minimum allowable reduction in the normalized conductivity for an acceptable scan. Choosing thresholds beyond the measurement "noise" level that minimizes the number of false indications also sets the minimum detectable crack size.

The use of MWM sensors and Grid measurement methods can also provide a more meaningful assessment of weld quality than conventional inspection methods. The high cost and complexity of titanium welding are caused by special cleaning and shielding procedures to preclude contamination. Quality control of titanium welds includes, among other things, inspection for contamination. Currently, titanium welds are accepted or rejected based on surface color inspection results, even though the surface color has not been a reliable indicator of weld contamination level.

The capability of the MWM to characterize contamination of the welds was demonstrated on several test specimens. Autogenous GTA welds were fabricated in six titanium Grade 2 plates with shielding gases that included high purity argon, three levels of air contamination, and two levels of CO contamination. The measurements were performed in a point-by-point "scanning" mode across each weld so that each scan included the titanium, Grade 2 base metal, heat-affected zones on each side of a weld, and weld metal. The footprint of the sensor was ½ in. by ½ in.

Figure 48:
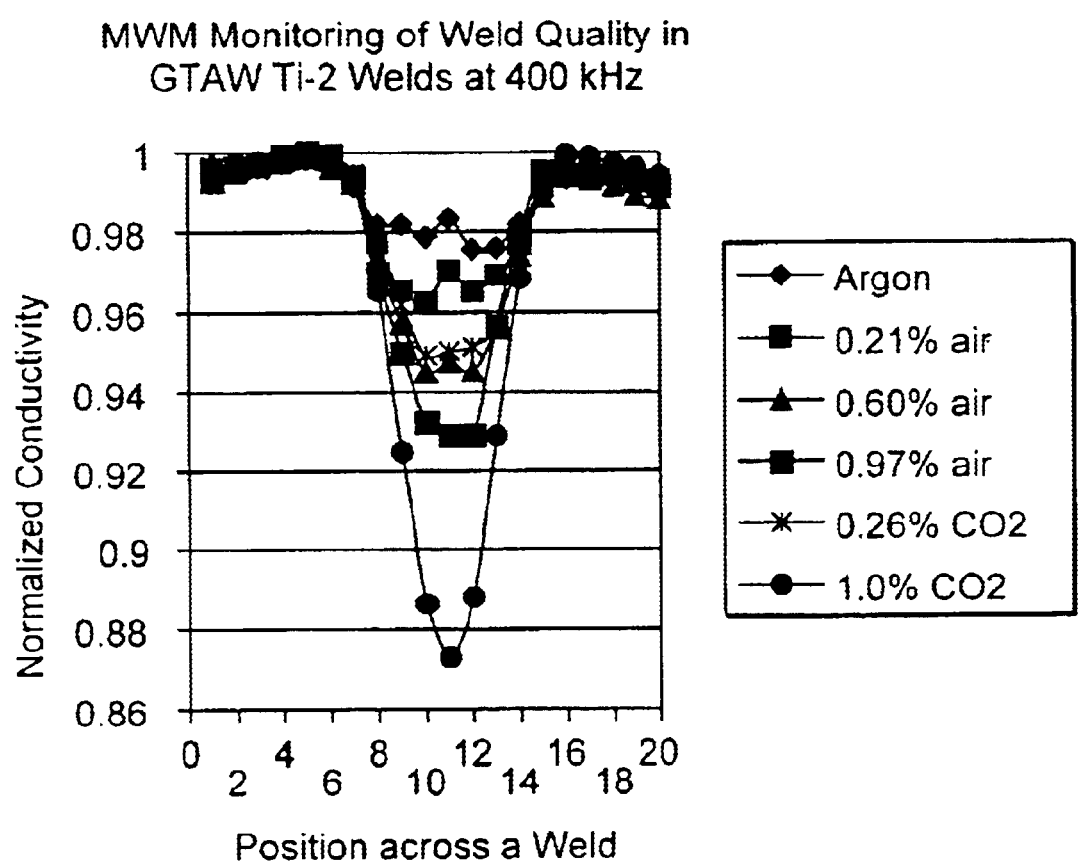
FIG. 48 shows MWM measurement scans across a "clean" weld and across contaminated titanium welds.
Figure 49:
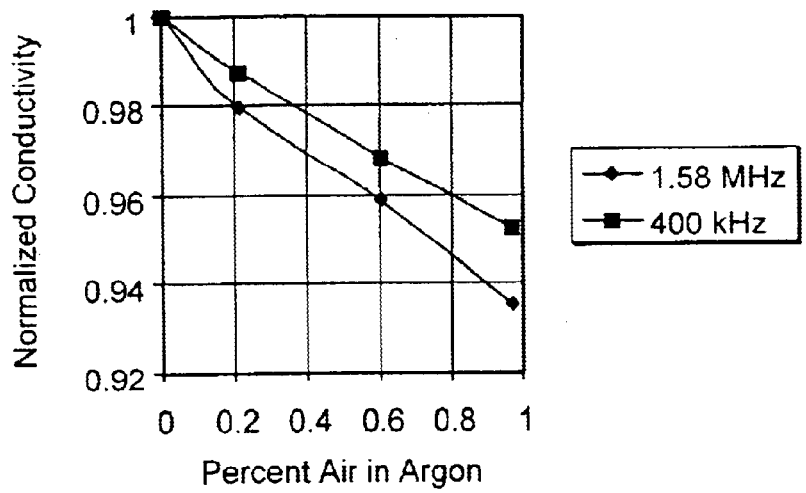
FIG. 49 illustrates the effect of shielding gas contamination on the normalized conductivity of titanium welds.

FIG. 48 shows an MWM measured electrical conductivity profile across the welds obtained at a frequency 400 kHz. All measured conductivity values were normalized by the maximum conductivity in the base metal. The dip in conductivity in each curve corresponds to the weld metal, whereas the left and right "shoulders" correspond to the base metal. In the specimen containing the weld fabricated with pure argon as the shielding gas, the conductivity of the weld metal is only slightly lower than conductivity of the base metal. There is a general trend of conductivity decrease with contamination level. This trend is illustrated in FIG. 49, for excitation frequencies of 400 kHz and 1.58 MHz, as air contamination in the shielding gas reduces the conductivity of the titanium weld metal. In this plot, the conductivity of weld metal is normalized by the minimum measured conductivity of weld fabricated in pure argon.

Periodic field eddy-current sensors can also be used to detect overheat damage in gun barrels or other steel components that may be coated with another material or uncoated.

As an example, measurements were performed on two semi-cylindrical samples from a longitudinally sectioned 25-mm gun barrel. The section of this particular gun barrel, located between axial positions 8 in. and 24 in. away from the start of the rifling, had experienced overheating. Sample 2a (in FIGS. 52 and 53) was removed from the overheated section and from the part of the gun barrel between the 7-in. and 16-in. axial positions. Sample 5 (in FIGS. 52 and 53) is a section of the gun barrel not affected by overheating and from the part of the gun barrel between the 41-in. and 51-in. axial positions. The gun barrels were made of a low-alloy steel, which was heat-treated originally to obtain tempered martensite microstructure. In the overheated section, there was a distinct heat-affected zone around the bore where the resulting ferritic-bainitic microstructure suggests the temperatures could have been at least 900 to 1100(F. The inside surface of the gun barrel was plated with electrodeposited chromium where the thickness ranged from 0.10 mm to 0.20 mm.

Figure 52:
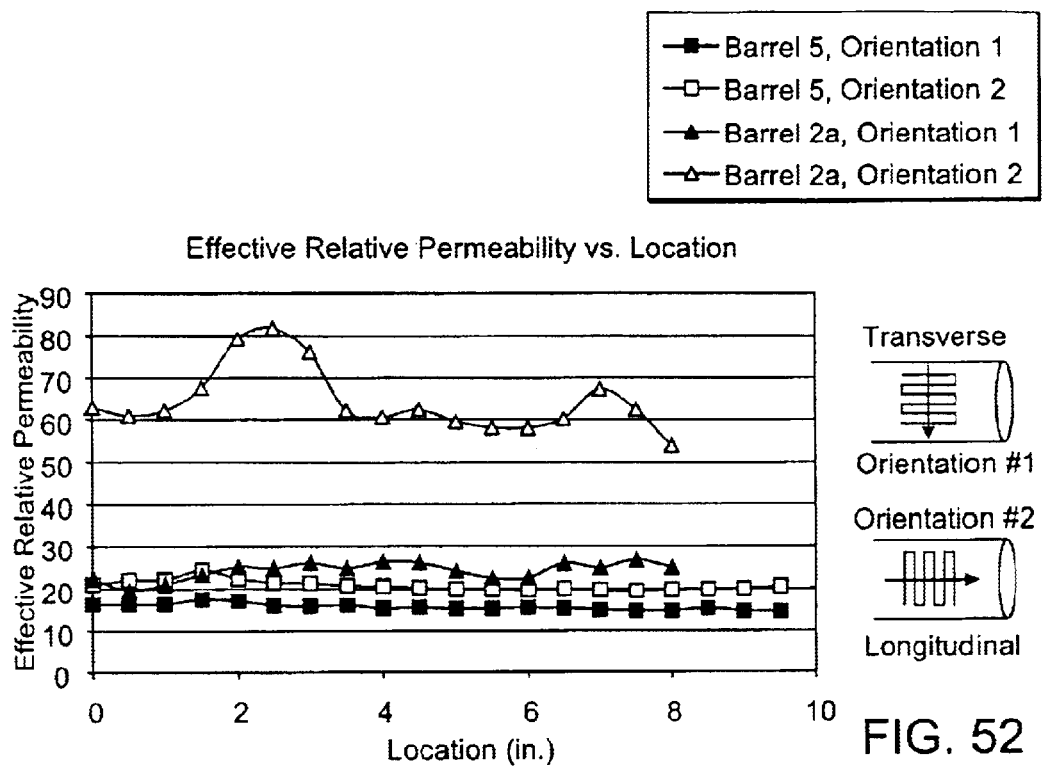
FIG. 52 illustrates the effective relative permeability variation with position along the axis of gun barrel.
Figure 53:
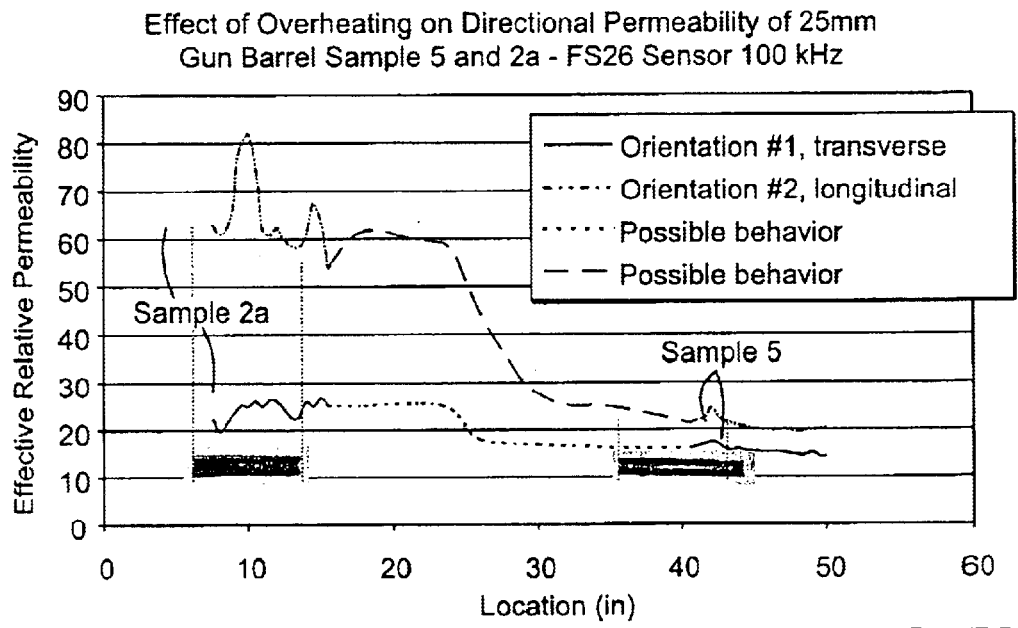
FIG. 53 illustrates the MWM measured effective relative permeability in two regions and possible behavior between the two regions along the axis of a 25 mm diameter partially overheated gun barrel.

FIGS. 52 and 53 show a representative set of MWM measurements on gun barrel samples. These measurements were performed with a JENTEK GridStation using magnetic permeability-lift-off measurement grids at a frequency of 100 kHz. Axial scans along the length of the samples were performed with the MWM sensor windings oriented both parallel (Orientation #1) and perpendicular (Orientation #2) to the gun barrel axis. FIG. 52 shows the results of the MWM axial scans in terms of effective relative magnetic permeability vs axial position (within each sample) along the barrel axis. Note that the MWM is most sensitive to permeability in the direction perpendicular to its longer winding segments. The data reveal that the longitudinal effective permeability measured with Orientation #2 in Sample 5 (not affected by overheating) is higher than the transverse permeability measured with Orientation #1, indicating some anisotropy. The MWM data for Sample 2a show that overheating dramatically increased the longitudinal effective permeability measured with Orientation #2 in sample 2a compared to the transverse effective permeability, measured with Orientation #1. FIG. 53 shows the effective permeability is plotted vs distance from the start of rifling along the barrel axis. The MWM measured results are shown in solid lines while the dotted lines indicate a possible trend in relative magnetic permeability in the region between Sample 2a and Sample 5.

These measurements indicate that the MWM probe response was characteristic of a ferromagnetic material. Note that the low-alloy steel is a ferromagnetic material whereas the electrodeposited chromium plating is nonmagnetic unless the plating had been exposed to high temperatures for sufficiently long time to effect diffusion of iron into the deposited plating. At a frequency of 100 kHz, the estimated depth of sensitivity in pure chromium is estimated to be approximately 0.5 mm, which is greater than the thickness of the electrodeposited chromium plating. As result, the MWM "sees" beyond the plated layer of chromium and the measurements reflect the effective permeability and microstructural conditions of the low-alloy steel. Thus, the unique bidirectional permeability measurement capabilities of the MWM provide sensitivity to the property changes caused by overheating. For rapid inspections of gun barrels, cylindrical probes having MWM sensors in both parallel and perpendicular orientations can be used so that a single measurement scans provides both measurements of the effective permeability.

Figure 54:
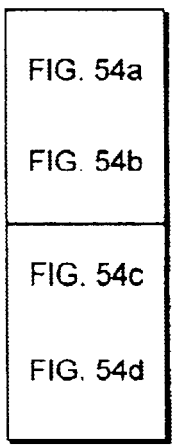
FIG. 54 illustrates hidden crack detection and sizing in a nickel-based alloy sample, using a two-frequency method.
Figure 54A:
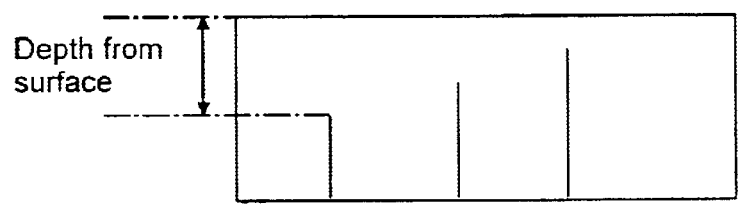
Figure 54B:
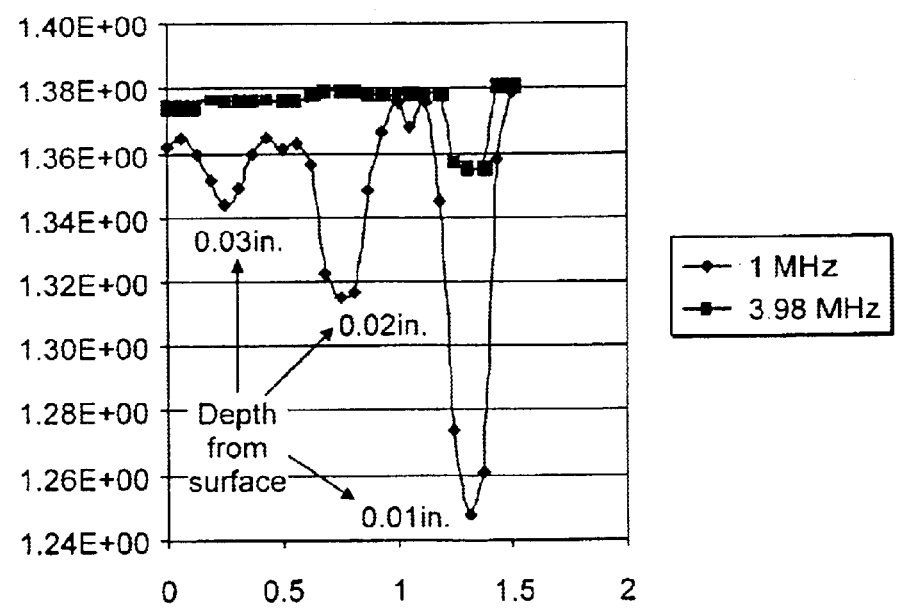
Figure 54C:
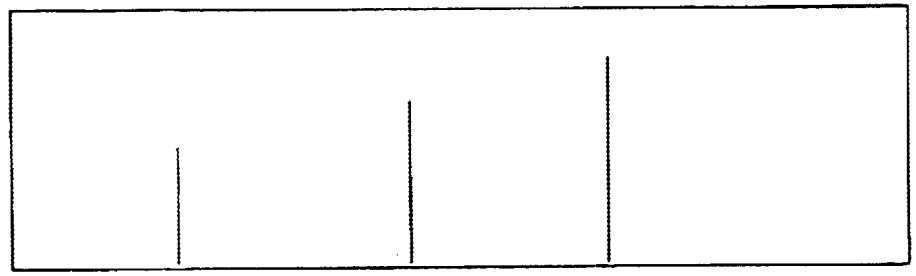
Figure 54D:
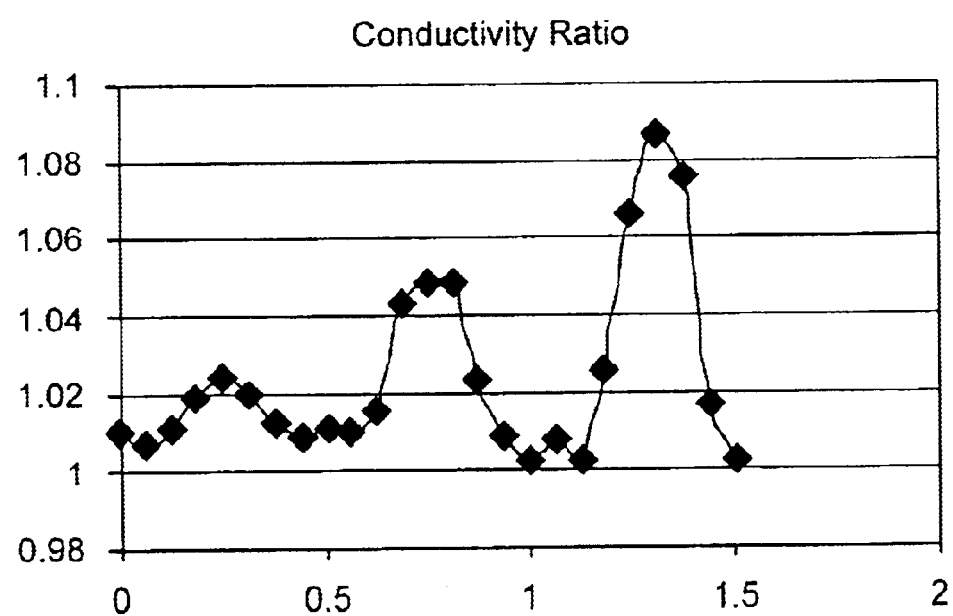

Periodic field eddy-current sensors can also be used to detect and quantify the depth of subsurface cracks. As an example, consider the measurement illustrated in FIG. 54. In this case, two-frequency conductivity—lift-off measurements were performed on the back surface of a nickel alloy sample having notches that simulate crack-like flaws on the front surface. FIG. 54 shows a schematic of the flaw pattern in the sample and the MWM measured conductivity scan at two frequencies. A simple ratio of the two-frequency absolute conductivity measurements (after passing the raw data through the two-unknown measurement grid) provides a robust correlation with distance from the flaw tip to the back surface. This method can be used to detect and determine depth or distance to hidden cracks for both fatigue cracks and, for some components, cracking associated with corrosion fatigue.

While this invention has been particularly shown and described with references to preferred embodiments thereof, it will be understood by those skilled in the art that various changes in form and details may be made therein without departing from the scope of the invention encompassed by the appended claims.

References incorporated by reference in their entirety:

Air Force Association (1997), "Air Force Almanac", May 1997.

Auld, B. A. and Moulder, J. C. (1999), "Review of Advances in Quantitative Eddy-Current Nondestructive Evaluation," Journal of Nondestructive Evaluation, vol. 18, No. 1.

Committee On Aging of US Air Force Aircraft (1997), "Aging of US Air Force Aircraft", ISBN 0-309-05935-6, 1997.

Friedel, J. (1964), Dislocations, Pergamon Press.

Goldfine, N., A. Washabaugh, K. Walrath, P. Zombo, and R. Miller (1998), "Conformable Eddy-Current Sensors and Methods for Gas Turbine Inspection and Health Monitoring", ASM International, Gas Turbine Technology Conference, Materials Solutions '98, Rosemont, Ill.

Goldfine, N., D. Schlicker, and A. Washabaugh (1998 NASA), "Surface-Mounted Eddy-Current Sensors for On-Line Monitoring of Fatigue Tests and for Aircraft Health Monitoring," $2^{nd}$ NASA(FAA/DoD Conference on Aging Aircraft.

Kramer, I. R. (1974), Metallurgical Transactions, v. 5, p. 1735.

Regler, F. (1937), Zeitschrift für Elektrochemie, v. 43, p. 546

Regler, F. (1939), Verformung und Ermüdung Metallischer Werkstoffe.

Suresh, S. (1998), Fatigue of Materials, Second Edition, Cambridge University Press.

Taira, S., and Hayashi, K. (1966), Proc. $9^{th}$ Japanese Congress of Testing Materials.

Weiss, V. and Oshida, Y. (1984), "Fatigue Damage Characterization using X-Ray Diffraction Line Analysis", in *Fatigue* 84, p 1151, Butterworth.

Related Documents

This present invention is related to:

1. Navy Phase I Proposal, titled "Application of the Meandering Wire Magnetometer to Detection and Quantification of Cumulative Fatigue Damage in Aircraft Structural Components", Topic #N95-033, dated Jan. 12, 1995
2. Navy Phase I Final Report, titled "Application of the Meandering Wire Magnetometer to Detection and Quantification of Cumulative Fatigue Damage in Aircraft Structural Components", dated Apr. 30, 1996, Contract #N00019-95-C-0220
3. Navy Phase II Proposal, titled "Application of the Meandering Wire Magnetometer to Detection and Quantification of Cumulative Fatigue Damage in Aircraft Structural Components", Topic #N95-033, dated Jun. 17, 1996
4. Navy Phase II Final Report, titled "Application of the Meandering Wire Magnetometer to Detection and Quantification of Cumulative Fatigue Damage in Aircraft Structural Components", dated Feb. 16, 1999, Contract #N00421-97-C-1120
5. Air Force Phase I Proposal, titled "Portable Accumulated Fatigue Damage Inspection System Using Permanently Mounted and Wide-Area Imaging MWM-Arrays", Topic #AF99-286, dated Jan. 11, 1999
6. Air Force Phase II Proposal, titled "Portable Accumulated Fatigue Damage Inspection System Using Permanently Mounted and Wide-Area Imaging MWM-Arrays", Topic #AF99-286, dated Dec. 3, 1999
7. Air Force Phase I Final Report, titled "Portable Accumulated Fatigue Damage Inspection System Using Permanently Mounted and Wide-Area Imaging MWM-Arrays", dated Mar. 10, 2000, Contract #F09650-99-M-1328
8. Technical Paper titled "Surface-Mounted Eddy-Current Sensors for On-line Monitoring of Fatigue Tests and for Aircraft Health Monitoring", presented at the Second Joint NASA/FAA/DoD Conference on Aging Aircraft, August 1998
9. JENTEK Sensors Trip Report to Tinker AFB, dated Jul. 6, 1999
10. Technical Abstract titled "New MWM Arrays with High Resolution and Increased Depth of Sensitivity for Quantitative Imaging of "Hidden" Fatigue and Corrosion over Wide Areas, submitted to the Third Joint NASA/FAA/DoD Conference on Aging Aircraft, September 1999

11. Technical Paper titled "Recent Applications of Meandering Winding Magnetometers to Materials Characterization", presented at The 38$^{th}$ Annual British Conference on NDT, Sep. 13–16, 1999.
12. Technical Paper titled "Anisotropic Conductivity Measurements for Quality Control of C-130/P-3 Propeller Blades Using MWM(-Sensors with Grid Methods", presented at the Fourth Joint DoD/FAA/NASA Conference on Aging Aircraft, May 16, 2000.
13. Presentation Slides titled "Anisotropic Conductivity Measurements for Quality Control of C-130/P-3 Propeller Blades Using MWM(-Sensors with Grid Methods", presented at the Fourth Joint DoD/FAA/NASA Conference on Aging Aircraft, May 6, 2000.
14. FAA Year Two Final Report titled "Development of Conformable Eddy-Current Sensors for Engine Component Inspection," dated Aug. 4, 2000, Contract #DTFA0398-D00008.
15. Technical Paper titled "Application of MWM-Array Eddy-Current Sensors to Corrosion Mapping", presented at the 4$^{th}$ International Aircraft Corrosion Workshop, Aug. 22, 2000, which are incorporated herein by reference.

What is claimed is:

1. A method of monitoring damage at a fastener through the test substrate comprising:
mounting respective spatially periodic field eddy-current sensors to the test substrate at both ends of a fastener; and
sensing response of the test substrate to a magnetic field imposed by the eddy-current sensors.

2. A method as claimed in claim 1 where the damage is in the form of a crack.

3. A method as claimed in claim 2, wherein an action is taken at a predetermined sensor response level.

4. A method as claimed in claim 1 wherein at least one sensor from the eddy-current sensors is placed in an area likely to see damage and at least one sensing element is placed in an area unlikely to see damage.

5. A method as claimed in claim 1 wherein the eddy-current sensors are located at different radial distances from the fastener center.

6. A method as claimed in claim 1 wherein the eddy-current sensors are located at different circumferential positions around the fastener.

7. A method for monitoring damage at a fastener comprising:
mounting at least two eddy-current sensor arrays on a test substrate around respective fasteners;
connecting drive and sense conductors of the eddy-current sensors with a single cable to a data acquisition system; and
sensing response of the test substrate to a magnetic field imposed by the eddy-current sensors.

8. A method as claimed in claim 7 where the each sensor provides a separate output.

9. A method as claimed in claim 8 where the output is an absolute property measurement.

10. A method as claimed in claim 7 where the drive conductors of at least two sensors are connected in series.

11. A method as claimed in claim 10 where sense conductors of the at least two eddy-current sensor arrays are connected together to provide a differential measurement.

12. A method as claimed in claim 7 where separate drive connections are made to each sensor.

13. A method as claimed in claim 12 where the sense conductors are connected together to provide a common output connection.

14. A method as claimed in claim 7 where the drive conductors are connected together to provide a common drive signal.

15. A method as claimed in claim 14 where the sense conductors are connected together to provide a common output connection.

16. A method as claimed in claim 7 wherein at least one eddy-current sensor is placed in an area likely to see damage and at least one eddy-current sensor is placed in an area unlikely to see damage.

17. A method as claimed in claim 7 wherein the eddy-current sensors are located at different circumferential positions around the fastener.

18. A method for monitoring damage at a fastener comprising:
mounting a spatially periodic field eddy-current sensor array to a test substrate under the head of a fastener; and
sensing response of the test substrate to a magnetic field imposed by the eddy-current sensor array.

19. A method as claimed in claim 18 where at least one sensor is a circular spatially periodic field sensor.

20. A method as claimed in claim 18 where at least one eddy-current sensor is placed in an area likely to see damage and at least one eddy-current sensor is placed in an area unlikely to see damage.

21. A method as claimed in claim 18, wherein the test substrate is a test specimen.

22. A method for performing fatigue testing at a fastener comprising:
mounting an eddy current sensor array to a test substrate under the head of a fastener; and
sensing response of the test substrate to a magnetic field imposed by the eddy-current sensor array.

23. A method as claimed in claim 22 where the sensor further comprises a drive having at least two conductors where the current changes direction in at least one conductor.

24. A method as claimed in claim 22, wherein the test substrate is a test specimen.

25. A method of monitoring damage at a fastener comprising:
mounting a spatially periodic field eddy-current sensor array to a structure near a fastener, the sensor being mounted between layers of the structure attached by the fastener, and
sensing response of the test substrate to a magnetic field imposed by the eddy-current sensor array.

26. A method as claimed in claim 25 wherein the test substrate is a test specimen.

27. A method of monitoring damage at a fastener comprising:
mounting a spatially periodic field eddy-current sensor array to a test specimen, the sensor being mounted between layers of the test coupon attached by the fastener; and
sensing response of the test specimen to a magnetic field imposed by the eddy-current sensor array.

28. A method as claimed in claim 27 wherein the sensor is thin and conforms to the shape of the test specimen.

29. A method as claimed in claim 27 wherein the sensor is mounted using an adhesive.

30. A method as claimed in claim 27 wherein the sensor is mounted by pressing the sensor against the surface of the test specimen and using pressure to hold the sensor in place, the pressure being provided by an opposing surface whose shape matches the shape of the test specimen.

31. A method for performing fatigue testing at a fastener comprising:
mounting an eddy current sensor array to a test substrate under the head of a fastener; and
sensing response of the test substrate to a magnetic field imposed by the eddy-current sensor array.

32. A method of monitoring damage at a fastener comprising:
mounting a spatially periodic field eddy-current sensor array to a structure near a fastener, the sensor array being mounted between layers of the structure attached by the fastener; and
sensing response of the test substrate to a magnetic field imposed by the eddy-current sensor array, each eddy-current sensor having at least two drive conductors and the current changing direction in at least one conductor.

33. A method of monitoring damage at a fastener comprising:
mounting a spatially periodic field eddy-current sensor array to a structure near a fastener, the sensor being mounted between layers of the structure attached by the fastener;
sensing response of the structure to a magnetic field imposed by the eddy-current sensor; and
calibrating each sense element of the eddy-current sensor array by adjusting the response to an appropriate level.

34. A method as claimed in claim 33 where the calibration involves placing the sensor on the test structure and measuring the response of each sense element.

35. A method as claimed in claim 34 where the calibration further involves a second response measurement for each sense element with a nonconductive material placed between the sensor and the test material.

36. A method as claimed in claim 34 wherein the calibration includes varying the temperature of the test material.

37. A method of monitoring damage at a fastener comprising:
mounting a spatially periodic field eddy-current sensor array to a structure near a fastener, the sensor being mounted between layers of the structure attached by the fastener; and
sensing response of the structure to a magnetic field imposed by the eddy-current sensor array, each eddy current sensor having a periodic magnetic field produced by linear segments of its drive winding.

38. A method of monitoring damage at a fastener comprising:
mounting an eddy-current sensor array to a structure near a fastener, the sensor being mounted between layers of the structure attached by the fastener; and
sensing response of the structure to a magnetic field imposed by the eddy-current sensor array, the sensor array having a magnetic field produced by a drive winding formed from concentric conductors within the same plane.

39. A method as claimed in claim 38, wherein there is one or more sense elements per each conductor.

40. A method for monitoring damage at a fastener comprising:
mounting a spatially periodic field eddy current sensor array with a cylindrical support material shaped in the form of a washer;
mounting the cylindrical support to a test substrate under a fastener head; and
sensing response of the test substrate to a magnetic field imposed by the eddy-current sensor.

41. A method as claimed in claim 40 where the test substrate withstands compressive loads.

42. A method for monitoring damage under the head of a fastener comprising:
mounting an eddy current sensor array to a test substrate under the head of a fastener with sense elements located at different radial distances from the fastener center; and
sensing response of the test substrate to a magnetic field imposed by the eddy-current sensors.

43. A method for monitoring damage under the head of a fastener comprising:
mounting an eddy current sensor array to a test substrate under the head of a fastener with sense elements located at different circumferential positions around the fastener; and
sensing response of the test substrate to a magnetic field imposed by the eddy-current sensors.

44. A method of monitoring damage at a fastener comprising:
mounting an eddy-current sensor array to a structure near a fastener, the sensor being mounted between layers of the structure attached by the fastener with at least one sensing element placed in an area likely to see damage and at least one sensing element placed in an area unlikely to see damage; and
sensing response of the structure to a magnetic field imposed by the eddy-current sensors.

45. A method of monitoring damage at a fastener comprising:
mounting an eddy-current sensor array to a structure near a fastener, the sensor being mounted between layers of the structure attached by the fastener with sense elements located at different radial distances from the fastener center; and
sensing response of the structure to a magnetic field imposed by the eddy-current sensors.

46. A method of monitoring damage at a fastener comprising:
mounting an eddy-current sensor array to a structure near a fastener, the sensor being mounted between layers of the structure attached by the fastener with sense elements located at different circumferential positions around the fastener; and
sensing response of the structure to a magnetic field imposed by the eddy-current sensors.

47. A method for monitoring damage at a fastener comprising:
mounting an eddy-current sensor array with a cylindrical support material shaped in the form of a washer with at least one sensing element placed in an area likely to see damage and at least one sensing element placed in an area unlikely to see damage;
mounting the cylindrical support to a test substrate under a fastener head; and
sensing response of the test substrate to a magnetic field imposed by the eddy-current sensor array.

48. A method for monitoring damage at a fastener comprising:
mounting an eddy-current sensor array with a cylindrical support material shaped in the form of a washer the sense elements being located at different radial distances from the fastener center;
mounting the cylindrical support to a test substrate under a fastener head; and sensing response of the test substrate to a magnetic field imposed by the eddy-current sensor array.

49. A method for monitoring damage at a fastener comprising:
   mounting an eddy-current sensor array with a cylindrical support material shaped in the form of a washer the sense elements being located at different circumferential positions around the fastener;
   mounting the cylindrical support to a test substrate under a fastener head; and
   sensing response of the test substrate to a magnetic field imposed by the eddy-current sensor array.

50. A method for monitoring damage at a fastener comprising:
   mounting at least two eddy-current sensor arrays on a test substrate around fasteners;
   connecting drive windings of the eddy-current sensor arrays in series; and
   sensing a response of the test substrate to a magnetic field imposed by the eddy-current sensor arrays.

51. A method as claimed in claim 50 wherein each sensor has one or more sensing elements.

52. A method as claimed in claim 51 where the response from all of the sensing elements are monitored in parallel at essentially the same time.

53. A method as claimed in claim 50 where the sensors are used to monitor material properties at different locations to detect response changes.

54. A method as claimed in claim 53 where the changes in the response are related to damage in material.

55. A method as claimed in claim 53 where the response is used to detect the initiation of a crack.

56. A method as claimed in claim 53 where the response is used to monitor the growth of a crack.

57. A method as claimed in claim 53 where the response is used to estimate the length of a crack.

58. A method as claimed in claim 7 wherein the eddy-current sensors are located at different radial distances from the fastener center.

* * * * *

UNITED STATES PATENT AND TRADEMARK OFFICE
CERTIFICATE OF CORRECTION

PATENT NO. : 6,952,095 B1
DATED : October 4, 2005
INVENTOR(S) : Neil J. Goldfine et al.

It is certified that error appears in the above-identified patent and that said Letters Patent is hereby corrected as shown below:

Title page,
Item [75], Inventors, please delete "Vladimir Tsukernik, West Roxbury, MA (US)".

Signed and Sealed this

Twentieth Day of December, 2005

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,952,095 B1 |
| DATED | : October 4, 2005 |
| INVENTOR(S) | : Neil J. Goldfine et al. |

It is certified that error appears in the above-identified patent and that said Letters Patent is hereby corrected as shown below:

<u>Column 1,</u>
Line 14, delete heading "Government Support" and following paragraph, at lines 15 through 20.

Signed and Sealed this

Sixth Day of June, 2006

JON W. DUDAS
*Director of the United States Patent and Trademark Office*